(12) United States Patent
Aburatani et al.

(10) Patent No.: US 10,696,743 B2
(45) Date of Patent: Jun. 30, 2020

(54) DIAGNOSIS AND TREATMENT OF CANCER USING ANTI-DESMOGLEIN-3 ANTIBODIES

(71) Applicants: Chugai Seiyaku Kabushiki Kaisha, Tokyo (JP); The University of Tokyo, Tokyo (JP)

(72) Inventors: Hiroyuki Aburatani, Tokyo (JP); Shunpei Ishikawa, Tokyo (JP); Hirotaka Ito, Tokyo (JP); Kiyotaka Nakano, Tokyo (JP); Shigeto Kawai, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/430,031

(22) Filed: Feb. 10, 2017

(65) Prior Publication Data
US 2017/0152314 A1  Jun. 1, 2017

Related U.S. Application Data

(62) Division of application No. 12/308,695, filed as application No. PCT/JP2007/065834 on Aug. 14, 2007, now abandoned.

(30) Foreign Application Priority Data

Aug. 14, 2006 (JP) ................................ 2006-221230
Jan. 30, 2007 (JP) ................................ 2007-019108

(51) Int. Cl.
  *C07K 16/28* (2006.01)
  *G01N 33/574* (2006.01)
(52) U.S. Cl.
  CPC ....... *C07K 16/28* (2013.01); *G01N 33/57423* (2013.01); *C07K 2317/24* (2013.01); *C07K 2317/565* (2013.01); *C07K 2317/73* (2013.01); *C07K 2317/732* (2013.01); *C07K 2317/734* (2013.01); *C07K 2319/30* (2013.01); *G01N 2333/705* (2013.01)
(58) Field of Classification Search
  None
  See application file for complete search history.

(56) References Cited

U.S. PATENT DOCUMENTS

| 5,693,762 A | 12/1997 | Queen et al. |
| 6,602,684 B1 | 8/2003 | Umana et al. |
| 2005/0025760 A1 | 2/2005 | Tsunoda et al. |
| 2006/0057559 A1 | 3/2006 | Xu et al. |
| 2008/0193454 A1 | 8/2008 | Tureci et al. |
| 2010/0092457 A1 | 4/2010 | Aburatani et al. |

FOREIGN PATENT DOCUMENTS

| EP | 2548576 B1 | 11/2016 |
| WO | WO 99/57149 A2 | 11/1999 |
| WO | WO 02/086443 A2 | 10/2002 |
| WO | WO 03/020769 A1 | 3/2003 |
| WO | WO 2005/110338 A2 | 11/2005 |

OTHER PUBLICATIONS

Agackiran, Y., et al., "Desmoglein-3 and Napsin A double stain, a useful immunohistochemical marker for differentiation of lung squamous cell carcinoma and adenocarcinoma from other subtypes," *Appl. Immunohistochem. Mol. Morphol.* 20(4):350-355, Lippincott Williams & Wilkins, United States (2012).
Lewis, G.D. et al., "Differential responses of human tumor cell lines to anti-p185$^{HER2}$ monoclonal antibodies," *Cancer Immunol. Immunother.* 37:255-263, Springer-Verlag (1993).
Fukumoto, S., et al., "Overexpression of the Aldo-Keto Reductase Family Protein AKR1B10 Is Highly Correlated with Smokers' Non-Small Cell Lung Carcinomas," *Clinical Cancer Research* 11:1776-1785, American Association for Cancer Research (2005).
Fukuoka, J., et al., "Desmoglein 3 as a prognostic factor in lung cancer," *Human Pathology* 38:276-283, Elsevier Inc. (2007).
Inamura, K., et al., "Two subclasses of lung squamous cell carcinoma with different gene expression profiles and prognosis identified by hierarchical clustering and non-negative matrix factorization," *Oncogene* 24:7105-7113, Nature Publishing Group (2005).
Supplementary European Search Report for European Application No. 07792477.7, Munich, Germany, dated Mar. 26, 2010.
McMillan, J.R. et al., "Alterations in Desmosome Size and Number Coincide with the Loss of Keratinocyte Cohesion in Skin with Homozygous and Heterozygous Defects in the Desmosomal Protein Plakophilin 1," *J. Invest. Dermatol.* 121:96-103, The Society for Investigative Dermatology, Inc. (2003).
Abcam® Catalog, "Anti-Desmoglein 1 antibody [32-2B] (ab108490)," last updated on Dec. 24, 2011.
Abreu, R.d.S., et al., Global signatures of global and mRNA expression levels, *Mol. BioSyst.* 5:1512-1526, The Royal Society of Chemistry, United Kingdom (2009).
Habermann, J.K., et al., "Stage-Specific Alterations of the Genome, Transcriptome, and Proteome During Colorectal Carcinogenesis," *Genes, Chromosomes & Cancer* 46:10-26, Wiley-Liss, Inc., United States (2006).

(Continued)

*Primary Examiner* — Brad Duffy
(74) *Attorney, Agent, or Firm* — Nixon & Vanderhye P.C.

(57) ABSTRACT

Methods that involve detection of a DSG3 protein for diagnosing cancer are disclosed. In lung cancer, the expression of DSG3 was found to be enhanced at very high frequency at the gene level and protein level. Methods of the present invention can be carried out using an antibody that recognizes a DSG3 protein. Pharmaceutical compositions, cell growth inhibitors, and anticancer agents containing a DSG3-binding antibody as an active ingredient are also disclosed. Methods of inducing cell damage in DSG3-expressing cells and methods of suppressing proliferation of DSG3-expressing cells by contacting the DSG3-expressing cells with DSG3-binding antibodies are also disclosed.

9 Claims, 12 Drawing Sheets

Specification includes a Sequence Listing.

(56) References Cited

OTHER PUBLICATIONS

Carter, P., "Improving the Efficacy of Antibody-Based Cancer Therapies," *Nature Reviews* 1:118-129, Macmillan Magazines Ltd, England (2001).

Daniel, C., et al., "Mapping of Linear Antigenic Sites on the S Glycoprotein of a Neurotropic Murine Coronavirus with Synthetic Peptides: A Combination of Nine Prediction Algorithms Fails to Identify Relevant Epitopes and Peptide Immunogenicity Is Drastically Influenced by the Nature of the Protein Carrier," *Virology* 202:540-548, Academic Press, Inc., United States (1994).

George, J., et al., "Differential Effects of Anti-β32-Glycoprotein I Antibodies on Endothelial Cells and on the Manifestations of Experimental Antiphospholipid Syndrome," *Circulation* 97:900-906, American Heart Association, Inc., United States (1998).

Giusti, A.M., et aL, "Somatic diversification of S107 from an antiphosphocholine to an anti-DNA autoantibody is due to a single base change in its heavy chain variable region," *Proc Nall Acad Sci USA* 84:2926-2930, National Academy of Sciences, United States (1987).

Greenspan, N.S. and Di Cera, E., "Defining epitopes: It's not as easy as it seems," *Nature Biotechnology* 17:836-837, Nature America Inc., United States (1999).

Gussow, D. and Seemann, G., "Humanization of Monoclonal Antibodies," *Methods in Enzymology* 203:99-121, Academic Press, Inc., United States (1991).

Malyankar, U.M. and Macdougall, J.R., "Genome-Scale Analysis of Lung Cancer Progression," *Am J Pharmacogenomics* 4(3):169-176, Adis International, New Zealand (2004).

Mariuzza, R.A., et al., "The Structural Basis of Antigen-Antibody Recognition," *Ann Rev Biophys Biophys Chem* 16:139-159, Annual Reviews Inc., United States (1987).

Morris, G.E., "Epitope Mapping of Protein Antigens by Competition ELISA," in *The Protein Protocols Handbook*, pp. 595-600, Walker J.M., ed., Humana Press Inc., United States (1996).

Perez De La Lastra, J.M., et al., "Epitope mapping of 10 monoclonal antibodies against the pig analogue of human membrane cofactor protein (MCP)," *Immunology* 96:663-670, Blackwell Science Ltd., England (1999).

Rudikoff, S., et al., "Single amino acid substitution altering antigen-binding specificity," *Proc Nat Acad Sci USA* 79:1979-1983, National Academy of Sciences, United States (1982).

Winkler, K., et al., "Changing the Antigen Binding Specificity by Single Point Mutations of an Anti-p24 (HIV-1) Antibody," *Journal of Immunology* 165:4505-4514, American Association of Immunologists, United States (2000).

Xi, L., et al., "A Combination of Molecular Markers Accurately Detects Lymph Node Metastasis in Non-Small Cell Lung Cancer Patients," *Clin Cancer Res* 12(8):2484-2491, American Association for Cancer Research, United States (2006).

Amagai, M., et al., "Autoantibodies against a Novel Epithelial Cadherin in Pemphigus Vulgaris, a Disease of Cell Adhesion," *Cell* 67:869-877, Cell Press (1991).

Brakenhoff, R.H., et al., "The Human E48 Antigen, Highly Homologous to the Murine Ly-6 Antigen ThB, Is a GPI-anchored Molecule Apparently Involved in Keratinocyte Cell-Cell Adhesion," *J. Cell Biol.* 129:1677-1689, The Rockefeller University Press (1995).

Ishii, K., et al., "In Vitro Keratinocyte Dissociation Assay for Evaluation of the Pathogenicity of Anti-Desmoglein 3 IgG Autoantibodies in Pemphigus Vulgaris," *J. Invest. Dermatol.* 124:939-946, The Society for Investigative Dermatology, Inc. (2005).

Krunic, A.L.J., et al., "Differential Expression of Desmosomal Glycoproteins in Keratoacanthoma and Squamous Cell Carcinoma of the Skin: An Immunohistochemical Aid to Diagnosis," *Acta. Deem. Venereol. (Stockh)* 76:394-398, Scandinavian University Press (1996).

Krunic, A.L., et al., "Desmoglein in multiple self-healing squamous epithelioma of Ferguson-Smith-comparison of staining patterns with actinic keratoacanthoma and squamous cell carcinoma of the skin," *Arch. Dermatol. Res.* 290: 319-324, Springer-Verlag (1998).

Stanley, J.R., et al., "Pemphigus Antibodies Identify a Cell Surface Glycoprotein Synthesized by Human and Mouse Keratinocytes," *J. Clin. Invest.* 70:281-288, American Society for Clinical Investigation (1982).

Tsunoda, K., et al., "Induction of Pemphigus Phenotype by a Mouse Monoclonal Antibody Against the Amino-Terminal Adhesive Interface of Desmoglein 3," *J. Immunol.* 170:2170-2178, The American Association of Immunologists, Inc. (2003).

Wada, N., et al., "Expression of desmoglein 3 in medullary thymic epithelial cells in thymus," *J. Invest. Dermatol.* 124(4 Suppl): p. A9, 054, The Society for Investigative Dermatology, Inc. (2005).

Wahl III, J.K. "Generation of Monoclonal Antibodies Specific for Desmoglein Family Members," *Hybridoma and Hybridomics* 21:37-44, Mary Ann Liebert, Inc. (2002).

Xi, L., et al., "A Combination of Molecular Markers Accurately Detects Lymph Node Metastasis in Non-Small Cell Lung Cancer Patients," *Clin. Cancer Res.* 12:2484-2491, American Association for Cancer Research (2006).

Yamamoto, Y., et al., "Anti-desmoglein3 (Dsg3) monoclonal antibodies deplete Dsg3 from desmosomes in cultured keratinocytes and their activities differ in sites of epitopes," *J. Invest. Dermatol.* 124(4 Suppl): p. A31 186, The Society for Investigative Dermatology, Inc. (2005).

International Search Report for International Application No. PCT/JP2007/065834, Japanese Patent Office, dated Dec. 4, 2007.

Chen, G., et al., "Discordant Protein and mRNA Expression in Lung Adenocarcinomas," *Mol. Cell. Proteomics* 1:304-313, The American Society for Biochemistry and Molecular Biology, Inc., United States (2002).

Chung, M.C.M., et al., "Proteomics of Hepatocellular Carcinoma: Present Status and Future Prospects," in *Proteomics: Biomedical and Pharmaceutical Applications* 163-181 (Hondermarck, H., ed., 2004).

Iizuka, N., et al., "DNA Microarray Study of Hepatocellular Carcinoma," *Saishin Igaku* 59:1263-1270, Japan (2004).

Unverified English language translation of Iizuka, N., et al., "DNA Microarray Study of Hepatocellular Carcinoma," *Saishin Igaku* 59:1263-1270, Japan (2004).

Communication under Rule 71(3) EPC—Intention to grant in European Patent Application 16 178 652.0 dated Jul. 24, 2018.

DIAGNOSIS AND TREATMENT OF CANCER USING ANTI-DESMOGLEIN-3 ANTIBODIES

REFERENCE TO SEQUENCE LISTING SUBMITTED ELECTRONICALLY

The content of the electronically submitted sequence listing (Name 21440390001_sequencelisting.txt; Size: 6.06 kilobytes; and Date of Creation: Feb. 7, 2017) filed with the application is incorporated herein by reference in its entirety.

TECHNICAL FIELD

The present invention relates to methods for diagnosing and treating cancer, cell proliferation inhibitors, and anti-cancer agents.

BACKGROUND ART

Desmoglein 3 (hereinafter referred to as DSG3) was first identified as a glycoprotein having a molecular weight of 130 kDa by immunoprecipitation of keratinocyte extracts with an autoantibody obtained from the serum of patients affected by pemphigus vulgaris (hereinafter referred to as PV), which is an autoimmune blister-forming disease of the skin and mucosa, and was named the PV antigen (hereinafter referred to as PVA) (Non-patent Document 1 and J. Clin. Invest. 74, 313-320, 1984). Then, antibody molecules that react with the above-mentioned 130-kDa protein were isolated from the serum of PV patients by affinity purification. Next, an expression library was constructed using poly(A) RNA isolated from human keratinocytes and was screened using the isolated antibodies, and a cDNA encoding PVA was isolated. Based on analysis of the nucleotide sequence of the isolated cDNA, the PVA molecule was found to be highly homologous to the sequences of a group of molecules belonging to the cadherin gene superfamily which encodes intercellular adhesion factors (Non-patent Document 2).

Cadherin molecules are expressed in a wide variety of tissues and they are involved in cell adhesion in vivo. Within the cadherin group, a group of molecules are expressed in desmosomes, which are adhesion sites between cells on the cell membrane, and are called desmosomal cadherins or desmogleins. Keratinocytes, which were used for isolation and cloning of the DSG3 molecule (a member of the desmoglein family), are cells that occupy a large portion of the epidermis. They are tightly adhered to adjacent cells via desmosomes and the DSG3 molecule is considered to be involved in this adhesion. Anti-DSG3 autoantibodies present in PV patients' sera are thought to cause PV lesions by binding to the DSG3 molecule and inhibiting intercellular adhesion mediated by the DSG3 molecule.

As described above, PV lesions are induced by polyclonal anti-DSG3 autoantibodies present in PV patients' sera. Monoclonal anti-DSG3 antibodies that have the ability to induce PV-like lesions upon transplantation of hybridomas into mice have also been isolated (Non-patent Document 3), and they have been shown to have a cell-dissociating activity that inhibits cell adhesion of keratinocytes in the test tube as well (Non-patent Document 4). As described above, the cell-dissociating activity of anti-DSG3 antibodies observed in the test tube has been suggested to be the activity that induces PV lesions in vivo.

As described above, it is known that the DSG3 protein has an important function in keratinocyte adhesion, and that anti-DSG3 antibodies are involved in the development of PV lesions. However, involvement of the DSG3 protein in other diseases, or functions of anti-DSG3 antibodies other than the cell-dissociating activity have not been elucidated. In particular, connection of the DSG3 molecule with the development of cancer, especially lung cancer, and proliferation, invasion, metastasis, or transformation of lung cancer cells in mammals, in particular, humans, has not been elucidated.

Of the various types of cancers, lung cancer has the highest mortality rate in both men and women. The mortality rate of lung cancer in Japan has increased after 1950; as a result, the number of lung cancer deaths in 1998 was 50,871 individuals, which was approximately 18% of all malignant tumor deaths, and after 1993, the number of deaths has exceeded that of stomach cancer and is ranked number one among malignant tumors for men (Health and Welfare Statistics Association, Kokumin eisei no doko/kousei no shihyou (Trends of national health/indicators of welfare), 47, 52-53, 2000). Furthermore, on a global scale, approximately 3,000,000 people a year are dying of lung cancer. Basic histological types of lung cancer include adenocarcinoma, squamous cell carcinoma, adenosquamous carcinoma, large cell carcinoma, and small cell carcinoma. Since the former four do not show large differences in prognosis or therapeutic strategy, they are collectively referred to as non-small cell lung cancer.

The number of non-small cell lung cancer cases accounts for 80% to 85% of the total number of lung cancer cases. Examples of the characteristics of non-small cell lung cancer are slow progression compared to small-cell cancers, and insufficient response to chemotherapy and radiation therapy. Therefore, when the tumor is localized, surgical resection is the number one choice, but the treatment outcome is very poor compared to other carcinomas such as stomach cancer at the same disease stage by TNM classification. While recent attempts have been actively pursued to improve the outcome by multimodal treatment, effective therapeutic methods that lead to complete remission have not been established. In non-small cell lung cancer, surgical therapy is considered for up to stage Ma, while in subsequent clinical disease stages, surgery is rarely applied, and chemotherapy and radiation therapy are the main therapies. SCC (squamous cell carcinoma related antigen), Cyfra (cytokeratin 19 fragment), CEA (carcinoembryonic antigen), and SLX (sialyl Lewis x-i antigen) are selected as markers for serodiagnosis, and they are used separately or in combination, but the positive rate for early stage cancers is still low, and development of diagnostic markers that will assure early-stage diagnosis of non-small cell lung cancer by serodiagnosis is anticipated (Shuyo maka no yomikata no jissai; haigan (Practical method for reading tumor markers; lung cancer) Rinsho to Kenkyu (Clinic and Research) 78, 35-40, 2001).

Small cell lung cancer tumors constitute approximately 15% to 20% of all lung cancers in Japan, and their speed of proliferation is fast compared to other lung cancers, but they are highly sensitive to anticancer agents and radiation therapy, and have significantly different clinical characteristics from those of adenocarcinoma, squamous cell carcinoma, large cell carcinoma, and such. For small cell cancer, surgical therapy is considered only in stage Ia (tumor diameter is 20 mm or less, and no invasion or metastasis to lymph nodes and nearby organs is shown), and chemotherapy and radiation therapy are basically the main therapeutic methods employed. As diagnostic markers, NSE (neuron-specific enolase) and proGRP (pro gastrin-releasing peptide) are used as tumor markers with relatively high specificity to small cell cancer, and their positive rates are reported to be approximately 60% and 70%, respectively.

Although there are still no examples of application in clinical practice for lung cancers, the therapeutic response rate in breast cancer, lymphoma, and such is increasing, because targeted therapy using monoclonal antibodies against cancer-specific tumor antigens exhibits a mode of action different from conventional therapy which uses chemotherapeutic agents. In targeted therapy that uses the above-mentioned antibody pharmaceuticals, when the antibodies are functional and effective, their activities include: antibody-dependent cell-mediated cytotoxicity (ADCC) activity via effector cells; complement-dependent cytotoxicity (CDC) activity via complements; and cytotoxic activity as a result of construction of conjugate molecules with chemotherapeutic agents, toxic peptides, or radioactive chemical substances. Additional activities besides those mentioned above include, for example, agonistic activity in which the antibody itself catalyzes an agonistic effect on the antigenic molecule; and neutralizing activity that blocks signals for cell activation, proliferation, or the like. In order to apply molecular-targeting therapy that uses antibodies exhibiting activities such as those mentioned above in the treatment of lung cancer, which has low positive rate of diagnosis, low disease cure rate, and still has room for complete remission, identification of tumor-specific molecules expressed in lung cancer cells and production of antibodies that exhibit desirable activity by targeting such molecules are strongly anticipated.

Prior art literature information relating to the present invention is the following:
[Patent Document 1] WO 99/57149.
[Patent Document 2] WO 02/86443.
[Patent Document 3] WO 03/20769.
[Non-patent Document 1] J. Clin. Invest. 70, 281-288, 1982.
[Non-patent Document 2] Cell 67, 869-877, 1991.
[Non-patent Document 3] J. Immunology 170, 2170-2178, 2003.
[Non-patent Document 4] J. Invest. Dermatol., 124, 939-946, 2005.

DISCLOSURE OF THE INVENTION

Problems to be Solved by the Invention

An objective of the present invention is to provide anti-DSG3 antibodies and uses thereof. More specifically, an objective of the present invention is to provide novel methods for diagnosing and treating cancer using anti-DSG3 antibodies, novel cell proliferation inhibitors and anticancer agents comprising anti-DSG3 antibodies, and novel anti-DSG3 antibodies.

Means for Solving the Problems

The present inventors discovered that DSG3 is highly expressed in cancer cells such as lung cancer cells. Furthermore, when complement-dependent cytotoxicity (CDC) activity and antibody-dependent cellular cytotoxicity (ADCC) activity of anti-DSG3 antibodies were measured, the anti-DSG3 antibodies were found to have CDC activity and ADCC activity towards DSG3-expressing cells. Furthermore, from the above-mentioned findings, the present inventors discovered that the anti-DSG3 antibodies were effective for diagnosing, preventing, and treating cancers in which the DSG3 expression is elevated, including lung cancer, and thereby completed the present invention.

The present invention provides pharmaceutical compositions comprising a DSG3 protein-binding antibody as an active ingredient. The present invention also provides cell proliferation inhibitors comprising a DSG3 protein-binding antibody as an active ingredient. The present invention further provides anticancer agents comprising a DSG3 protein-binding antibody as an active ingredient. Preferably, the DSG3 protein-binding antibody has cytotoxic activity. Preferably, the cancer is lung cancer. More preferably, the cancer is non-small cell lung cancer.

In another embodiment, the present invention provides methods for inducing cell injury towards cells that express the DSG3 protein by contacting DSG3-expressing cells with a DSG3 protein-binding antibody. The present invention also provides methods for suppressing proliferation of cells that express a DSG3 protein by contacting cells that express the DSG3 protein with a DSG3 protein-binding antibody. The DSG3 protein-binding antibody preferably has cytotoxic activity. Cells that express a DSG3 protein are preferably cancer cells.

Furthermore, in another embodiment, the present invention provides antibodies that bind to a DSG3 protein and have cytotoxic activity towards cells that express the DSG3 protein. Preferably, the cytotoxic activity is ADCC activity. Preferably, the cytotoxic activity is CDC activity. The present invention also provides antibodies to which a low-molecular-weight chemotherapeutic agent or a toxic peptide is bound, or antibodies having cytotoxic activity to which a low-molecular-weight chemotherapeutic agent or a toxic peptide is bound.

The present invention further provides antibodies that bind to a DSG3 protein, and have cytotoxic activity but not cell-dissociating activity towards cells expressing the DSG3 protein.

In another embodiment, the present invention provides uses of the DSG3 protein as a cancer diagnostic marker.

Furthermore, in another embodiment, the present invention provides methods for diagnosing cancer, which comprise detecting a DSG3 protein using an antibody that binds to the DSG3 protein. In the methods of the present invention, preferably the extracellular region of the DSG3 protein is detected. Preferably, the methods of the present invention are carried out using an antibody that recognizes the DSG3 protein. Preferably, the methods of the present invention detect the DSG3 protein in the blood, serum, or plasma, or DSG3 protein isolated from cells.

In another embodiment, the present invention provides methods for diagnosing cancer which comprise the steps of:
(a) collecting a sample from a subject; and
(b) using a DSG3 protein-binding antibody to detect the DSG3 protein contained in the collected sample.
In the present invention, any substance can be used as the above-mentioned sample so long as it can be collected from the subject. Serum collected from a subject is used in one embodiment, and a biopsy sample collected from a subject is used in another embodiment. In the methods of diagnosis, the cancer may be any cancer so long as the subject cancer cells express a DSG3 protein, but it is preferably lung cancer, and more preferably non-small cell lung cancer. In the present invention, the step of collecting a sample from a subject can also be expressed as the step of providing a sample collected from a subject.

Furthermore, in another embodiment, the present invention provides methods for diagnosing cancer, in which the DSG3 protein-binding antibody is labeled with a nuclide selected from any one of 11C, 13N, 15O, 18F, 45Ti, 55Co, 64Cu, 66Ga, 68Ga, 76Br, 89Zr, and 124I.

Furthermore, in another embodiment, the present invention provides methods for diagnosing cancer, in which the expression of a gene encoding the DSG3 protein is detected.

Furthermore, in another embodiment, the present invention provides diagnostic agents and kits to be used in the methods of diagnosis of the present invention Thus, the present application provides the following:

[1] a pharmaceutical composition comprising as an active ingredient an antibody that binds to a DSG3 protein;

[2] a cell growth inhibitor comprising as an active ingredient an antibody that binds to a DSG3 protein;

[3] an anticancer agent comprising as an active ingredient an antibody that binds to a DSG3 protein;

[4] the anticancer agent of [3], wherein the antibody that binds to a DSG3 protein is an antibody that has cytotoxic activity;

[5] the anticancer agent of [3] or [4], wherein the antibody that binds to a DSG3 protein is an antibody described in any of (1) to (47) below:

(1) an antibody comprising an H chain having the amino acid sequence of SEQ ID NO: 2 as CDR1, the amino acid sequence of SEQ ID NO: 4 as CDR2, and the amino acid sequence of SEQ ID NO: 6 as CDR3;

(2) an antibody comprising the H chain of (1), wherein the H chain has the amino acid sequence of SEQ ID NO: 8 as CH;

(3) an antibody comprising the H chain of (1), wherein the H chain has the amino acid sequence of SEQ ID NO: 10 as CH;

(4) an antibody comprising an L chain having the amino acid sequence of SEQ ID NO: 12 as CDR1, the amino acid sequence of SEQ ID NO: 14 as CDR2, and the amino acid sequence of SEQ ID NO: 16 as CDR3;

(5) an antibody comprising the L chain of (4), wherein the L chain has the amino acid sequence of SEQ ID NO: 18 as CL;

(6) an antibody comprising the L chain of (4), wherein the L chain has the amino acid sequence of SEQ ID NO: 20 as CL;

(7) an antibody comprising the H chain of (1) and the L chain of (4);

(8) an antibody comprising the H chain of (2) and the L chain of (5);

(9) an antibody comprising the H chain of (3) and the L chain of (6);

(10) an antibody comprising an H chain having the amino acid sequence of SEQ ID NO: 22 as CDR1, the amino acid sequence of SEQ ID NO: 24 as CDR2, and the amino acid sequence of SEQ ID NO: 26 as CDR3;

(11) an antibody comprising the H chain of (10), wherein the H chain has the amino acid sequence of SEQ ID NO: 28 as CH;

(12) an antibody comprising the H chain of (10), wherein the H chain has the amino acid sequence of SEQ ID NO: 10 as CH;

(13) an antibody comprising an L chain having the amino acid sequence of SEQ ID NO: 30 as CDR1, the amino acid sequence of SEQ ID NO: 32 as CDR2, and the amino acid sequence of SEQ ID NO: 34 as CDR3;

(14) an antibody comprising the L chain of (13), wherein the L chain has the amino acid sequence of SEQ ID NO: 36 as CL;

(15) an antibody comprising the L chain of (13), wherein the L chain has the amino acid sequence of SEQ ID NO: 20 as CL;

(16) an antibody comprising the H chain of (10) and the L chain of (13);

(17) an antibody comprising the H chain of (11) and the L chain of (14);

(18) an antibody comprising the H chain of (12) and the L chain of (15);

(19) an antibody comprising the H chain of (1) and the L chain of (13);

(20) an antibody comprising the H chain of (2) and the L chain of (14);

(21) an antibody comprising the H chain of (3) and the L chain of (15);

(22) an antibody comprising the H chain of (10) and the L chain of (4);

(23) an antibody comprising the H chain of (11) and the L chain of (5);

(24) an antibody comprising the H chain of (12) and the L chain of (6);

(25) an antibody comprising an H chain having the amino acid sequence of SEQ ID NO: 81 as CDR1, the amino acid sequence of SEQ ID NO: 83 as CDR2, and the amino acid sequence of SEQ ID NO: 85 as CDR3;

(26) an antibody comprising the H chain of (25), wherein the H chain has the amino acid sequence of SEQ ID NO: 28 as CH;

(27) an antibody comprising the H chain of (25), wherein the H chain has the amino acid sequence of SEQ ID NO: 10 as CH;

(28) an antibody comprising an L chain having the amino acid sequence of SEQ ID NO: 87 as CDR1, the amino acid sequence of SEQ ID NO: 89 as CDR2, and the amino acid sequence of SEQ ID NO: 91 as CDR3;

(29) an antibody comprising the L chain of (28), wherein the L chain has the amino acid sequence of SEQ ID NO: 36 as CL;

(30) an antibody comprising the L chain of (28), wherein the L chain has the amino acid sequence of SEQ ID NO: 20 as CL;

(31) an antibody comprising the H chain of (25) and the L chain of (28);

(32) an antibody comprising the H chain of (26) and the L chain of (29);

(33) an antibody comprising the H chain of (27) and the L chain of (30);

(34) an antibody comprising the H chain of (1) and the L chain of (28);

(35) an antibody comprising the H chain of (2) and the L chain of (29);

(36) an antibody comprising the H chain of (3) and the L chain of (30);

(37) an antibody comprising the H chain of (10) and the L chain of (28);

(38) an antibody comprising the H chain of (11) and the L chain of (29);

(39) an antibody comprising the H chain of (12) and the L chain of (30);

(40) an antibody comprising the H chain of (25) and the L chain of (4);

(41) an antibody comprising the H chain of (26) and the L chain of (5);

(42) an antibody comprising the H chain of (27) and the L chain of (6);

(43) an antibody comprising the H chain of (25) and the L chain of (13);

(44) an antibody comprising the H chain of (26) and the L chain of (14);

(45) an antibody comprising the H chain of (27) and the L chain of (15);

(46) an antibody comprising one or more amino acid substitutions, deletions, additions, and/or insertions in the antibody of any of (1) to (45), which has equivalent activity as the antibody of any of (1) to (45); and

(47) an antibody that binds to the same DSG3 protein epitope as the antibody of any of (1) to (45);

[6] the anticancer agent of any one of [3] to [5], wherein the cancer is lung cancer, colon cancer, esophageal cancer, stomach cancer, pancreatic cancer, skin cancer, or uterine cancer;

[7] the anticancer agent of [6], wherein the lung cancer is non-small-cell lung cancer;

[8] a method of inducing cell damage in DSG3-expressing cells by contacting cells that express a DSG3 protein with an antibody that binds to the DSG3 protein;

[9] a method of suppressing growth of DSG3-expressing cells by contacting cells that express a DSG3 protein with an antibody that binds to the DSG3 protein;

[10] the method of [8] or [9], wherein the DSG3 protein-binding antibody has cytotoxic activity;

[11] the method of any one of [8] to [10], wherein the DSG3 protein-binding antibody is an antibody of any of (1) to (47) below:

(1) an antibody comprising an H chain having the amino acid sequence of SEQ ID NO: 2 as CDR1, the amino acid sequence of SEQ ID NO: 4 as CDR2, and the amino acid sequence of SEQ ID NO: 6 as CDR3;

(2) an antibody comprising the H chain of (1), wherein the H chain has the amino acid sequence of SEQ ID NO: 8 as CH;

(3) an antibody comprising the H chain of (1), wherein the H chain has the amino acid sequence of SEQ ID NO: 10 as CH;

(4) an antibody comprising an L chain having the amino acid sequence of SEQ ID NO: 12 as CDR1, the amino acid sequence of SEQ ID NO: 14 as CDR2, and the amino acid sequence of SEQ ID NO: 16 as CDR3;

(5) an antibody comprising the L chain of (4), wherein the L chain has the amino acid sequence of SEQ ID NO: 18 as CL;

(6) an antibody comprising the L chain of (4), wherein the L chain has the amino acid sequence of SEQ ID NO: 20 as CL;

(7) an antibody comprising the H chain of (1) and the L chain of (4);

(8) an antibody comprising the H chain of (2) and the L chain of (5);

(9) an antibody comprising the H chain of (3) and the L chain of (6);

(10) an antibody comprising an H chain having the amino acid sequence of SEQ ID NO: 22 as CDR1, the amino acid sequence of SEQ ID NO: 24 as CDR2, and the amino acid sequence of SEQ ID NO: 26 as CDR3;

(11) an antibody comprising the H chain of (10) having the amino acid sequence of SEQ ID NO: 28 as CH;

(12) an antibody comprising the H chain of (10) having the amino acid sequence of SEQ ID NO: 10 as CH;

(13) an antibody comprising an L chain having the amino acid sequence of SEQ ID NO: 30 as CDR1, the amino acid sequence of SEQ ID NO: 32 as CDR2, and the amino acid sequence of SEQ ID NO: 34 as CDR3;

(14) an antibody comprising the L chain of (13), wherein the L chain has the amino acid sequence of SEQ ID NO: 36 as CL;

(15) an antibody comprising the L chain of (13), wherein the L chain has the amino acid sequence of SEQ ID NO: 20 as CL;

(16) an antibody comprising the H chain of (10) and the L chain of (13);

(17) an antibody comprising the H chain of (11) and the L chain of (14);

(18) an antibody comprising the H chain of (12) and the L chain of (15);

(19) an antibody comprising the H chain of (1) and the L chain of (13);

(20) an antibody comprising the H chain of (2) and the L chain of (14);

(21) an antibody comprising the H chain of (3) and the L chain of (15);

(22) an antibody comprising the H chain of (10) and the L chain of (4);

(23) an antibody comprising the H chain of (11) and the L chain of (5);

(24) an antibody comprising the H chain of (12) and the L chain of (6);

(25) an antibody comprising an H chain having the amino acid sequence of SEQ ID NO: 81 as CDR1, the amino acid sequence of SEQ ID NO: 83 as CDR2, and the amino acid sequence of SEQ ID NO: 85 as CDR3;

(26) an antibody comprising the H chain of (25), wherein the H chain has the amino acid sequence of SEQ ID NO: 28 as CH;

(27) an antibody comprising the H chain of (25), wherein the H chain has the amino acid sequence of SEQ ID NO: 10 as CH;

(28) an antibody comprising an L chain having the amino acid sequence of SEQ ID NO: 87 as CDR1, the amino acid sequence of SEQ ID NO: 89 as CDR2, and the amino acid sequence of SEQ ID NO: 91 as CDR3;

(29) an antibody comprising the L chain of (28), wherein the L chain has the amino acid sequence of SEQ ID NO: 36 as CL;

(30) an antibody comprising the L chain of (28), wherein the L chain has the amino acid sequence of SEQ ID NO: 20 as CL;

(31) an antibody comprising the H chain of (25) and the L chain of (28);

(32) an antibody comprising the H chain of (26) and the L chain of (29);

(33) an antibody comprising the H chain of (27) and the L chain of (30);

(34) an antibody comprising the H chain of (1) and the L chain of (28);

(35) an antibody comprising the H chain of (2) and the L chain of (29);

(36) an antibody comprising the H chain of (3) and the L chain of (30);

(37) an antibody comprising the H chain of (10) and the L chain of (28);

(38) an antibody comprising the H chain of (11) and the L chain of (29);

(39) an antibody comprising the H chain of (12) and the L chain of (30);

(40) an antibody comprising the H chain of (25) and the L chain of (4);

(41) an antibody comprising the H chain of (26) and the L chain of (5);

(42) an antibody comprising the H chain of (27) and the L chain of (6);

(43) an antibody comprising the H chain of (25) and the L chain of (13);

(44) an antibody comprising the H chain of (26) and the L chain of (14);

(45) an antibody comprising the H chain of (27) and the L chain of (15);

(46) an antibody comprising one or more amino acid substitutions, deletions, additions, and/or insertions in the antibody of any of (1) to (45), which has equivalent activity as the antibody of any of (1) to (45); and

(47) an antibody that binds to the same DSG3 protein epitope as the antibody of any of (1) to (45);

[12] the method of any one of [8] to [11], wherein the cells that express a DSG3 protein are cancer cells;

[13] an antibody that binds to a DSG3 protein and has cytotoxic activity against cells that express a DSG3 protein;

[14] the antibody of [13], wherein the cytotoxic activity is ADCC activity;

[15] the antibody of [13], wherein the cytotoxic activity is CDC activity;

[16] the antibody of any one of [13] to [15], wherein a low-molecular-weight chemotherapeutic agent or a toxic peptide is bound to the antibody;

[17] an antibody binding to a DSG3 protein, wherein a low-molecular-weight chemotherapeutic agent or a toxic peptide is bound to the antibody;

[18] the antibody of any one of [13] to [17], wherein the antibody is an antibody of any of (1) to (47) below:

(1) an antibody comprising an H chain having the amino acid sequence of SEQ ID NO: 2 as CDR1, the amino acid sequence of SEQ ID NO: 4 as CDR2, and the amino acid sequence of SEQ ID NO: 6 as CDR3;

(2) an antibody comprising the H chain of (1), wherein the H chain has the amino acid sequence of SEQ ID NO: 8 as CH;

(3) an antibody comprising the H chain of (1), wherein the H chain has the amino acid sequence of SEQ ID NO: 10 as CH;

(4) an antibody comprising an L chain having the amino acid sequence of SEQ ID NO: 12 as CDR1, the amino acid sequence of SEQ ID NO: 14 as CDR2, and the amino acid sequence of SEQ ID NO: 16 as CDR3;

(5) an antibody comprising the L chain of (4) having the amino acid sequence of SEQ ID NO: 18 as CL;

(6) an antibody comprising the L chain of (4) having the amino acid sequence of SEQ ID NO: 20 as CL;

(7) an antibody comprising the H chain of (1) and the L chain of (4);

(8) an antibody comprising the H chain of (2) and the L chain of (5);

(9) an antibody comprising the H chain of (3) and the L chain of (6);

(10) an antibody comprising an H chain having the amino acid sequence of SEQ ID NO: 22 as CDR1, the amino acid sequence of SEQ ID NO: 24 as CDR2, and the amino acid sequence of SEQ ID NO: 26 as CDR3;

(11) an antibody comprising the H chain of (10), wherein the H chain has the amino acid sequence of SEQ ID NO: 28 as CH;

(12) an antibody comprising the H chain of (10), wherein the H chain has the amino acid sequence of SEQ ID NO: 10 as CH;

(13) an antibody comprising an L chain having the amino acid sequence of SEQ ID NO: 30 as CDR1, the amino acid sequence of SEQ ID NO: 32 as CDR2, and the amino acid sequence of SEQ ID NO: 34 as CDR3;

(14) an antibody comprising the L chain of (13), wherein the L chain has the amino acid sequence of SEQ ID NO: 36 as CL;

(15) an antibody comprising the L chain of (13), wherein the L chain has the amino acid sequence of SEQ ID NO: 20 as CL;

(16) an antibody comprising the H chain of (10) and the L chain of (13);

(17) an antibody comprising the H chain of (11) and the L chain of (14);

(18) an antibody comprising the H chain of (12) and the L chain of (15);

(19) an antibody comprising the H chain of (1) and the L chain of (13);

(20) an antibody comprising the H chain of (2) and the L chain of (14);

(21) an antibody comprising the H chain of (3) and the L chain of (15);

(22) an antibody comprising the H chain of (10) and the L chain of (4);

(23) an antibody comprising the H chain of (11) and the L chain of (5);

(24) an antibody comprising the H chain of (12) and the L chain of (6);

(25) an antibody comprising an H chain having the amino acid sequence of SEQ ID NO: 81 as CDR1, the amino acid sequence of SEQ ID NO: 83 as CDR2, and the amino acid sequence of SEQ ID NO: 85 as CDR3;

(26) an antibody comprising the H chain of (25), wherein the H chain has the amino acid sequence of SEQ ID NO: 28 as CH;

(27) an antibody comprising the H chain of (25), wherein the H chain has the amino acid sequence of SEQ ID NO: 10 as CH;

(28) an antibody comprising an L chain having the amino acid sequence of SEQ ID NO: 87 as CDR1, the amino acid sequence of SEQ ID NO: 89 as CDR2, and the amino acid sequence of SEQ ID NO: 91 as CDR3;

(29) an antibody comprising the L chain of (28), wherein the L chain has the amino acid sequence of SEQ ID NO: 36 as CL;

(30) an antibody comprising the L chain of (28), wherein the L chain has the amino acid sequence of SEQ ID NO: 20 as CL;

(31) an antibody comprising the H chain of (25) and the L chain of (28);

(32) an antibody comprising the H chain of (26) and the L chain of (29);

(33) an antibody comprising the H chain of (27) and the L chain of (30);

(34) an antibody comprising the H chain of (1) and the L chain of (28);

(35) an antibody comprising the H chain of (2) and the L chain of (29);

(36) an antibody comprising the H chain of (3) and the L chain of (30);

(37) an antibody comprising the H chain of (10) and the L chain of (28);

(38) an antibody comprising the H chain of (11) and the L chain of (29);

(39) an antibody comprising the H chain of (12) and the L chain of (30);

(40) an antibody comprising the H chain of (25) and the L chain of (4);

(41) an antibody comprising the H chain of (26) and the L chain of (5);

(42) an antibody comprising the H chain of (27) and the L chain of (6);

(43) an antibody comprising the H chain of (25) and the L chain of (13);

(44) an antibody comprising the H chain of (26) and the L chain of (14);

(45) an antibody comprising the H chain of (27) and the L chain of (15);

(46) an antibody comprising one or more amino acid substitutions, deletions, additions, and/or insertions in the antibody of any of (1) to (45), which has equivalent activity as the antibody of any of (1) to (45); and

(47) an antibody that binds to the same DSG3 protein epitope as the antibody of any of (1) to (45);

[19] use of a DSG3 protein as a cancer diagnostic marker;

[20] a method of diagnosing cancer, comprising detecting a DSG3 protein using an antibody that binds to the DSG3 protein;

[21] a method of diagnosing cancer, comprising the steps of:
(a) collecting a sample from a subject; and
(b) detecting a DSG3 protein contained in the collected sample using an antibody that binds to the DSG3 protein;

[22] the method of diagnosis of [20] or [21], wherein the DSG3 protein-binding antibody is an antibody labeled with a positron-emitting nuclide;

[23] the method of diagnosis of [22], wherein the positron-emitting nuclide is a nuclide selected from any of 11C, 13N, 15O, 18F, 45Ti, 55Co, 64Cu, 66Ga, 68Ga, 76Br, 89Zr, and 124I;

[24] a method of diagnosing cancer, comprising detecting expression of a gene encoding a DSG3 protein;

[25] the method of diagnosis of any one of [20] to [24], wherein the cancer is lung cancer, colon cancer, esophageal cancer, stomach cancer, pancreatic cancer, skin cancer, or uterine cancer;

[26] the method of diagnosis of [25], wherein the lung cancer is non-small-cell lung cancer;

[27] a diagnostic agent to be used for the diagnostic method of any one of [20] to [26];

[28] a kit to be used for the diagnostic method of any one of [20] to [26];

[29] use of an antibody that binds to a DSG3 protein in the production of a cell growth inhibitor;

[30] use of an antibody that binds to a DSG3 protein in the production of an anticancer agent;

[31] a method of suppressing cell growth, comprising the step of administering to a subject an antibody that binds to a DSG3 protein; and

[32] a method of preventing or treating cancer, comprising the step of administering to a subject an antibody that binds to a DSG3 protein.

BRIEF DESCRIPTION OF THE DRAWINGS

FIG. 7A depicts the result of analysis using bone marrow-derived effector cells, and FIG. 7B shows the result of analysis using mouse spleen-derived effector cells.

BEST MODE FOR CARRYING OUT THE INVENTION

Figure 1:
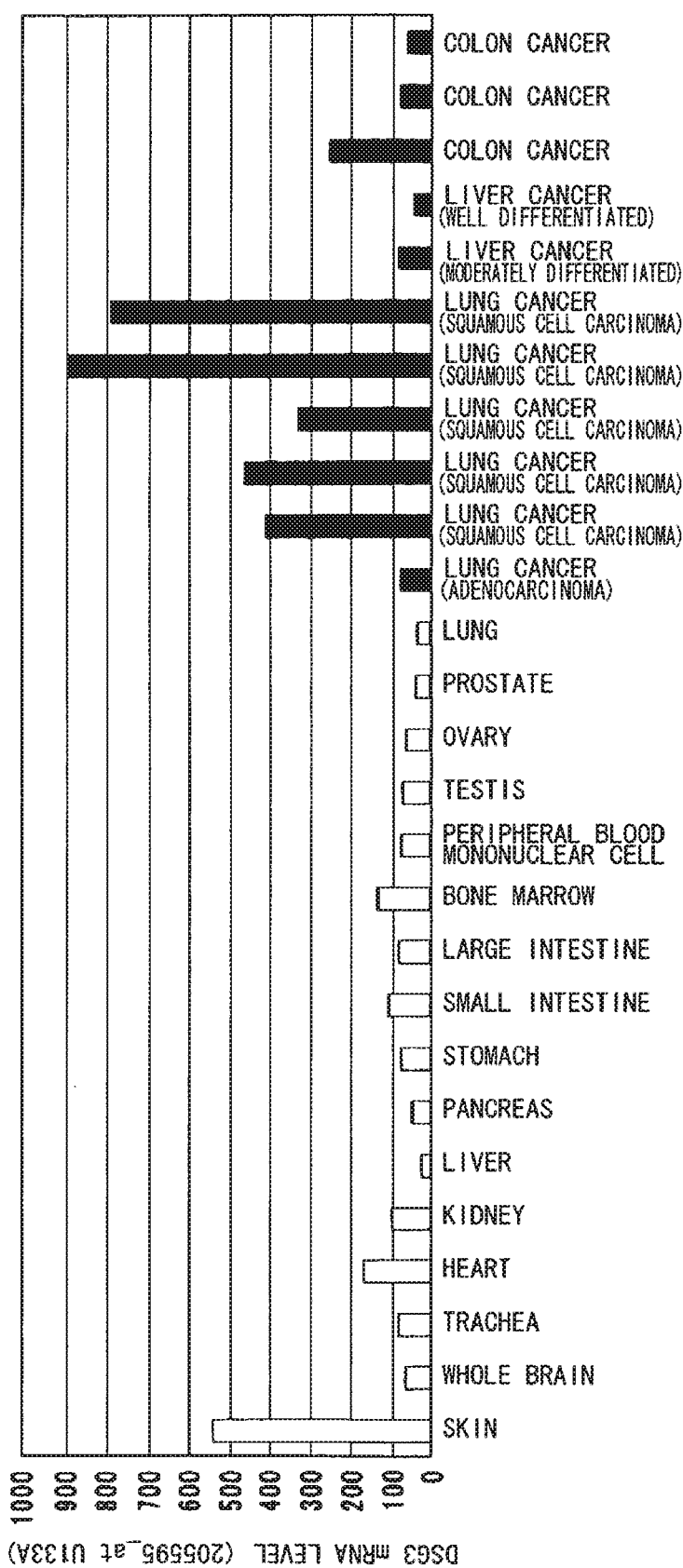
FIG. 1 depicts the result of DSG3 gene expression analysis in normal tissues and cancer tissues using GeneChip U133.

DSG3 (Desmoglein 3) is an axon guidance receptor protein, and its amino acid sequence and its encoding gene sequence are disclosed in GenBank Accession Number NP_001935 (SEQ ID NO: 40) and NM_001944 (SEQ ID NO: 39), respectively. In the present invention, the DSG3 protein refers to both the full-length protein and fragments thereof "Fragments" refers to polypeptides comprising any region of the DSG3 protein, and may not have the function of the naturally-occurring DSG3 protein. Without being limited thereto, an example of the fragments is a fragment comprising the extracellular region of the DSG3 protein. Positions 1 to 616 in the amino acid sequence of SEQ ID NO: 40 correspond to the extracellular region of the DSG3 protein. Positions 617 to 641 in the amino acid sequence of SEQ ID NO: 40 correspond to the transmembrane region.

In the present invention, DSG3 expression was found to be elevated at very high frequency in lung cancer tissues at the gene and protein levels. Furthermore, analyses of clinical samples and cancer cell lines of other cancer types showed that the expression was elevated not only in lung cancer, but also in colon cancer, esophageal cancer, stomach cancer, pancreatic cancer, skin cancer, and uterine cancer. Furthermore, it was shown that immunohistological diagnosis is possible by using DSG3 protein-specific monoclonal antibodies. In other words, the DSG3 protein is useful as a diagnostic marker for cancer.

Detection of DSG3 Gene Expression

Methods of the present invention comprise detecting the DSG3 gene expression. In an embodiment of the methods of the present invention, the DSG3 protein expression is detected.

In the present invention, detection includes quantitative and qualitative detections. Examples of qualitative detection include simple measurement for the presence or absence of the DSG3 protein, measurement to see whether or not the DSG3 protein is present above a certain amount, and measurement that compares the amount of the DSG3 protein with that of other samples (for example, a control sample). On the other hand, examples of quantitative detection include measurement of the DSG3 protein concentration, and measurement of the amount of the DSG3 protein.

Test samples are not particularly limited so long as they are samples that may contain DSG3 protein, and are preferably samples collected from the body of organisms such as mammals, and more preferably samples collected from humans. Specific examples of the test samples include blood, interstitial fluid, plasma, extravascular fluid, cerebrospinal fluid, synovial fluid, pleural fluid, serum, lymphatic fluid, saliva, and urine, but the test samples are preferably blood, serum, or plasma. Test samples of the present invention also include samples obtained from test samples, such as cell culture solutions and specimens of immobilized tissues or cells collected from the body of an organism.

The cancers that are diagnosed are not particularly limited and may be any cancer, but specific examples include lung cancer, colon cancer, esophageal cancer, stomach cancer, pancreatic cancer, skin cancer, and uterine cancer. Lung cancer is preferable and non-small cell lung cancer is particularly preferable.

In the present invention, when a DSG3 protein is detected in a test sample and if the test sample is judged to have a greater amount of the DSG3 protein than a negative control or a healthy individual, it can be determined that the subject has cancer or has a high risk of being affected with cancer in the future.

Subjects in the present invention may be animal species that genetically carry a DSG3 protein, and many non-human mammals such as monkeys, cattle, sheep, mice, dogs, cats, and hamsters are known as such animal species. Subjects that are suitably used are, in particular, humans, but are not limited thereto.

Preferred embodiments of the diagnostic methods of the present invention include diagnostic methods that comprise detecting a DSG3 protein on a section of immobilized tissue or cells obtained from a patient affected with an aforementioned cancer. Furthermore, other embodiments of the present invention include diagnostic methods comprising detecting cell-released DSG3 protein in the blood. In particular, the present invention is preferably a diagnostic method that detects a fragment comprising the extracellular domain of the DSG3 protein present in the blood.

Methods for detecting a DSG3 protein contained in a test sample are not particularly limited, but an immunological method that uses an anti-DSG3 antibody for detection is preferred. The immunological method includes, for example, radioimmunoassay (RIA), enzyme immunoassay (EIA), fluorescence immunoassay (FIA), luminescence immunoassay (LIA), immunoprecipitation (IP), turbidimetric immunoassay (TIA), Western blotting (WB), immunohistochemical staining (IHC), and single radial immunodiffusion (SRID), and is preferably enzyme immunoassay, in particular, enzyme-linked immunosorbent assay (ELISA), for example, sandwich ELISA as an embodiment thereof. The above-mentioned immunological methods such as ELISA can be performed by methods known to those skilled in the art.

The following method is, for example, a common detection method that uses an anti-DSG3 antibody. After immobilizing an anti-DSG3 antibody to a support, the support is blocked with bovine serum albumin (BSA), gelatin, albumin, or such to avoid non-specific binding of proteins to the support. Next, a test sample is added to the support for incubation, and the DSG3 proteins are left to bind to the anti-DSG3 antibody bound to the support. Subsequently, by washing the complex formed between the DSG3 proteins and the anti-DSG3 antibody bound to the support with a washing solution, DSG3 proteins other than those bound to the anti-DSG3 antibody on the support that bound non-specifically to the support are removed. Examples of detection methods that use an anti-DSG3 antibody include methods for detecting a DSG3 protein in a test sample by qualitatively or quantitatively detecting the DSG3 protein bound to the anti-DSG3 antibody on the support, and several specific examples described below.

In the present invention, a support used to immobilize an anti-DSG3 antibody is, for example, insoluble polysaccharides such as agarose and cellulose, synthetic resins such as silicon resin, polystyrene resin, polyacrylamide resin, nylon resin, and polycarbonate resin, and insoluble support such as glass. Such a support is used in the form of beads or plates. In the case of beads, a column or the like filled with beads can be used. In the case of a plate, a multi-well plate (96-well multi-well plate, or such), or a biosensor chip can be used. For binding between an anti-DSG3 antibody and a support, an anti-DSG3 antibody can be bound to a support by generally used methods such as chemical bonding or physical adsorption. Commercially available supports can be used suitably.

Binding between an anti-DSG3 antibody and a DSG3 protein is generally performed in a buffer. For example, phosphate buffer, Tris buffer, citric acid buffer, borate buffer, carbonate buffer, or such is used as the buffer. Furthermore, incubation can be suitably carried out using conditions that are already commonly used, such as incubation at a temperature between 4° C. and room temperature for one hour to 24 hours. So long as the binding between the DSG3 protein and anti-DSG3 antibody is not interrupted, anything can be used for washing after incubation, and for example, a buffer containing a surfactant such as Tween 20 or such can be used suitably.

In the DSG3 protein detection method of the present invention, a control sample can be prepared suitably in addition to the test sample in which the DSG3 protein content will be detected. The control sample includes, for example, a negative control sample containing no DSG3 protein and a positive control sample containing the DSG3 protein. In this case, by comparing the results obtained from a negative control sample containing no DSG3 protein with the results obtained from a positive control sample containing the DSG3 protein, the presence or absence of the DSG3 protein in the test sample can be confirmed. Furthermore, after preparing a series of control samples with stepwise changes in concentration, and obtaining detection results for each control sample as a numerical value, the DSG3 protein contained in a test sample can be quantitatively detected according to a standard curve produced based on the values of the DSG3 protein concentration and their corresponding measured values.

In a preferred embodiment, an example of detection of the DSG3 protein bound to a support via an anti-DSG3 antibody is a method that uses an anti-DSG3 antibody labeled with a labeling substance. For example, the DSG3 protein can be detected by contacting a test sample with the anti-DSG3 antibody immobilized onto a support, washing it, and then using a labeled antibody that specifically recognizes the DSG3 protein bound to the anti-DSG3 antibody.

Anti-DSG3 antibodies can be labeled by generally known methods. A labeling substance known to those skilled in the art such as fluorescent dyes, enzymes, coenzymes, chemiluminescent substances, and radioactive substances can be used as the labeling substance, and specific examples include radioisotopes (32P, 14C, 125I, 3H, 131I, and such), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, micro peroxidase, and biotin. When using biotin as a labeling substance, addition of biotin-labeled antibodies is preferably followed by addition of avidin bound to an enzyme such as alkaline phosphatase. For the binding of labeling substance with an anti-DSG3 antibody, known methods such as the glutaraldehyde method, maleimide method, pyridyl disulfide method, or periodic acid method can be used.

Specifically, an anti-DSG3 antibody is immobilized onto a support by addition of a solution containing the anti-DSG3 antibody to the support such as a plate. After the plate is washed, it is blocked with, for example, bovine serum albumin (BSA), gelatin, albumin, or such to avoid non-specific protein binding. After the plate is washed again, incubation is carried out by adding a test sample to the plate. After incubation, the plate is washed, and the labeled anti-DSG3 antibody is added. After appropriate incubation, the plate is washed, and then the labeled anti-DSG3 antibody that remains on the plate can be detected. Detection can be performed by methods known to those skilled in the art, and for example, when detecting an anti-DSG3 antibody labeled with a radioactive substance, the labeled anti-DSG3 antibody can be detected by liquid scintillation or an RIA method. When detecting an enzyme-labeled anti-DSG3 antibody, addition of substrate to the labeled anti-DSG3 antibody can be followed by detecting the substrate's enzymatic change, such as color development, using a spectrophotometer. Specific examples of a substrate include 2,2-azinobis (3-ethylbenzothiazoline-6-sulfonic acid) diammonium salt (ABTS), 1,2-phenylenediamine (ortho-phenylenediamine), and 3,3',5,5'-tetramethylbenzidine (TMB). When the substrate is a fluorescence emitting substance, enzymatic change of the substrate can be detected using a spectrofluorometer.

In the present invention, a particularly preferred embodiment of the method for detecting the DSG3 protein is, for example, a method that uses a biotin-labeled anti-DSG3 antibody and avidin. Specifically, addition of a solution containing an anti-DSG3 antibody to a support such as a plate enables immobilization of the anti-DSG3 antibody to the plate. After the plate is washed, it is blocked with, for example, BSA to avoid non-specific protein binding. The plate is washed again, and then a test sample is added to the plate. After incubation, the plate is washed, and a biotin-labeled anti-DSG3 antibody is added to the plate. After suitable incubation, the plate is washed, and avidin bound to an enzyme such as alkaline phosphatase or peroxidase is added to the plate. After incubation, the plate is washed, and the DSG3 protein can be detected after addition of a substrate for the avidin-conjugated enzyme, using the substrate's enzymatic change or such as an indicator.

In the present invention, another embodiment of the method for detecting the DSG3 protein includes a method that uses one or more types of primary antibodies that specifically recognize the DSG3 protein, and one or more types of secondary antibodies that specifically recognize the primary antibodies.

For example, after immobilizing an anti-DSG3 antibody to a support such as a plate, the plate is blocked with bovine serum albumin (BSA), gelatin, albumin, or such to prevent non-specific binding of proteins to the support. Then, after adding a test sample to the plate, it is incubated to allow the DSG3 protein to bind to the anti-DSG3 antibody bound to the plate. Thereafter, the plate is washed with a washing solution so that the DSG3 proteins bound to the support by non-specific binding, and not by specific binding to the anti-DSG3 antibody, are removed from the plate. A different type of anti-DSG3 antibody from the antibody bound to the support binds to the DSG3 protein, and then a secondary antibody that can only bind to the anti-DSG3 antibody that binds to the DSG3 protein but not to the support, is made to react with the DSG3-protein/anti-DSG3-antibody complexes. An example is a method that detects the DSG3 protein in a test sample by qualitatively or quantitatively detecting the secondary antibody that binds as a result of the above-mentioned operation. In this case, the secondary antibody can be more suitably labeled with a labeling substance.

In the present invention, another embodiment of the methods for detecting the DSG3 protein is, for example, a detection method that uses aggregation reaction. In this method, the DSG3 protein can be detected using a carrier onto which an anti-DSG3 antibody is adsorbed. Any carrier may be used for adsorbing the antibody, so long as it is insoluble and stable, and does not cause non-specific reactions. For example, latex particles, bentonite, collodion, kaolin, or immobilized sheep erythrocytes can be used, but the use of latex particles is preferred. Latex particles that can be used are, for example, polystyrene latex particles, styrene-butadiene copolymer latex particles, or polyvinyl toluene latex particles, but the use of polystyrene latex particles is preferred. Sensitized particles are mixed with a sample, and this is stirred for a given period of time. Since the degree of particle aggregation becomes larger as the concentration of DSG3 protein in the sample increases, the DSG3 protein can be detected by assessing the degree of aggregation with the naked eye. Furthermore, the DSG3 protein can also be detected by measuring the increase in turbidity caused by aggregation using a spectrophotometer or such.

In the present invention, another embodiment of the methods for detecting the DSG3 protein includes, for example, a method that uses a biosensor utilizing the surface plasmon resonance phenomenon. The use of a biosensor utilizing the surface plasmon resonance phenomenon enables real-time observation of protein-protein interactions as surface plasmon resonance signals without the need of protein labeling. For example, by using a biosensor such as BIAcore (Biacore), binding between the DSG3 protein and an anti-DSG3 antibody can be detected. Specifically, a test sample is contacted with a sensor chip onto which an anti-DSG3 antibody is immobilized, and the DSG3 protein that binds to the anti-DSG3 antibody can be detected as a change in resonance signals.

Anti-DSG3 antibodies can be labeled by general methods using, in addition to the labels mentioned above, positron-emitting nuclides such as 18F, 55Co, 64Cu, 66Ga, 68Ga, 76Br, 89Zr, and 124I (Acta. Oncol. 32, 825-830, 1993). By using PET (positron emission tomography scanner), which is an instrument for non-invasively obtaining data on the in vivo behavior of drugs, after administering an anti-DSG3 antibody labeled with an above-mentioned positron-emitting nuclide to humans or animals, radiation emitted by the radioactive nuclide is measured from outside the body and then converted into a quantitative image by computed tomography methods. By using PET as described above, antigenic molecules that are highly expressed in a particular cancer can be detected without collecting samples from patients. In addition to the above-mentioned nuclides, anti-DSG3 antibodies can be radiolabeled with short-lived RI using positron-emitting nuclides such as 11C, 13N, 15O, 18F, and 45Ti.

At present, the use of a medical cyclotron for production of short-lived nuclides using the above-mentioned nuclides, techniques for producing short-lived RI-labeled compounds, and such, are currently under research and development, and anti-DSG3 antibodies can be labeled using such techniques. By administering an anti-DSG3 antibody to patients after labeling it with the above-mentioned positron-emitting nuclides, the labeled anti-DSG3 antibody that recognizes the DSG3 protein present in the living body gathers at primary foci and metastatic foci according to the specificity of the anti-DSG3 antibody at each site of the pathological tissue. Therefore, the presence of primary foci and metastatic foci can be diagnosed by detecting their radioactivity. For use in such diagnostic purpose, emission activity values of 25-4000 keV gamma particles or positrons can be used appropriately. Furthermore, therapeutic effects can be expected by selecting a suitable nuclide and administering it in large quantities. In this case, emission of 70-700 keV gamma particles or positrons can be suitably used.

In another embodiment of the methods of the present invention, the expression of DSG3 mRNA is detected. In the present invention, detection includes quantitative and qualitative detections. Examples of qualitative detection include simple measurement for the presence or absence of DSG3 mRNA, measurement to see whether or not the DSG3 mRNA is present above a certain amount, and measurement that compares the amount of DSG3 mRNA to that of other samples (for example, a control sample). On the other hand, quantitative detection includes, for example, measurement of the DSG3 mRNA concentration and measurement of the amount of DSG3 mRNA.

Test samples are not particularly limited so long as they are samples that may contain DSG3 mRNA, and are preferably samples collected from the body of organisms such as mammals, and more preferably samples collected from humans. Specific examples of the test samples include blood, interstitial fluid, plasma, extravascular fluid, cerebrospinal fluid, synovial fluid, pleural fluid, serum, lymphatic fluid, saliva, and urine, but the test samples are preferably blood, serum, or plasma. Test samples of the present invention also include samples obtained from test samples, such as cell culture solutions and specimens of immobilized tissues or cells collected from the body of an organism.

The cancers that are diagnosed are not particularly limited and may be any cancer, and specific examples include lung cancer, colon cancer, esophageal cancer, stomach cancer, pancreatic cancer, skin cancer, and uterine cancer. Lung cancer is preferable and non-small cell lung cancer is particularly preferable.

Subjects in the present invention may be animal species that genetically carry a DSG3 protein, and many non-human mammals such as monkeys, cattle, sheep, mice, dogs, cats, and hamsters are known as such animal species. Subjects that are suitably used are, in particular, humans, but are not limited thereto.

Specific embodiments of the detection method are described below, but the methods of the present invention are not limited to those methods. First, a sample is prepared from a subject. Next, DSG3 mRNAs included in the sample are detected. In the present invention, it is also acceptable to detect cDNAs synthesized from mRNAs. In the present invention, when the DSG3 mRNA or DSG3-encoding cDNA is detected in a test sample, if a greater amount of DSG3 mRNA or DSG3-encoding cDNA is detected in the test sample than in a negative control or a healthy individual, it can be determined that the subject has cancer or has a high risk of being affected by cancer in the future.

Examples of such methods include methods known to those skilled in the art such as the Northern blotting method, RT-PCR method, and DNA array method.

The detection methods of the present invention described above can be automated using various automatic testing devices, and large quantities of sample can be examined at a time.

A further objective of the present invention is to provide diagnostic agents or kits for detecting the DSG3 protein in a test sample for cancer diagnosis. The diagnostic agents or kits contain at least an anti-DSG3 antibody. When the diagnostic agents or kits are based on an EIA method such as the ELISA method, a carrier for immobilizing the antibody may be included, or a carrier may be bound to the antibody in advance. If the diagnostic agents or kits are based on an aggregation method that uses a carrier such as latex, they may include an antibody-adsorbed carrier.

A further objective of the present invention is to provide diagnostic agents or kits for detecting DSG3 mRNA or DSG3-encoding cDNA in a test sample for cancer diagnosis. The diagnostic agents or kits contain at least a DSG3-encoding DNA (a DNA consisting of the nucleotide sequence of SEQ ID NO: 39) or an oligonucleotide comprising at least 15 nucleotides that are complementary to its complementary strand.

Herein, the term "complementary strand" refers to the other strand with respect to one of the strands of a double-stranded nucleic acid consisting of A:T (U in the case of RNA) and G:C base pairs. In addition, "complementary" refers not only to cases of completely complementary sequences within a region of at least 15 consecutive nucleotides, but also to cases of at least 70%, preferably at least 80%, more preferably 90%, and even more preferably 95% homology or higher in a nucleotide sequence. Homology may be determined using an algorithm described herein.

The oligonucleotides of the present invention can be used as probes or primers for detecting or amplifying DSG3-encoding DNA, and probes or primers for detecting the expression of these DNAs. Furthermore, the oligonucleotides of the present invention can be used in the form of a DNA array substrate.

When such oligonucleotides are used as primers, their lengths are normally 15 bp to 100 bp, and preferably 17 bp to 30 bp. The primers are not particularly limited as long as at least a portion of the DSG3-encoding DNA, or a complementary strand thereof, can be amplified. Furthermore, when they are used as primers, their 3'-end regions can be made to be complementary, and restriction enzyme recognition sequences or tags can be added to their 5' ends.

When using these oligonucleotides as probes, the probes are not particularly limited, as long as they specifically hybridize to at least a portion of the DSG3-encoding DNA, or to a complementary strand thereof. The probes may be synthetic oligonucleotides, and are normally at least 15 bp or longer.

When the oligonucleotides of the present invention are used as probes, it is preferable to use the labeled ones. Examples of labeling methods include labeling methods that use T4 polynucleotide kinase to phosphorylate the 5' ends of oligonucleotides with $^{32}$P, and methods that incorporate a substrate nucleotide labeled with an isotope such as $^{32}$P, a fluorescent dye, biotin or the like, by using a DNA polymerase such as Klenow enzyme, and a random hexamer oligonucleotide or such as a primer (random priming methods and so on).

The oligonucleotides of the present invention can be produced using, for example, a commercially available oligonucleotide synthesizer. The probes may be produced as double-stranded DNA fragments obtained by restriction enzyme treatment or the like.

In the diagnostic agents or kits mentioned above, sterilized water, physiological saline, vegetable oil, surfactants, lipids, solubilizers, buffers, protein stabilizers (BSA, gelatin, or such), preservatives, blocking solutions, reaction solution, reaction-stopping solution, reagents for treating samples, and such may be combined as necessary, in addition to the oligonucleotides and antibodies, which are the active ingredients.

The diagnostic methods of the present invention can be performed both in vitro and in vivo, but preferably preformed in vitro.

In a preferred embodiment of the present invention, an example of the methods for diagnosing cancer is a method comprising the following steps of:
(a) providing a sample collected from a subject; and
(b) detecting for DSG3 proteins contained in the sample of (a).

Moreover, in a preferred embodiment of the present invention, an example of the methods for diagnosing cancer is a method comprising the following steps:
(a) providing a sample collected from a subject; and
(b) detecting for DSG3 genes contained in the sample of (a).

Production of Anti-DSG3 Antibodies

The anti-DSG3 antibodies used in the present invention may be derived from any origin, and may be of any type (monoclonal or polyclonal), and in any form, as long as they specifically bind to a DSG3 protein. Specifically, known antibodies such as animal antibodies (for example, mouse antibodies, rat antibodies, and camel antibodies), human antibodies, chimeric antibodies, and humanized antibodies can be used. The antibodies may be polyclonal antibodies, and are preferably monoclonal antibodies.

Anti-DSG3 antibodies to be used in the present invention can be obtained as polyclonal or monoclonal antibodies using known techniques. In particular, monoclonal antibodies derived from a mammal are preferable as the anti-DSG3 antibody to be used in the present invention. Examples of monoclonal antibodies derived from a mammal include antibodies produced by hybridoma, and antibodies produced by a host transformed by genetic engineering techniques with an expression vector containing an antibody gene.

A monoclonal antibody-producing hybridoma can be prepared essentially using known techniques as follows. Specifically, immunization is performed using the DSG3 protein as a sensitizing antigen according to a general immunization method to obtain immunocytes, which are then fused to known parent cells by a general cell fusion method. Then, hybridoma that produce an anti-DSG3 antibody can be selected by screening for monoclonal antibody-producing cells using a general screening method.

Specifically, monoclonal antibodies are prepared as follows. First, the DSG3 gene having the nucleotide sequence disclosed in GenBank Accession No. NM_001944 (SEQ ID NO: 39) is expressed, and the DSG3 protein is obtained and used as the sensitizing antigen for obtaining the antibody. Specifically, the gene sequence encoding DSG3 is inserted into a known expression vector, and it is used to transform an appropriate host cell. Then, the human DSG3 protein of interest can be purified by a known method from the host cell or its culture supernatant. Alternatively, a purified naturally occurring DSG3 protein can be used in the same manner.

The purified DSG3 protein can be used as a sensitizing antigen for immunization of mammals. A partial peptide of DSG3 can also be used as the sensitizing antigen. In that case, the partial peptide can be obtained from the amino acid sequence of human DSG3 by chemical synthesis, they can also be obtained by incorporating a part of the DSG3 gene into an expression vector and expressing it. Alternatively, the partial peptide can be obtained by degrading the DSG3 protein with a protease, and there are no limitations on the region or size of the partial DSG3 peptides used.

The mammal to be immunized with the sensitizing antigen is not particularly limited, but is preferably selected in consideration of the compatibility with parent cells to be used for cell fusion. For example, rodents such as mice, rats, and hamsters, rabbits, or monkeys are generally used.

The above-described animals can be immunized with a sensitizing antigen according to a known method. For example, as a general method, immunization can be performed by injecting a mammal intraperitoneally or subcutaneously with a sensitizing antigen. Specifically, the sensitizing antigen is diluted at an appropriate dilution with PBS (Phosphate-Buffered Saline), physiological saline, or the like; mixed with a standard adjuvant such as a Freund's complete adjuvant as desired; emulsified; and then administered to mammals several times every four to 21 days. Furthermore, an appropriate carrier can be used when the sensitizing antigen is used for immunization. Particularly when a partial peptide with a small molecular weight is used as a sensitizing antigen, the sensitizing antigen peptide is desirably bound to a carrier protein such as albumin or keyhole limpet hemocyanin, and then used for immunization.

Mammals are immunized as described, and when an increase in the amount of desired antibody in the serum is confirmed, immunocytes are collected from the mammals and subjected to cell fusion. A particularly preferred immunocyte is a splenocyte.

A mammalian myeloma cell is used as a cell to be fused with the above-mentioned immunocyte. A variety of known cell lines can be suitably used as the myeloma cell, and examples include: P3 (P3x63Ag8.653) (J. Immunol. (1979) 123, 1548-1550); P3x63Ag8U.1 (Current Topics in Microbiology and Immunology (1978) 81, 1-7); NS-1 (Kohler. G and Milstein, C. Eur. J. Immunol. (1976) 6, 511-519);

MPC-11 (Margulies. D. H. et al., Cell (1976) 8, 405-415); SP2/0 (Shulman, M. et al., Nature (1978) 276, 269-270); FO (de St. Groth, S. F. et al., J. Immunol. Methods (1980) 35, 1-21); 5194 (Trowbridge, I. S. J. Exp. Med. (1978) 148, 313-323); and 8210 (Galfre, G et al., Nature (1979) 277, 131-133).

Cell fusion of the above-mentioned immunocytes with myeloma cells is essentially performed according to a known method, for example, the method of Kohler and Milstein et al. (Kohler. G and Milstein, C., Methods Enzymol. (1981) 73, 3-46).

More specifically, the above-mentioned cell fusion can be performed in a standard nutritional culture medium in the presence of, for example, a cell-fusion accelerator. A cell-fusion accelerator is, for example, polyethylene glycol (PEG), Sendai virus (HVJ), or the like. If desired, an auxiliary agent such as dimethylsulfoxide can be added to further enhance fusion efficiency.

The ratio of immunocytes to myeloma cells used can be established at one's discretion. For example, the number of immunocytes is preferably set to one to ten times of that of myeloma cells. As a medium to be used for the above-mentioned cell fusion, for example, RPMI1640 medium and MEM medium, which are appropriate for the growth of the above-mentioned myeloma cell line, or other standard media that are used for this type of cell culture can be used. Moreover, a serum supplement solution such as fetal calf serum (FCS) can be suitably added and used in combination.

Cell fusion is performed by thoroughly mixing predetermined amounts of the above-mentioned immunocytes and myeloma cells in the above-mentioned medium, adding and mixing with a PEG solution of generally 30 to 60% (w/v) concentration that has been pre-heated to approximately 37° C. and has, for example, an average molecular weight of approximately 1000 to 6000, so as to form the desired fused cells (hybridomas). Subsequently, the agent for cell fusion or the like which is unfavorable for the growth of hybridomas can be removed by successively adding an appropriate medium such as those listed above, removing the supernatant by centrifugation, and repeating these steps.

Hybridomas obtained in this manner can be selected by culturing the hybridomas in a standard selection medium such as HAT medium (a medium containing hypoxanthine aminopterin, and thymidine). The above-mentioned HAT medium can be used to continue the culturing for a sufficient period of time to kill the cells other than the hybridoma of interest (non-fused cells) (typically, a sufficient period of time is several days to several weeks). Subsequently, hybridomas that produce the antibody of interest can be screened and monocloned by carrying out a standard limiting dilution method.

Alternatively, a DSG3-recognizing antibody can be prepared using the method described in International Patent Publication No. WO 03/104453.

Screening and monocloning an antibody of interest can be suitably performed by a screening method based on known antigen-antibody reaction. For example, the antigen is bound to a carrier such as polystyrene beads or the like, or a commercially available 96-well microtiter plate, followed by reaction with the culture supernatant of the hybridomas. After the carrier is washed, it is reacted with an enzyme-labeled secondary antibody or the like to determine whether or not the antibody of interest that reacts with the sensitizing antigen is contained in the culture supernatant. Hybridomas producing the desired antibodies that have a binding ability to the antigen can be cloned by the limiting dilution method or the like. Antigens used for immunization as well as an operably similar DSG3 protein can be used suitably in this case.

In addition to the above-mentioned method where hybridoma are obtained by immunizing non-human animals with the antigen, desired human antibodies having the activity to bind to a DSG3 protein can also be obtained by sensitizing human lymphocytes with the DSG3 protein in vitro, and fusing the sensitized lymphocytes with human-derived myeloma cells that have infinite division potential (see Japanese Patent Publication Kokoku Publication No. (JP-B) H01-59878 (examined, approved Japanese patent application published for opposition)). Alternatively, desired human antibodies can also be obtained by administering a DSG3 protein that serves as an antigen to a transgenic animal having a complete human antibody gene repertoire to obtain anti-DSG3 antibody-producing cells, immortalizing these cells, and isolating human antibodies against the DSG3 protein from the immortalized cells (see International Patent Publication Nos. WO 94/25585, WO 93/12227, WO 92/03918, and WO 94/02602).

The monoclonal antibody-producing hybridoma produced in this manner can be passaged and cultured in a standard medium, or can be stored for a long period in liquid nitrogen.

To obtain monoclonal antibodies from hybridoma, a method for obtaining monoclonal antibodies as a culture supernatant after culturing the hybridoma according to a standard method, a method for obtaining monoclonal antibodies as an ascites after administering and growing the hybridoma in a compatible mammal, or the like can be suitably carried out. The former method is suitable for obtaining highly purified antibodies, while the latter method is suitable for mass production of antibodies.

In the present invention, a recombinant antibody is produced from recombinant cells generated by genetic engineering techniques that involve cloning the antibody gene from hybridoma, incorporating the gene into an appropriate vector, and introducing the vector into a host, and can be used as a monoclonal antibody (see for example, Vandamme, A. M. et al., Eur. J. Biochem. (1990) 192, 767-775). Specifically, the gene can be obtained from hybridoma cells producing an anti-DSG3 antibody by isolating mRNA that encodes the variable region (V region) of the anti-DSG3 antibody. That is, total RNA can be prepared from the hybridoma cells by a known method such as the guanidine ultracentrifugation method (Chirgwin, J. M. et al., Biochemistry (1979) 18, 5294-5299) or AGPC method (Chomczynski, P. et al., Anal. Biochem. (1987) 162, 156-159), and then, the mRNA of interest can be prepared using an mRNA purification kit (GE Healthcare Bio-Sciences) or the like. In addition, mRNA can also be directly prepared from hybridoma using QuickPrep mRNA Purification Kit (GE Healthcare Bio-Sciences).

cDNA of the antibody V region can be synthesized from the obtained mRNA using reverse transcriptase. cDNA can be synthesized using AMV Reverse Transcriptase First-strand cDNA Synthesis Kit (SEIKAGAKU CORPORATION) or the like. To synthesize and amplify cDNA, for example, 5'-Ampli FINDER RACE Kit (Clontech) and the 5'-RACE method using PCR (Frohman, M. A. et al., Proc. Natl. Acad. Sci. USA (1988) 85, 8998-9002; Belyaysky, A. et al., Nucleic Acids Res. (1989) 17, 2919-2932) can also be used favorably, and in the process of such cDNA synthesis, appropriate restriction enzyme sites, which will be described later, can be introduced into both ends of the cDNA.

The cDNA fragment of interest is purified from the obtained PCR product, and then ligated to a vector DNA. The recombinant vector is prepared in this manner and introduced into *Escherichia coli* or the like, and after colonies are selected, the desired recombinant vector can be prepared from the *E. coli* that formed the colonies. Whether or not the recombinant vector has the cDNA nucleotide sequence of interest can be confirmed by a known method, such as the dideoxynucleotide chain termination method. Once cDNA encoding the V region of the anti-DSG3 antibody of interest is obtained, this cDNA is digested by enzymes that recognize the restriction enzyme sites inserted to both ends of this cDNA. The cDNA encoding the anti-DSG3 antibody V region, which has been digested as described above, is incorporated by ligation into an expression vector that contains a desired antibody constant region (C region), so that the DNA encoding this C region can be fused in frame with the cDNA when digested with the same combination of enzymes.

A preferred method for producing the anti-DSG3 antibody used in the present invention is a method that incorporates the antibody gene into an expression vector so that the gene is expressed under the regulation of an expression control region, for example, an enhancer or a promoter. Next, by suitably transforming a host cell with this expression vector, recombinant cells that express the anti-DSG3 antibody-encoding DNA can be obtained.

An antibody gene can be expressed by incorporating a DNA encoding the antibody heavy chain (H-chain) and a DNA encoding the antibody light chain (L-chain) separately into expression vectors, and then simultaneously transforming a host cell with the vectors; or by incorporating a DNA encoding the H-chain and the L-chain into a single expression vector, and then transforming a host cell with the vector (see International Patent Publication No. WO 94/11523).

Appropriate combinations of suitable hosts and expression vectors can be used for isolating an antibody gene and introducing the gene into an appropriate host to produce the antibody. When using eukaryotic cells as a host, animal cells, plant cells, and fungal cells can be used. Known animal cells include (1) mammalian cells such as CHO, COS, myeloma, baby hamster kidney (BHK), HeLa, and Vero cells; (2) amphibian cells such as *Xenopus* oocytes; and (3) insect cells such as sf9, sf21, and Tn5. Known plant cells include cells derived from the *Nicotiana* genus such as *Nicotiana tabacum*, from which callus can be cultured. Known fungal cells include yeasts such as the *Saccharomyces* genus, for example, *Saccharomyces cerevisiae*, and filamentous fungi such as the *Aspergillus* genus, for example, *Aspergillus niger*. Production systems that utilize bacterial cells can be suitably used when using prokaryotic cells. Known bacterial cells include *E. coli* and *Bacillus subtilis*. By introducing expression vectors comprising the antibody genes of interest into these cells by transformation, and then culturing the transformed cells in vitro, the desired antibodies can be obtained from the transformed cell culture.

In addition to the above host cells, transgenic animals can also be used suitably to produce a recombinant antibody. For example, the antibody gene can be inserted in frame into a gene that encodes a protein inherently produced in milk, for example, goat β-casein to construct a fused gene. A DNA fragment containing the fused gene, which has been inserted with the antibody gene, is injected into a goat embryo, and then this injected embryo is introduced into a female goat. Desired antibodies can be obtained from milk produced by the transgenic goat born from the goat that received the embryo or progeny thereof. To increase the volume of milk containing the desired antibody produced by the transgenic goat, hormones can be used on the transgenic goat as necessary (Ebert, K. M. et al., Bio/Technology (1994) 12, 699-702).

Animal-derived antibody C regions can be used for the C regions of a recombinant antibody of the present invention. For example, Cγ1, Cγ2a, Cγ2b, Cγ3, Cμ, Cδ, Cα1, Cβ2, and Cε can be used for the mouse antibody H-chain C-region, and Cκ and Cλ can be used for the L-chain C-region. In addition to mouse antibodies, antibodies of animals such as rats, rabbits, goat, sheep, camels, and monkeys can be used as animal antibodies. Their sequences are known. Furthermore, the C region can be modified to improve the stability of the antibodies or their production.

In the present invention, genetically recombinant antibodies that are artificially modified for the purpose of reducing xenoantigenicity against humans, or the like can be used. Examples of such include chimeric antibodies and humanized antibodies. These modified antibodies can be produced using known methods. A chimeric antibody is an antibody comprising the antibody heavy chain and light chain variable regions of a nonhuman mammal such as a mouse, and the antibody heavy chain and light chain constant regions of a human. The DNA encoding a mouse antibody variable region is ligated to the DNA encoding a human antibody constant region, and this is incorporated into an expression vector to produce a recombinant vector expressing the DNA. The recombinant cells that have been transformed with the vector are cultured, and the incorporated DNA is expressed to obtain the chimeric antibody produced in the culture.

A human antibody C region can be used for the C regions of the chimeric antibody and humanized antibody, and for example, Cγ1, Cγ2, Cγ3, Cγ4, Cμ, Cδ, Cα1, Cβ2, and Cε can be used for the H chain, and Cκ and Cλ can be used for the L-chain. Their sequences are known. Furthermore, the human antibody C region can be modified to improve the stability of the antibody or its production.

A chimeric antibody consists of the V region of an antibody derived from a non-human animal, and a C region derived from a human antibody. On the other hand, a humanized antibody consists of the complementarity determining region (CDR) of an antibody derived from a non-human animal, and the framework region (FR) and C region derived from a human antibody. Since the antigenicity of a humanized antibody in human body is reduced, a humanized antibody is useful as an active ingredient for therapeutic agents of the present invention.

A humanized antibody, which is also called a reshaped human antibody, is obtained by transplanting, in place of a human antibody CDR, the CDR of a non-human animal antibody such as a mouse antibody, and common genetic recombination techniques for such preparation are also known. Specifically, a DNA sequence is designed for ligating a mouse antibody CDR in frame with a human antibody FR, and is synthesized by PCR using several oligonucleotides designed to contain overlapping portions at their ends as primers. An integration vector can be produced by inserting the DNA obtained as described above and a DNA that encodes a human antibody C region into an expression vector so that they will ligate in frame. After incorporating this integration vector into a host to establish recombinant cells, the recombinant cells are cultured, and the DNA encoding the humanized antibody is expressed to produce the humanized antibody in the cell culture (see, European Patent Application No. EP 239,400, and International Patent Application No. WO 96/02576).

By qualitatively or quantitatively measuring and evaluating the activity of the humanized antibody produced as described above to bind to antigens, human antibody FRs that would make the CDRs form a favorable antigen-binding site when ligated through the CDRs can be suitably selected. As necessary, amino acids in an FR may be substituted such that the CDRs of a reshaped human antibody forms an appropriate antigen-binding site. The above-mentioned amino acid substitution can be introduced by appropriately using the PCR method used when fusing mouse CDR with human FR, and mutant FR sequences having the desired characteristics can be selected by measuring and evaluating the activity of the amino acid-substituted mutant antibody to bind to the antigen by the above-mentioned method (Sato, K. et al., Cancer Res. 1993, 53, 851-856).

Methods for obtaining human antibodies are also known. For example, desired human antibodies with antigen-binding activity can be obtained by sensitizing human lymphocytes with a desired antigen or cells expressing a desired antigen in vitro; and fusing the sensitized lymphocytes with human myeloma cells such as U266 (see JP-B H01-59878). Alternatively, a desired human antibody can be obtained by using a desired antigen to immunize a transgenic animal that comprises the entire repertoire of human antibody genes (see International Patent Application Nos. WO 93/12227, WO 92/03918, WO 94/02602, WO 94/25585, WO 96/34096, and WO 96/33735). Furthermore, techniques to obtain human antibodies by panning a human antibody library are also known. For example, the V region of a human antibody is expressed as a single chain antibody (scFv) on the phage surface using a phage display method, and phages that bind to the antigen can be selected. By analyzing the genes of selected phages, the DNA sequences encoding the V regions of human antibodies that bind to the antigen can be determined. After determining the DNA sequences of scFvs that bind to the antigen, the V region sequence is fused in frame with the desired human antibody C region sequence, and this is inserted into a suitable expression vector to produce an expression vector. This expression vector can be introduced into suitable expression cells such as those described above, and the human antibody-encoding gene can be expressed to obtain the human antibodies. Such methods are well known and one can refer to International Patent Application Nos. WO 92/01047, WO 92/20791, WO 93/06213, WO 93/11236, WO 93/19172, WO 95/01438, and WO 95/15388.

The antibody used in the present invention is not limited to bivalent antibodies represented by IgG but includes monovalent antibodies and multivalent antibodies represented by IgM, so long as it binds to the DSG3 protein. The multivalent antibody of the present invention includes a multivalent antibody that has the same antigen binding sites, and a multivalent antibody that has partially or completely different antigen binding sites.

The antibody used in the present invention is not limited to the whole antibody molecule, but includes minibodies and modified products thereof, so long as they bind to the DSG3 protein.

A minibody comprises antibody fragments lacking a portion of a whole antibody (for example, whole IgG), and is not particularly limited so long as it has antigen-binding ability. There are no particular limitations on the antibody fragments of the present invention, so long as they are portions of a whole antibody, but they preferably contain a heavy chain variable region (VH) and/or a light chain variable region (VL). The amino acid sequence of VH or VL may have substitutions, deletions, additions, and/or insertions. Furthermore, so long as it has antigen-binding ability, part of VH and/or VL can be deleted. The variable region may be chimerized or humanized. Specific examples of the antibody fragments include Fab, Fab', F(ab')2, and Fv. Specific examples of minibodies include Fab, Fab', F(ab')2, Fv, scFv (single chain Fv), diabody, and sc(Fv)2 (single chain (Fv)2). Multimers of these antibodies (for example, dimers, trimers, tetramers, and polymers) are also included in the minibodies of the present invention.

Antibody fragments can be produced by treating an antibody with an enzyme, such as papain or pepsin. Alternatively, genes encoding these antibody fragments can be constructed, introduced into expression vectors, and expressed in appropriate host cells (see, for example, Co, M. S. et al., J. Immunol. (1994) 152, 2968-2976; Better, M. and Horwitz, A. H., Methods in Enzymology (1989) 178, 476-496; Plueckthun, A. and Skerra, A., Methods in Enzymology (1989) 178, 476-496; Lamoyi, E., Methods in Enzymology (1989) 121, 652-663; Rousseaux, J. et al., Methods in Enzymology (1989) 121, 663-669; and Bird, R. E. et al., TIBTECH (1991) 9, 132-137).

A diabody refers to a bivalent antibody fragment constructed by gene fusion (Hollinger P. et al., Proc. Natl. Acad. Sci. USA 90: 6444-6448 (1993); EP 404,097; WO 93/11161; and such). A diabody is a dimer composed of two polypeptide chains, and generally, the polypeptide chains are individually linked by a linker of, for example, five residues or so, which is short enough to prevent binding between VL and VH in the same chain. VL and VH that are encoded by the same polypeptide chain have a short linker between them, and form a dimer because they cannot form a single chain variable region fragment. Therefore, diabodies have two antigen binding sites.

scFv can be obtained by ligating the H-chain V region and L-chain V region of an antibody. In this scFv, the H-chain V region and L-chain V region are ligated via a linker, preferably a peptide linker (Huston, J. S. et al., Proc. Natl. Acad. Sci. U.S.A., 1988, 85, 5879-5883). The H-chain V region and L-chain V region of the scFv and may be derived from any of the antibodies described herein. The peptide linker for ligating the V regions is not particularly limited, but for example, any single-chain peptide consisting of 3 to 25 residues or so, or a peptide linker described below can be used. PCR methods such as those described above can be used for ligating the V regions. An scFv-encoding DNA can be amplified by a PCR method using as a template, either a whole DNA or a partial DNA encoding a desired amino acid sequence selected from a DNA sequence encoding the H chain or the H-chain V region of the above-mentioned antibody, and a DNA sequence encoding the L chain or the L-chain V region of the above-mentioned antibody; and using a primer pair having sequences corresponding to the sequences of the two ends. Next, a DNA comprising the desired sequence can be obtained by performing a PCR reaction using the combination of a DNA encoding the peptide linker portion, and a primer pair having sequences designed so that both ends of the DNA will be ligated to the H chain and L chain. Once the scFv-encoding DNA is constructed, expression vectors containing the DNA, and recombinant cells transformed by these expression vectors can be obtained according to conventional methods. Furthermore, the scFvs can be obtained by culturing the resulting recombinant cells and expressing the scFv-encoding DNA.

sc(Fv)2 is a minibody prepared by ligating two VHs and two VLs with linkers or such to form a single chain (Hudson et al., J. Immunol. Methods 1999; 231: 177-189). sc(Fv)2 can be produced, for example, by joining scFvs with a linker.

Moreover, antibodies in which two VHs and two VLs are arranged in the order of VH, VL, VH, and VL ([VH]-linker-[VL]-linker-[VH]-linker-[VL]), starting from the N-terminal side of a single chain polypeptide, are preferred.

The order of the two VHs and the two VLs is not particularly limited to the above-mentioned arrangement, and they may be placed in any order. Examples include the following arrangements:

[VL]-linker-[VH]-linker-[VH]-linker-[VL]
[VH]-linker-[VL]-linker-[VL]-linker-[VH]
[VH]-linker-[VH]-linker-[VL]-linker-[VL]
[VL]-linker-[VL]-linker-[VH]-linker-[VH]
[VL]-linker-[VH]-linker-[VL]-linker-[VH]

Any arbitrary peptide linker can be introduced by genetic engineering, and synthetic linkers (see, for example, those disclosed in Protein Engineering, 9(3), 299-305, 1996) or such can be used as linkers for linking the antibody variable regions, but in the present invention, peptide linkers are preferable. The length of the peptide linkers is not particularly limited, and can be suitably selected by those skilled in the art according to the purpose; however, the length is generally 1 to 100 amino acids, preferably 3 to 50 amino acids, more preferably 5 to 30 amino acids, and particularly preferably 12 to 18 amino acids (for example, 15 amino acids).

Examples of the peptide linkers include:

Ser

Gly-Ser

Gly-Gly-Ser

Ser-Gly-Gly

Gly-Gly-Gly-Ser (SEQ ID NO: 72)

Ser-Gly-Gly-Gly (SEQ ID NO: 73)

Gly-Gly-Gly-Gly-Ser (SEQ ID NO: 74)

Ser-Gly-Gly-Gly-Gly (SEQ ID NO: 75)

Gly-Gly-Gly-Gly-Gly-Ser (SEQ ID NO: 76)

Ser-Gly-Gly-Gly-Gly-Gly (SEQ ID NO: 77)

Gly-Gly-Gly-Gly-Gly-Gly-Ser (SEQ ID NO: 78)

Ser-Gly-Gly-Gly-Gly-Gly-Gly (SEQ ID NO: 79)

(Gly-Gly-Gly-Gly-Ser)n (SEQ ID NO: 74)

(Ser-Gly-Gly-Gly-Gly)n (SEQ ID NO: 75)

in which n is an integer of 1 or larger. The length and sequence of the peptide linkers can be selected appropriately by those skilled in the art according to the purpose.

Therefore, a particularly preferred embodiment of sc(Fv)2 in the present invention is, for example, the following sc(Fv)2: [VH]-peptide linker (15 amino acids)-[VL]-peptide linker (15 amino acids)-[VH]-peptide linker (15 amino acids)-[VL]

Synthetic chemical linkers (chemical crosslinking agents) which include crosslinking agents routinely used to crosslink peptides and are, for example, N-hydroxy succinimide (NHS), disuccinimidyl suberate (DSS), bis(sulfosuccinimidyl) suberate ($BS^3$), dithiobis(succinimidyl propionate) (DSP), dithiobis(sulfosuccinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl] sulfone (BSOCOES), and bis[2-(sulfosuccinimidoxycarbonyloxy) ethyl] sulfone (sulfo-BSOCOES). These crosslinking agents are commercially available.

Usually, three linkers are required to link four antibody variable regions. The linkers to be used may all be of the same type or different types. In the present invention, a preferred minibody is a diabody or an sc(Fv)2. Such minibody can be obtained by treating an antibody with an enzyme, such as papain or pepsin, to generate antibody fragments, or by constructing DNAs that encode these antibody fragments, introducing them into expression vectors, and then expressing them in appropriate host cells (see, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; and Bird, R. E. and Walker, B. W., Trends Biotechnol. (1991) 9, 132-137).

The antibodies of the present invention can be exemplified by the antibodies of (1) to (62) below, but are not limited thereto. The antibodies of (1) to (62) include, for example, full-length antibodies, minibodies, animal antibodies, chimeric antibodies, humanized antibodies, and human antibodies:

(1) an antibody that comprises an H chain having the amino acid sequence of SEQ ID NO: 2 (sequence of the DF151 antibody H-chain CDR1) as CDR1, the amino acid sequence of SEQ ID NO: 4 (sequence of the DF151 antibody H chain CDR2) as CDR2, and the amino acid sequence of SEQ ID NO: 6 (sequence of the DF151 antibody H-chain CDR3) as CDR3;

(2) an antibody that comprises the H chain of (1) having the amino acid sequence of SEQ ID NO: 8 (sequence of the DF151 antibody CH) as CH (H-chain constant region);

(3) an antibody that comprises the H chain of (1) having the amino acid sequence of SEQ ID NO: 10 (sequence of the CH of the mouse-human chimeric DF151 antibody) as CH;

(4) an antibody that comprises an L chain having the amino acid sequence of SEQ ID NO: 12 (sequence of the DF151 antibody L-chain CDR1) as CDR1, the amino acid sequence of SEQ ID NO: 14 (sequence of the DF151 antibody L-chain CDR2) as CDR2, and the amino acid sequence of SEQ ID NO: 16 (sequence of the DF151 antibody L-chain CDR3) as CDR3;

(5) an antibody that comprises the L chain of (4) having the amino acid sequence of SEQ ID NO: 18 (sequence of the DF151 antibody CL) as CL (L-chain constant region);

(6) an antibody that comprises the L chain of (4) having the amino acid sequence of SEQ ID NO: 20 (sequence of the mouse-human chimeric DF151 antibody CL) as CL;

(7) an antibody that comprises the H chain of (1) and the L chain of (4);

(8) an antibody that comprises the H chain of (2) and the L chain of (5);

(9) an antibody that comprises the H chain of (3) and the L chain of (6);

(10) an antibody that comprises an H chain having the amino acid sequence of SEQ ID NO: 22 (sequence of the DF364 antibody H-chain CDR1) as CDR1, the amino acid sequence of SEQ ID NO: 24 (sequence of the DF364 antibody H-chain CDR2) as CDR2, and the amino acid sequence of SEQ ID NO: 26 (sequence of the DF364 antibody H-chain CDR3) as CDR3;

(11) an antibody that comprises the H chain of (10) having the amino acid sequence of SEQ ID NO: 28 (sequence of the DF364 antibody CH) as CH;

(12) an antibody that comprises the H chain of (10) having the amino acid sequence of SEQ ID NO: 10 (sequence of the mouse-human chimeric DF364 antibody CH) as CH;

(13) an antibody that comprises an L chain having the amino acid sequence of SEQ ID NO: 30 (sequence of the DF364 antibody L-chain CDR1) as CDR1, the amino acid sequence of SEQ ID NO: 32 (sequence of the DF364 antibody L-chain CDR2) as CDR2, and the amino acid sequence of SEQ ID NO: 34 (sequence of the DF364 antibody L-chain CDR3) as CDR3;

(14) an antibody that comprises the L chain of (13) having the amino acid sequence of SEQ ID NO: 36 (sequence of the DF364 antibody CL) as CL;

(15) an antibody that comprises the L chain of (13) having the amino acid sequence of SEQ ID NO: 20 (sequence of the mouse-human chimeric DF364 antibody CL) as CL;

(16) an antibody that comprises the H chain of (10) and the L chain of (13);

(17) an antibody that comprises the H chain of (11) and the L chain of (14);

(18) an antibody that comprises the H chain of (12) and the L chain of (15);

(19) an antibody that comprises the H chain of (1) and the L chain of (13);

(20) an antibody that comprises the H chain of (2) and the L chain of (14);

(21) an antibody that comprises the H chain of (3) and the L chain of (15);

(22) an antibody that comprises the H chain of (10) and the L chain of (4);

(23) an antibody that comprises the H chain of (11) and the L chain of (5);

(24) an antibody that comprises the H chain of (12) and the L chain of (6);

(25) an antibody that comprises an H chain having the amino acid sequence of SEQ ID NO: 81 (sequence of the DF366 antibody H-chain CDR1) as CDR1, the amino acid sequence of SEQ ID NO: 83 (sequence of the DF366 antibody H-chain CDR2) as CDR2, and the amino acid sequence of SEQ ID NO: 85 (sequence of the DF366 antibody H-chain CDR3) as CDR3;

(26) an antibody that comprises the H chain of (25) having the amino acid sequence of SEQ ID NO: 28 (sequence of the DF366 antibody CH) as CH;

(27) an antibody that comprises the H chain of (25) having the amino acid sequence of SEQ ID NO: 10 (sequence of the mouse-human chimeric DF366 antibody CH) as CH;

(28) an antibody that comprises an L chain having the amino acid sequence of SEQ ID NO: 87 (sequence of the DF366 antibody L-chain CDR1) as CDR1, the amino acid sequence of SEQ ID NO: 89 (sequence of the DF366 antibody L-chain CDR2) as CDR2, and the amino acid sequence of SEQ ID NO: 91 (sequence of the DF366 antibody L-chain CDR3) as CDR3;

(29) an antibody that comprises the L chain of (28) having the amino acid sequence of SEQ ID NO: 36 (sequence of the CL of the DF366 antibody) as CL;

(30) an antibody that comprises the L chain of (28) having the amino acid sequence of SEQ ID NO: 20 (sequence of the CL of the mouse-human chimeric DF366 antibody) as CL;

(31) an antibody that comprises the H chain of (25) and the L chain of (28);

(32) an antibody that comprises the H chain of (26) and the L chain of (29);

(33) an antibody that comprises the H chain of (27) and the L chain of (30);

(34) an antibody that comprises the H chain of (1) and the L chain of (28);

(35) an antibody that comprises the H chain of (2) and the L chain of (29);

(36) an antibody that comprises the H chain of (3) and the L chain of (30);

(37) an antibody that comprises the H chain of (10) and the L chain of (28);

(38) an antibody that comprises the H chain of (11) and the L chain of (29);

(39) an antibody that comprises the H chain of (12) and the L chain of (30);

(40) an antibody that comprises the H chain of (25) and the L chain of (4);

(41) an antibody that comprises the H chain of (26) and the L chain of (5);

(42) an antibody that comprises the H chain of (27) and the L chain of (6);

(43) an antibody that comprises the H chain of (25) and the L chain of (13);

(44) an antibody that comprises the H chain of (26) and the L chain of (14);

(45) an antibody that comprises the H chain of (27) and the L chain of (15);

(46) an antibody that comprises the H chain of (1) having the amino acid sequence of SEQ ID NO: 108 (sequence of the CH of a mouse IgG2a antibody) as CH;

(47) an antibody that comprises the L chain of (4) having the amino acid sequence of SEQ ID NO: 112 (sequence of the CL of a mouse IgG2a antibody) as CL;

(48) an antibody that comprises the H chain of (10) having the amino acid sequence of SEQ ID NO: 108 (sequence of the CH of a mouse IgG2a antibody) as CH;

(49) an antibody that comprises the L chain of (13) having the amino acid sequence of SEQ ID NO: 112 (sequence of the CL of a mouse IgG2a antibody) as CL;

(50) an antibody that comprises the H chain of (25) having the amino acid sequence of SEQ ID NO: 108 (sequence of the CH of a mouse IgG2a antibody) as CH;

(51) an antibody that comprises the L chain of (28) having the amino acid sequence of SEQ ID NO: 112 (sequence of the CL of a mouse IgG2a antibody) as CL;

(52) an antibody that comprises the H chain of (46) and the L chain of (47);

(53) an antibody that comprises the H chain of (48) and the L chain of (49);

(54) an antibody that comprises the H chain of (50) and the L chain of (51);

(55) an antibody that comprises the H chain of (46) and the L chain of (49);

(56) an antibody that comprises the H chain of (48) and the L chain of (51);

(57) an antibody that comprises the H chain of (50) and the L chain of (47);

(58) an antibody that comprises the H chain of (46) and the L chain of (51);

(59) an antibody that comprises the H chain of (48) and the L chain of (47);

(60) an antibody that comprises the H chain of (50) and the L chain of (49);

(61) an antibody having one or more amino acid substitutions, deletions, additions, and/or insertions in the antibody of any one of (1) to (60) and having an activity equivalent to that of the antibody of any one of (1) to (60); and

(62) an antibody that binds to the same epitope as the DSG3 protein epitope to which the antibody of any one of (1) to (60) binds.

An example of VH in the above-mentioned "H chain having the amino acid sequence of SEQ ID NO: 2 (sequence of the DF151 antibody H-chain CDR1) as CDR1, the amino acid sequence of SEQ ID NO: 4 (sequence of the DF151 antibody H-chain CDR2) as CDR2, and the amino acid sequence of SEQ ID NO: 6 (sequence of the DF151 antibody H-chain CDR3) as CDR3" of (1) includes a VH having the amino acid sequence of SEQ ID NO: 46 (sequence of the DF151 antibody VH).

An example of VL in the above-mentioned "L chain having the amino acid sequence of SEQ ID NO: 12 (sequence of the DF151 antibody L-chain CDR1) as CDR1, the amino acid sequence of SEQ ID NO: 14 (sequence of the DF151 antibody L-chain CDR2) as CDR2, and the amino acid sequence of SEQ ID NO: 16 (sequence of the DF151 antibody L-chain CDR3) as CDR3" of (4) includes a VL having the amino acid sequence of SEQ ID NO: 48 (sequence of the DF151 antibody VL).

An example of VH in the above-mentioned "H chain having the amino acid sequence of SEQ ID NO: 22 (sequence of the DF364 antibody H-chain CDR1) as CDR1, the amino acid sequence of SEQ ID NO: 24 (sequence of the DF364 antibody H-chain CDR2) as CDR2, and the amino acid sequence of SEQ ID NO: 26 (sequence of the DF364 antibody H-chain CDR3) as CDR3" of (10) includes a VH having the amino acid sequence of SEQ ID NO: 50 (sequence of the DF364 antibody VH).

An example of VL in the above-mentioned "L chain having the amino acid sequence of SEQ ID NO: 30 (sequence of the DF364 antibody L-chain CDR1) as CDR1, the amino acid sequence of SEQ ID NO: 32 (sequence of the DF364 antibody L-chain CDR2) as CDR2, and the amino acid sequence of SEQ ID NO: 34 (sequence of the DF364 antibody L-chain CDR3) as CDR3" of (13) includes a VL having the amino acid sequence of SEQ ID NO: 52 (sequence of the DF364 antibody VL).

An example of VH in the above-mentioned "H chain having the amino acid sequence of SEQ ID NO: 81 (sequence of the DF366 antibody H-chain CDR1) as CDR1, the amino acid sequence of SEQ ID NO: 83 (sequence of the DF366 antibody H-chain CDR2) as CDR2, and the amino acid sequence of SEQ ID NO: 85 (sequence of the DF366 antibody H-chain CDR3) as CDR3" of (25) includes a VH having the amino acid sequence of SEQ ID NO: 93 (sequence of the DF366 antibody VH).

An example of VL in the above-mentioned "L chain having the amino acid sequence of SEQ ID NO: 87 (sequence of the DF366 antibody L-chain CDR1) as CDR1, the amino acid sequence of SEQ ID NO: 89 (sequence of the DF366 antibody L-chain CDR2) as CDR2, and the amino acid sequence of SEQ ID NO: 91 (sequence of the DF366 antibody L-chain CDR3) as CDR3" of (28) includes a VL having the amino acid sequence of SEQ ID NO: 95 (sequence of the DF366 antibody VL).

A preferred embodiment of the above-mentioned antibody of (61) is an antibody in which CDR has not been modified. As an example, a preferred embodiment of "an antibody having one or more amino acid substitutions, deletions, additions, and/or insertions in the antibody of (1) and having an activity equivalent to that of the antibody of (1)" among the above-mentioned antibody of (61) is "an antibody having an activity equivalent to that of the antibody of (1) and having one or more amino acid substitutions, deletions, additions, and/or insertions in the antibody of (1), and also comprising an H chain having the amino acid sequence of SEQ ID NO: 2 as CDR1, the amino acid sequence of SEQ ID NO: 4 as CDR2, and the amino acid sequence of SEQ ID NO: 6 as CDR3". Preferred embodiments of other antibodies included in the above-mentioned antibody of (61) can be expressed in a similar manner.

Methods of introducing mutations into polypeptides are well known to those skilled in the art as methods for preparing polypeptides that are functionally equivalent to a certain polypeptide. For example, those skilled in the art can prepare an antibody functionally equivalent to an antibody of the present invention by introducing appropriate mutations into the antibody using site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc. Natl. Acad. Sci. USA. 82, 488-492; Kunkel (1988) Methods Enzymol. 85, 2763-2766) and such. Amino acid mutations may also occur naturally. In this way, the antibodies of the present invention also comprise antibodies comprising amino acid sequences with one or more amino acid mutations in the amino acid sequences of the antibodies of the present invention, and which are functionally equivalent to the antibodies of the present invention. The number of amino acids that are mutated in such mutants is generally considered to be 50 amino acids or less, preferably 30 amino acids or less, and more preferably 10 amino acids or less (for example, 5 amino acids or less).

It is desirable that the amino acid residues are mutated into amino acids in which the properties of the amino acid side chains are conserved. Examples of amino acid side chain properties include: hydrophobic amino acids (A, I, L, M, F, P, W, Y, and V), hydrophilic amino acids (R, D, N, C, E, Q, G, H, K, S, and T), amino acids comprising the following side chains: aliphatic side chains (G, A, V, L, I, and P); hydroxyl-containing side chains (S, T, and Y); sulfur-containing side chains (C and M); carboxylic acid- and amide-containing side chains (D, N, E, and Q); basic side chains (R, K, and H); or aromatic ring-containing side chains (H, F, Y, and W) (amino acids are represented by one-letter codes in parentheses).

Polypeptides comprising a modified amino acid sequence, in which one or more amino acid residues in a certain amino acid sequence is deleted, added, and/or substituted with other amino acids, are known to retain their original biological activities (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413).

Antibodies that bind to the same epitope as the anti-DSG3 antibodies disclosed in the present invention are also provided. Such antibodies can be obtained, for example, by the following method.

To determine if a test antibody can compete for binding to the same epitope bound by the anti-DSG3 antibodies disclosed in the invention of this application, a cross-blocking assay, for example, a competitive ELISA assay can be performed. For example, in a competitive ELISA assay, DSG3 protein-coated wells of a microtiter plate are pre-incubated with or without a candidate competing antibody, and then a biotin-labeled anti-DSG3 antibody of the present invention is added. The amount of labeled anti-DSG3 antibody bound to the DSG3 protein in the wells can be measured using avidin-peroxidase conjugate and an appropriate substrate. The antibody can be labeled, for example, with a radioactive label or fluorescent label, or some other detectable and measurable label. The amount of labeled anti-DSG3 antibody bound to the DSG3 protein is indirectly correlated to the binding ability of the candidate competing antibody (test antibody) that competes for binding to the same epitope. That is, the greater the affinity of the test antibody for the same epitope, the lower the binding activity of the labeled anti-DSG3 antibody to the DSG3 protein-coated wells. A candidate competing antibody is considered to be an antibody that binds substantially to the same epitope or that competes for binding to the same epitope as an anti-DSG3 antibody of the present invention if the candidate competing antibody can block binding of the DSG3 antibody by at least 20%, preferably by at least 20% to 50%, and even more preferably, by at least 50%, as compared to the binding activity obtained in a control experiment performed in the absence of the candidate competing antibody.

Antibodies that bind to the same epitope as the anti-DSG3 antibodies include, for example, the above-mentioned antibody of (62), but are not limited thereto.

As described above, the above-mentioned antibodies of (1) to (62) include not only monovalent antibodies but also multivalent antibodies with two or more valencies. Multivalent antibodies of the present invention include multivalent antibodies whose antigen binding sites are all the same and multivalent antibodies whose antigen binding sites are partially or completely different.

The following antibodies are examples of multivalent antibodies that have different antigen binding sites, but the antibodies of the present invention are not limited thereto: an antibody comprising at least two H chain and L chain pairs (hereinafter referred to as HL pairs) selected from the HL pairs of (7), (16), (19), (22), (31), (34), (37), (40), and (43); an antibody comprising at least two HL pairs selected from the HL pairs of (8), (17), (20), (23), (32), (35), (38), (41), and (44);

an antibody comprising at least two HL pairs selected from the HL pairs of (9), (18), (21), (24), (33), (36), (39), (42), and (45); and an antibody comprising at least two HL pairs selected from the HL pairs of (52) to (60).

Antibodies bound to various types of molecules such as polyethylene glycol (PEG) can also be used as modified antibodies. Moreover, chemotherapeutic agents, toxic peptides, or radioactive chemical substances can be bound to the antibodies. Such modified antibodies (hereinafter referred to as antibody conjugates) can be obtained by subjecting the obtained antibodies to chemical modification. Methods for modifying antibodies are already established in this field. Furthermore, as described below, such antibodies can also be obtained in the molecular form of a bispecific antibody designed using genetic engineering techniques to recognize not only DSG3 proteins, but also chemotherapeutic agents, toxic peptides, radioactive chemical compounds, or such. These antibodies are included in the "antibodies" of the present invention.

Low-molecular-weight chemotherapeutic agents such as azaribine, anastrozole, azacytidine, bleomycin, bortezomib, bryostatin-1, busulfan, camptothecin, 10-hydroxycamptothecin, carmustine, celebrex, chlorambucil, cisplatin, irinotecan, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin, ethinyl estradiol, estramustine, etoposide, etoposide glucuronide, floxuridine, fludarabine, flutamide, fluorouracil, fluoxymesterone, gemcitabine, hydroxyprogesterone caproate, hydroxyurea, idarubicin, ifosfamide, leucovorin, lomustine, mechlorethamine, medroxyprogesterone acetate, megestrol acetate, melphalan, mercaptopurine, methotrexate, mitoxantrone, mithramycin, mitomycin, mitotane, phenylbutyrate, prednisone, procarbazine, paclitaxel, pentostatin, semustine streptozocin, tamoxifen, taxanes, taxol, testosterone propionate, thalidomide, thioguanine, thiotepa, teniposide, topotecan, uracil mustard, vinblastine, vinorelbine, and vincristine can be suitably used as chemotherapeutic agents (including prodrugs that are converted to such chemotherapeutic agents nonenzymatically or enzymatically in vivo) that are bound to anti-DSG3 antibodies to bring about cytotoxic activity. Moreover, toxic peptides such as ricin, abrin, ribonuclease, onconase, DNase I, Staphylococcal enterotoxin-A, pokeweed antiviral protein, gelonin, diphtheria toxin, *Pseudomonas* exotoxin, *Pseudomonas* endotoxin, L-asparaginase, and PEG L-Asparaginase can also be suitably used. In another embodiment, one or two or more of the low-molecular-weight chemotherapeutic agents can be suitably used in combination and one or two or more of the toxic peptides. For the bond between an anti-DSG3 antibody and the above-mentioned low-molecular-weight chemotherapeutic agent, a covalent bond or non-covalent bond can be suitably selected, and methods for preparing chemotherapeutic agent-bound antibodies are known.

Furthermore, for binding with proteinaceous pharmaceutical agents or toxins, gene recombination techniques can be used to construct a recombinant vector in which a DNA encoding the above-mentioned toxic peptide and a DNA encoding an anti-DSG3 antibody are fused in frame and inserted into an expression vector. This vector is introduced into suitable host cells, and transformed cells are obtained and cultured. Recombinant proteins can be prepared by expressing the incorporated DNA.

Furthermore, the antibody used in the present invention may be a bispecific antibody. The bispecific antibody may have antigen-binding sites that recognize different epitopes on a DSG3 molecule. Alternatively, one antigen-binding site may recognize DSG3 and the other antigen-binding site may recognize a cytotoxic substance such as a chemotherapeutic agent, toxic peptide, or radioactive chemical substance. This enables the cytotoxic substance to directly act on cells expressing DSG3, thereby specifically damaging tumor cells and suppressing tumor cell proliferation. Alternatively, one may prepare a bispecific antibody in which the other antigen-binding site recognizes an antigen that is similar to but different from DSG3, and specifically expressed on the surface of the target cancer cells. Bispecific antibodies can be produced by linking the HL pairs from two types of antibodies, or by fusing hybridomas producing different monoclonal antibodies to prepare bispecific antibody-producing fused cells. Bispecific antibodies can also be prepared by genetic engineering techniques.

Antibody genes constructed described above can be obtained through expression by known methods. In the case of mammalian cells, the antibody genes can be expressed by operably linking an effective, commonly used promoter, the antibody gene to be expressed, and a polyA signal on its 3' downstream side. An example of the promoter/enhancer is human cytomegalovirus immediate early promoter/enhancer.

Examples of other promoters/enhancers that can be used for expression of an antibody to be used in the present invention include viral promoters/enhancers from retrovirus, polyoma virus, adenovirus, or simian virus 40 (SV40), and mammalian cell-derived promoters/enhancers such as human elongation factor 1α (HEF1α).

When an SV40 promoter/enhancer is used, gene expression can be readily carried out by the method of Mulligan et al. (Nature (1979) 277, 108), and when an HEF1α promoter/enhancer is used, gene expression can be readily carried out by the method of Mizushima et al. (Nucleic Acids Res. (1990) 18, 5322).

In the case of *E. coli*, an effective, commonly used promoter, a signal sequence for antibody secretion, and the antibody gene to be expressed are functionally linked to express the gene. Examples of a promoter include the lacZ promoter and the araB promoter. When the lacZ promoter is used, the gene can be expressed by the method of Ward et al. (Nature (1989) 341, 544-546; FASEB J. (1992) 6, 2422-2427), and when the araB promoter is used, the gene can be expressed by the method of Better et al. (Science (1988) 240, 1041-1043).

With regard to the signal sequence for antibody secretion, the pelB signal sequence (Lei, S. P. et al., J. Bacteriol. (1987) 169, 4379) may be used for production in the periplasm of *E. coli*. After the antibody produced in the periplasm is isolated, the antibody structure is refolded by using a protein denaturant like guanidine hydrochloride or urea so that the antibody will have the desired binding activity.

The replication origin inserted into the expression vector includes, for example, those derived from SV40, polyoma virus, adenovirus, or bovine papilloma virus (BPV). In order to amplify the gene copy number in the host cell system, the expression vector can have, for example, the aminoglycoside phosphotransferase (APH) gene, thymidine kinase (TK) gene, *E. coli* xanthine guanine phosphoribosyltransferase (Ecogpt) gene, or dihydrofolate reductase (dhfr) gene inserted as a selection marker.

Any expression system, for example, a eukaryotic cell system or a prokaryotic cell system, can be used to produce antibodies used in the present invention. Examples of eukaryotic cells include animal cells such as established mammalian cell system, insect cell system, and filamentous fungus cells and yeast cells. Examples of prokaryotic cells include bacterial cells such as *E. coli* cells. Antibodies used in the present invention are preferably expressed in mammalian cells such as CHO, COS, myeloma, BHK, Vero, or HeLa cells.

Next, the transformed host cell is then cultured in vitro or in vivo to induce production of the antibody of interest. The host cells are cultured according to known methods. For example, DMEM, MEM, RPMI 1640, or IMDM can be used as the culture medium. A serum supplement solution such as fetal calf serum (FCS) can also be used in combination.

Antibodies expressed and produced as described above can be purified by using a single known method or a suitable combination of known methods generally used for purifying proteins. Antibodies can be separated and purified by, for example, appropriately selecting and combining affinity columns such as protein A column, chromatography column, filtration, ultrafiltration, salt precipitation, dialysis, and such (Antibodies A Laboratory Manual. Ed Harlow, David Lane, Cold Spring Harbor Laboratory, 1988).

Known means can be used to measure the antigen-binding activity of the antibodies (Antibodies A Laboratory Manual. Ed Harlow, David Lane, Cold Spring Harbor Laboratory, 1988). For example, an enzyme linked immunosorbent assay (ELISA), an enzyme immunoassay (EIA), a radioimmunoassay (RIA), or a fluoroimmunoassay can be used.

The antibodies used in the present invention may be antibodies with a modified sugar chain. It is known that the cytotoxic activity of an antibody can be increased by modifying its sugar chain. Antibodies having modified sugar chains are, for example, antibodies with modified glycosylation (for example, WO 99/54342), antibodies deficient in fucose which is added to sugar chains (for example, WO 00/61739 and WO 02/31140), antibodies having a sugar chain with bisecting GlcNAc (for example, WO 02/79255).

The antibodies used in the present invention are preferably antibodies having cytotoxic activity.

In the present invention, the cytotoxic activity includes, for example, antibody-dependent cell-mediated cytotoxicity (ADCC) activity and complement-dependent cytotoxicity (CDC) activity. In the present invention, CDC activity means cytotoxic activity caused by the complement system. ADCC activity refers to the activity of damaging a target cell when a specific antibody attaches to its cell surface antigen, and an Fcγ receptor-carrying cell (immune cell, or such) binds to the Fc portion of the antigen via the Fcγ receptor damages the target cell.

An anti-DSG3 antibody can be tested to see whether it has ADCC activity or CDC activity using known methods (for example, Current Protocols in Immunology, Chapter 7. Immunologic studies in humans, Editor, John E. Coligan et al., John Wiley & Sons, Inc., (1993) and the like).

First, specifically, effector cells, complement solution, and target cells are prepared.

(1) Preparation of Effector Cells

Spleen is removed from a CBA/N mouse or the like, and spleen cells are isolated in RPMI1640 medium (manufactured by Invitrogen). After washing in the same medium containing 10% fetal bovine serum (FBS, manufactured by HyClone), the cell concentration is adjusted to $5\times10^6$/mL to prepare the effector cells.

(2) Preparation of Complement Solution

Baby Rabbit Complement (manufactured by CEDARLANE) is diluted 10-fold in a culture medium (manufactured by Invitrogen) containing 10% FBS to prepare a complement solution.

(3) Preparation of Target Cells

The target cells can be radioactively labeled by incubating cells expressing the DSG3 protein (cells transformed with a gene encoding the DSG3 protein, lung cancer cells, colon cancer cells, esophageal cancer cells, gastric cancer cells, pancreatic cancer cells, skin cancer cells, uterine cancer cells, or the like) with 0.2 mCi of sodium chromate-$^{51}$Cr (manufactured by GE Healthcare Bio-Sciences) in a DMEM medium containing 10% FBS for one hour at 37° C. After radioactive labeling, cells are washed three times in RPMI1640 medium containing 10% FBS, and the target cells can be prepared by adjusting the cell concentration to $2\times10^5$/mL.

ADCC activity or CDC activity can be measured by the method described below. In the case of ADCC activity measurement, the target cell and anti-DSG3 antibody (50 µL each) are added to a 96-well U-bottom plate (manufactured by Becton Dickinson), and reacted for 15 minutes on ice. Thereafter, 100 µL of effector cells are added and incubated in a carbon dioxide incubator for four hours. The final concentration of the antibody is adjusted to 0 or 10 µg/mL.

After culturing, 100 μL of the supernatant is collected, and the radioactivity is measured with a gamma counter (COBRAII AUTO-GAMMA, MODEL D5005, manufactured by Packard Instrument Company). The cytotoxic activity (%) can be calculated using the obtained values according to the equation: $(A-C)/(B-C) \times 100$, wherein A represents the radioactivity (cpm) in each sample, B represents the radioactivity (cpm) in a sample where 1% NP-40 (manufactured by Nacalai Tesque) has been added, and C represents the radioactivity (cpm) of a sample containing the target cells only.

Meanwhile, in the case of CDC activity measurement, 50 μL of target cell and 50 μL of an anti-DSG3 antibody are added to a 96-well flat-bottomed plate (manufactured by Becton Dickinson), and reacted for 15 minutes on ice. Thereafter, 100 μL of complement solution is added, and incubated in a carbon dioxide incubator for four hours. The final concentration of the antibody is adjusted to 0 or 3 μg/mL. After incubation, 100 μL of supernatant is collected, and the radioactivity is measured with a gamma counter. The cytotoxic activity can be calculated in the same way as in the ADCC activity determination.

On the other hand, in the case of measuring the cytotoxic activity of an antibody conjugate, 50 μL of target cell and 50 μL of an anti-DSG3 antibody conjugate are added to a 96-well flat-bottomed plate (manufactured by Becton Dickinson), and reacted for 15 minutes on ice. Thereafter, this is incubated in a carbon dioxide incubator for one to four hours. The final concentration of the antibody is adjusted to 0 or 3 μg/mL. After culturing, 100 μL of supernatant is collected, and the radioactivity is measured with a gamma counter. The cytotoxic activity can be calculated in the same way as in the ADCC activity determination.

An antibody of the present invention having cytotoxic activity is more preferably an antibody that does not have cell-dissociating activity. An antibody that does not have cell-dissociating activity can be suitably selected and obtained by measuring the cell-dissociating activity that inhibits cell adhesion of keratinocytes even in a test tube. The method of measuring cell-dissociating activity can be carried out in a test tube, for example, by the method described in J. Invest. Dermatol., 124, 939-946, 2005. Furthermore, as a method for observing this cellular activity in vivo, the activity can be evaluated as the activity to induce PV lesions, which are phenotypes of in vivo cell-dissociating activity. The PV-lesion-inducing activity can be evaluated by the method described in J. Immunology 170, 2170-2178, 2003.

The cells whose proliferation is suppressed by the anti-DSG3 antibody are not particularly limited as long as they express a DSG3 protein, but are preferably cancer cells, and more preferably, lung cancer cells, colon cancer cells, esophageal cancer cells, gastric cancer cells, pancreatic cancer cells, skin cancer cells, or uterine cancer cells. More preferably, they are from non-small-cell lung cancer. Therefore, the anti-DSG3 antibody can be used for the purpose of treating or preventing diseases attributed to cell proliferation, for instance, lung cancer, colon cancer, esophageal cancer, stomach cancer, pancreatic cancer, skin cancer, or uterine cancer, more preferably non-small-cell lung cancer, and even more preferably lung squamous cell carcinoma, adenocarcinoma, adenosquamous carcinoma, or large cell carcinoma.

The present invention also provides polynucleotides encoding the antibodies of the present invention, and polynucleotides that hybridize under stringent conditions to these polynucleotides and encode antibodies having an activity equivalent to that of the antibodies of the present invention. The present invention also provides vectors containing these polynucleotides and transformants (including transformed cells) containing such vectors. The polynucleotides of the present invention are polymers comprising multiple nucleotides or base pairs of deoxyribonucleic acids (DNA) or ribonucleic acids (RNA), and are not particularly limited, as long as they encode the antibodies of the present invention. They may also contain non-natural nucleotides. The polynucleotides of the present invention can be used to express antibodies using genetic engineering techniques. Furthermore, they can be used as probes in the screening of antibodies that are functionally equivalent to the antibodies of the present invention. Specifically, a DNA that hybridizes under stringent conditions to the polynucleotide encoding an antibody of the present invention, and encodes an antibody having an activity equivalent to that of the antibody of the present invention, can be obtained by techniques such as hybridization and gene amplification technique (for example, PCR), using the polynucleotide encoding an antibody of the present invention, or a portion thereof, as a probe. Such DNAs are included in the polynucleotides of the present invention. Hybridization techniques are well known to those skilled in the art (Sambrook, J. et al., Molecular Cloning 2nd ed., 9.47-9.58, Cold Spring Harbor Lab. press, 1989). Conditions for hybridization include, for example, those with low stringency. Examples of conditions of low stringency include post-hybridization washing under conditions of 0.1×SSC and 0.1% SDS at 42° C., and preferably under conditions of 0.1×SSC and 0.1% SDS at 50° C. More preferable hybridization conditions include those of high stringency. Highly stringent conditions include, for example, conditions of 5×SSC and 0.1% SDS at 65° C. Under these conditions, the higher the temperature, polynucleotides having high homology would be obtained efficiently. However, several factors such as temperature and salt concentration can influence hybridization stringency, and those skilled in the art can suitably select these factors to realize similar stringencies.

An antibody that is encoded by a polynucleotide obtained by these hybridization and gene amplification techniques, and which is functionally equivalent to antibodies of the present invention, usually has a high homology to the amino acid sequences of these antibodies. The antibodies of the present invention also include antibodies that are functionally equivalent to and have high amino acid sequence homology to the antibodies of the present invention. The term "high homology" generally refers to amino acid identity of at least 50% or higher, preferably 75% or higher, more preferably 85% or higher, still more preferably 95% or higher. Polypeptide homology can be determined by the algorithm described in literature (Wilbur, W. J. and Lipman, D. J. Proc. Natl. Acad. Sci. USA (1983) 80, 726-730).

Pharmaceutical Compositions

In another aspect, the present invention features pharmaceutical compositions comprising an antibody that binds to a DSG3 protein as an active ingredient. In addition, the present invention features a cell proliferation inhibitor, in particular an anticancer agent, comprising an antibody that binds to a DSG3 protein as an active ingredient. Cell proliferation inhibitors and anticancer agents of the present invention are preferably administered to a subject affected by cancer, or to a subject who is likely to be affected by cancer. Subjects in the present invention are animal species that genetically carry a DSG3 protein and are affected by cancer or likely to be affected by cancer, and include, for example, mammals such as humans, monkeys, cattle, sheep, mice, dogs, cats, and hamsters, but are not limited thereto.

In the present invention, a cell proliferation inhibitor comprising as an active ingredient an antibody that binds to a DSG3 protein can also be described as a method for suppressing cell proliferation which comprises the step of administering an antibody that binds to a DSG3 protein to a subject, or as use of an antibody that binds to a DSG3 protein in the production of a cell proliferation inhibitor.

Furthermore, in the present invention, an anticancer agent comprising as an active ingredient an antibody that binds to a DSG3 protein can also be described as a method for preventing or treating cancer which comprises the step of administering an antibody that binds to a DSG3 protein to a subject, or as use of an antibody that binds to a DSG3 protein in the production of an anticancer agent.

In the present invention, the phrase "comprising an antibody that binds to DSG3 as an active ingredient" means comprising an anti-DSG3 antibody as the main active substance, and does not limit the content percentage of the anti-DSG3 antibody.

The antibody included in the pharmaceutical composition of the present invention (for example, cell proliferation inhibitor and anticancer agent; same hereinafter) is not particularly limited so long as it binds to a DSG3 protein, and examples include antibodies described herein.

The pharmaceutical compositions of the present invention can be administered orally or parenterally. Particularly preferably, the method of administration is parenteral administration, and specifically, the method of administration is, for example, administration by injection, transnasal administration, transpulmonary administration, or transdermal administration. Examples of administration by injection include systemic and local administrations of a pharmaceutical composition of the present invention by intravenous injection, intramuscular injection, intraperitoneal injection, subcutaneous injection, or such. A suitable administration method may be selected according to the age of the patient and symptoms. The dosage may be selected, for example, within the range of 0.0001 mg to 1000 mg per kg body weight in each administration. Alternatively, for example, the dosage for each patient may be selected within the range of 0.001 to 100,000 mg/body. However, the pharmaceutical composition of the present invention is not limited to these doses.

The pharmaceutical compositions of the present invention can be formulated according to conventional methods (for example, Remington's Pharmaceutical Science, latest edition, Mark Publishing Company, Easton, U.S.A), and may also contain pharmaceutically acceptable carriers and additives. Examples include, but are not limited to, surfactants, excipients, coloring agents, perfumes, preservatives, stabilizers, buffers, suspending agents, isotonization agents, binders, disintegrants, lubricants, fluidity promoting agents, and flavoring agents; and other commonly used carriers can be suitably used. Specific examples include light anhydrous silicic acid, lactose, crystalline cellulose, mannitol, starch, carmellose calcium, carmellose sodium, hydroxypropyl cellulose, hydroxypropyl methyl cellulose, polyvinylacetal diethylaminoacetate, polyvinylpyrrolidone, gelatin, medium chain fatty acid triglyceride, polyoxyethylene hardened castor oil 60, saccharose, carboxymethyl cellulose, corn starch, inorganic salt, and such.

In addition, the present invention provides methods for inducing damages in a DSG3-expressing cell and methods for inhibiting cell growth by contacting a DSG3-expressing cell with a DSG3 protein-binding antibody. The DSG3 protein-binding antibody is the same as the above-described antibody that binds to a DSG3 protein, which is to be contained in the cell growth inhibitor of the present invention. The cell that is bound by the anti-DSG3 antibody is not particularly limited as long as the cell is expressing DSG3, and is preferably a cancer cell, more preferably a lung cancer cell, a colon cancer cell, an esophageal cancer cell, a stomach cancer cell, a pancreatic cancer cell, a skin cancer cell, or a uterine cancer cell, and more preferably a non-small-cell lung cancer.

In the present invention "contacting" is accomplished, for example, by adding an antibody to a culture solution of DSG3-expressing cells cultured in a test tube. In this case, the antibody can be added in the form of, for example, a solution or a solid obtained by freeze-drying or the like. When adding the antibody as an aqueous solution, the aqueous solution used may purely contain only the antibody, or the solution may include, for example, the above-mentioned surfactants, excipients, coloring agents, perfumes, preservatives, stabilizers, buffers, suspending agents, isotonization agents, binders, disintegrants, lubricants, fluidity promoting agents, or flavoring agents. The concentration for addition is not particularly limited, but the final concentration in the culture that may be suitably used is preferably in the range of 1 pg/mL to 1 g/mL, more preferably 1 ng/mL to 1 mg/mL, and even more preferably 1 μg/mL to 1 mg/mL.

Furthermore, in another embodiment, "contacting" in the present invention is carried out by administration to a non-human animal to which a DSG3-expressing cell has been transplanted into the body, or to an animal carrying cancer cells endogenously expressing DSG3. The method of administration may be oral or parenteral administration. Particularly preferably, the method of administration is parenteral administration, and specifically, the method of administration is, for example, administration by injection, transnasal administration, transpulmonary administration, or transdermal administration. Examples of administration by injection include systemic and local administrations of pharmaceutical compositions, cell proliferation inhibitors and anticancer agents of the present invention by intravenous injection, intramuscular injection, intraperitoneal injection, subcutaneous injection, or such. A suitable administration method may be selected according to the age of the test animal and symptoms. When administering as an aqueous solution, the aqueous solution used may purely contain only the antibody, or the solution may include, for example, the above-mentioned surfactants, excipients, coloring agents, perfumes, preservatives, stabilizers, buffers, suspending agents, isotonization agents, binders, disintegrants, lubricants, fluidity promoting agents, or flavoring agents. The dosage may be selected, for example, within the range of 0.0001 mg to 1000 mg per kg body weight in each administration. Alternatively, for example, the dosage for each animal may be selected within the range of 0.001 to 100,000 mg/body. However, the antibody dose of the present invention is not limited to these doses.

The following method is suitably used as a method for evaluating or measuring cell damage induced by contacting DSG3-expressing cells with an anti-DSG3 antibody. Examples of a method for evaluating or measuring the cytotoxic activity in a test tube include methods for measuring the above-mentioned antibody-dependent cell-mediated cytotoxicity (ADCC) activity, complement-dependent cytotoxicity (CDC) activity, and such. Whether or not an anti-DSG3 antibody has ADCC activity or CDC activity can be measured by known methods (for example, Current protocols in Immunology, Chapter 7. Immunologic studies in humans, Editor, John E. Coligan et al., John Wiley & Sons, Inc., (1993) and the like). For activity measurements, a binding antibody having the same isotype as anti-DSG3 antibody but not having any cell-damaging activity can be used as a control antibody in the same manner as the anti-DSG3 antibody, and it can be determined that the activity is present when the anti-DSG3 antibody shows a stronger cytotoxic activity than the control antibody.

The isotype of an antibody is defined by the sequence of its H chain constant region in the antibody amino acid sequence, and is determined as a result of class switching that arises from genetic recombinations in chromosomes which occur during maturation of antibody-producing B-cells. Difference in isotype is reflected in the difference of physiological and pathological functions of antibodies, and for example, the strength of cytotoxic activity is known to be influenced by antibody isotype in addition to the expression level of the antigen. Therefore, when measuring the above-described cell damaging activity, an antibody of the same isotype as the test antibody is preferably used as the control.

A method for evaluating or measuring cell damaging activity in vivo is, for example, intradermally or subcutaneously transplanting DSG3-expressing cancer cells to a non-human test animal, and then intravenously or intraperitoneally administering a test antibody daily or at the interval of few days, starting from the day of transplantation or the following day. Cytotoxicity can be defined by daily measurement of tumor size. In a similar manner to the evaluation in a test tube, cytotoxicity can be determined by administering a control antibody having the same isotype, and observing that the tumor size in the anti-DSG3 antibody-administered group is significantly smaller than the tumor size in the control antibody-administered group. When using a mouse as the non-human test animal, it is suitable to use a nude (nu/nu) mouse whose thymus has been made genetically defective so that its T lymphocyte function is lost. The use of such a mouse can eliminate the participation of T lymphocytes in the test animals when evaluating or measuring the cytotoxicity of the administered antibody.

The following method can be used suitably as a method for evaluating or measuring the inhibitory effect of an anti-DSG3 antibody on proliferation of DSG3-expressing cells through contact. A method for measuring the incorporation of [$^3$H]-labeled thymidine added to the medium by living cells as an indicator for DNA replication ability is used as a method for evaluating or measuring the cell proliferation inhibitory activity in a test tube. As a more convenient method, a dye exclusion method that measures under a microscope the ability of a cell to exclude a dye such as trypan blue to outside, or the MTT method is used. The latter makes use of the ability of living cells to convert MTT (3-(4,5-dimethylthiazol-2-yl)-2,5-diphenyl tetrazolium bromide), which is a tetrazolium salt to a blue formazan product. More specifically, a test antibody is added to the culture solution of a test cell, and after a certain period of time passes, the MTT solution is added to the culture solution, and this is left to stand for a certain time for MTT to be incorporated into the cell. As a result, MTT which is a yellow compound is converted to a blue compound by the action of succinate dehydrogenase in the mitochondria of the cell. After dissolving this blue product for coloration, absorbance is measured and used as an indicator for the number of viable cells. Besides MTT, reagents such as MTS, XTT, WST-1, and WST-8 are commercially available (Nacalai Tesque, and such) and can be suitably used. For activity measurements, a binding antibody having the same isotype as the anti-DSG3 antibody but not having any cell proliferation inhibitory activity can be used as a control antibody in the same manner as the anti-DSG3 antibody, and it can be determined that the activity is present when the anti-DSG3 antibody has a stronger cell proliferation inhibitory activity than the control antibody.

For a method that evaluates or measures cell proliferation inhibiting activity in vivo, the same method as the one described above for evaluating or measuring cytotoxicity in vivo can be suitably used.

All prior art references cited herein are incorporated by reference into this description.

EXAMPLES

Herein below, the present invention will be specifically described with reference to the Examples, but it is not to be construed as being limited thereto.

[Example 1] DSG3 mRNA Expression Analysis in Various Types of Cancers

Gene chip was used to perform DSG3 gene expression analysis. To search for a gene whose expression is enhanced in cancer cells, various RNAs and total RNAs prepared from various extracted tissues by conventional methods using ISOGEN (manufactured by Nippon Gene) shown in Tables 1 and 2 were used. More specifically, gene expression analysis was carried out using 10 µg each of total RNAs, and subjecting them to GeneChip U-133A (manufactured by Affymetrix) according to the Expression Analysis Technical Manual (manufactured by Affymetrix). When analyzing lung adenocarcinoma and hepatocellular carcinoma, a total of 10 µg was obtained by combining total RNAs of twelve lung adenocarcinoma cases and three hepatocellular carcinoma cases to perform the analysis (Table 1).

TABLE 1

| Tissue | Source |
| --- | --- |
| Whole brain | Clontech 64020-1 |
| Lung | Clinical sample, 1 case |
| Trachea | Clontech 64091-1 |
| Heart | Ambion 7966 |
| Kidney | Ambion 7976 |
| Liver | Clinical sample (Surgery) |
| Pancreas | Ambion 7954 |
| Stomach | Clinical sample (Surgery) |
| Small intestine | Ambion 7984 |
| Large intestine | Ambion 7986 |
| Bone marrow | Clontech 64106-1 |
| Peripheral blood mononuclear cell | Clinical sample, 1 case |
| Testis | Clontech 64027-1 |
| Prostate | Ambion 7988 |
| Ovary | Ambion 7974 |
| Skin | Stratagene 735031 |
| Lung cancer (adenocarcinoma) | Clinical sample, 12 cases |
| Lung cancer (squamous cell carcinoma) | Clinical sample, 1 case |
| Lung cancer (squamous cell carcinoma) | Clinical sample, 1 case |
| Lung cancer (squamous cell carcinoma) | Clinical sample, 1 case |
| Lung cancer (squamous cell carcinoma) | Clinical sample, 1 case |
| Lung cancer (squamous cell carcinoma) | Clinical sample, 1 case |
| Liver cancer (moderately differentiated) | Clinical sample, 3 cases |
| Liver cancer (well differentiated) | Clinical sample, 3 cases |
| Colon cancer | Clinical sample, 1 case |
| Colon cancer | Clinical sample, 1 case |
| Colon cancer | Clinical sample, 1 case |

Tissues used for DSG3 gene expression analysis

TABLE 2

| Type of cancer | Cell line | Medium | Serum (%) |
|---|---|---|---|
| Brain tumor | U251 | DMEM | 10 |
| Breast cancer | MCF7 | RPMI1640 | 10 |
| Esophageal cancer | TE2 | RPMI1640 | 10 |
| Stomach cancer | AGS | RPMI1640 | 10 |
|  | GT3 | DMEM | 10 |
|  | KatoIII | RPMI1640:DMEM = 1:1 | 10 |
|  | MKN45 | RPMI1640 | 10 |
|  | MKN74 | RPMI1640 | 10 |
|  | 2M | DMEM | 10 |
|  | 2MD3 | DMEM | 10 |
| Colon cancer | CACO2 | DMEM | 20 |
|  | DLD1 | RPMI1640 | 10 |
|  | hCT116 | McCoy5A | 10 |
|  | LOVO | HamF12:DMEM = 1:1 | 10 |
|  | SW480 | RPMI1640 | 10 |
| Liver cancer | Alexander | DMEM | 10 |
|  | HepG2 | DMEM | 10 |
|  | HLE | DMEM | 10 |
|  | HuH6 | DMEM | 10 |
|  | HuH7 | DMEM | 10 |
| Pancreatic cancer | Capan1 | DMEM | 20 |
|  | KLM1 | RPMI1640 | 10 |
|  | Panc1 | RPMI1640 | 10 |
|  | Paca2 | RPMI1640 | 10 |
|  | PK-1 | RPMI1640 | 10 |
| Kidney cancer | Caki2 | RPMI1640 | 10 |
| Lung cancer | A549 | DMEM | 10 |
|  | Lu130 | RPMI1640 | 10 |
|  | H1359 | RPMI1640 | 10 |
|  | H157 | RPMI1640 | 10 |
|  | H1648 | HamF12:DMEM = 1:1 | 10 |
|  | H2009 | HamF12:DMEM = 1:1 | 10 |
|  | H23 | RPMI1640 | 10 |
|  | H2347 | RPMI1640 | 10 |
|  | H522 | RPMI1640 | 10 |
| Cervical cancer | Hela | DMEM | 10 |

Figure 2:
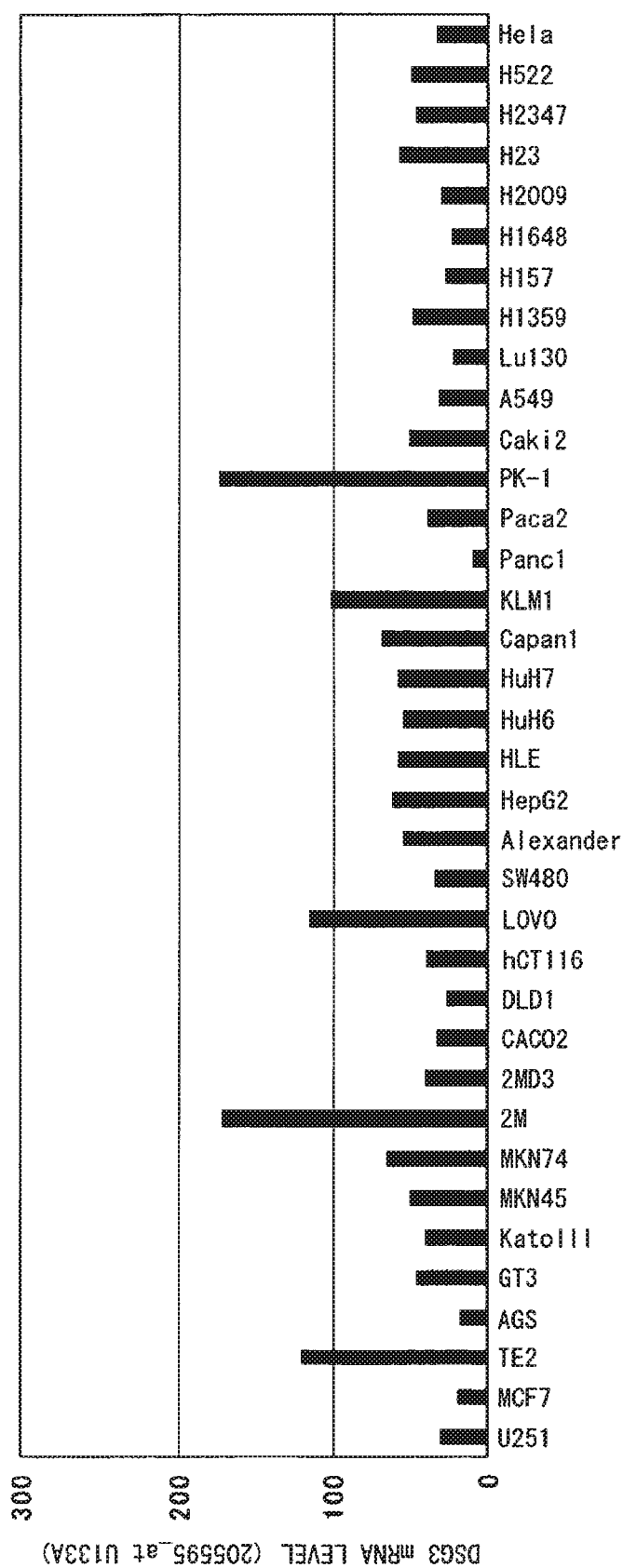
FIG. 2 depicts the result of DSG3 expression analysis in cancer cell lines using GeneChip U133.

Cancer cell lines and culturing conditions used for the DSG3 gene expression analysis Search for genes whose expression is enhanced in cancer tissues or cancer cells was performed by setting the mean value of the expression scores for all genes to 100, and comparing the relative expression levels of each gene. As a result, while expression of the DSG3 mRNA (probe ID: 205595 at HG-U133A) in normal tissues was limited to the skin, it was enhanced in lung cancer (lung squamous cell carcinoma) and colon cancer tissues, and in TE2 (esophageal cancer), 2M (stomach cancer), and PK-1 (pancreatic cancer) cancer cell lines (FIGS. 1 and 2).

From the above, it became apparent that while expression of the DSG3 gene (probe ID: 205595_at HG-U133A) is very low in normal tissues other than the skin, expression of the DSG3 gene is enhanced in a wide variety of cancers including lung cancer, colon cancer, esophageal cancer, stomach cancer, and pancreatic cancer. These results suggested that there is a high possibility that development of the above-mentioned cancers can be diagnosed using the DSG3 expression as an indicator.

[Example 2] Immunohistological Staining of DSG3 in Lung Squamous Cell Carcinoma

Since transcription of the DSG3 gene is enhanced in cancer cells, in particular, lung squamous cell carcinoma cells, immunohistological staining analysis was performed to confirm expression of the DSG3 protein.

Each sample was prepared as a fixed paraffin embedded preparation, and a section sliced to a thickness of 4 μm was mounted on a slide glass and then left at 37° C. for about 16 hours to dry sufficiently. The section was deparaffinized by soaking three times in 100% xylene for five minutes each, and then hydrophilized by soaking three times in 100% ethanol for five minutes each and further soaking in 70% ethanol for five minutes. Then, after washing three times in a 50 mM TBS buffer solution for five minutes, the antigen in the section was activated by treating the section with a citrate buffer (10 mM, pH 7.0) at 120° C. for ten minutes. The section in which the antigen had been activated was washed three times in a TBS buffer for five minutes each, and then treated for one hour at room temperature in a TBS buffer containing an anti-DSG3 antibody (5G11) (Zymed) diluted to a final concentration of 50 μg/mL. To inactivate the endogenous peroxidase, the anti-DSG3 antibody-bound section was treated with 0.3% hydrogen peroxide for 15 minutes at room temperature. After washing three times with a TBS buffer solution, the above-mentioned section was treated with the secondary antibody, ENVISION+kit/HRP (DAKO), for one hour at room temperature. After washing three times with the TBS buffer solution for five minutes each, DAB (3,3'-diaminobenzamide tetrahydrochloride) was added as a coloring substrate to stain the section. Hematoxylin was used as a staining agent for counter staining of the nucleus.

Figure 3:
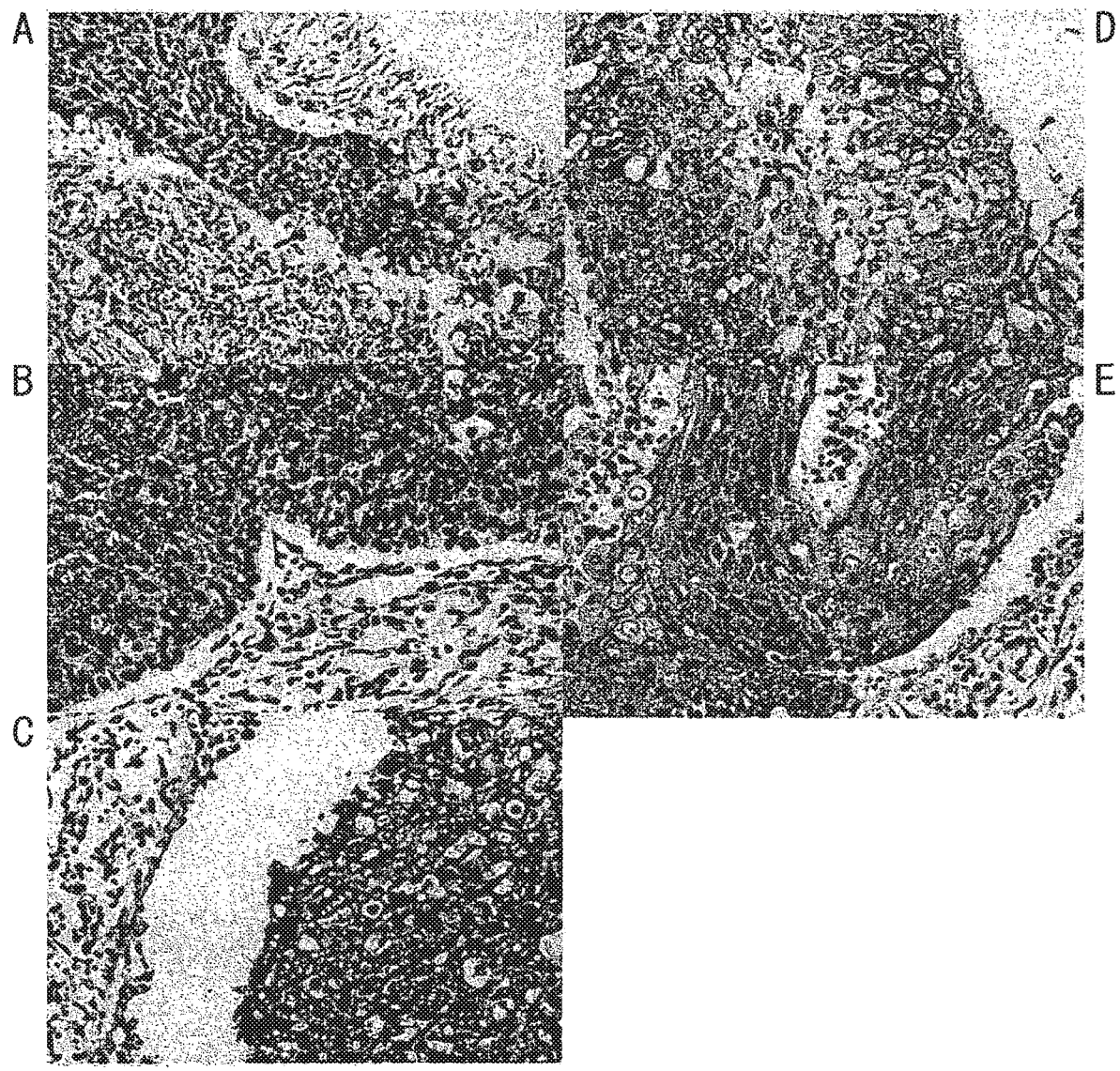
FIG. 3 shows photographs of immunohistological staining in which expression of the DSG3 protein in lung squamous cell carcinoma is visualized by immunostaining. Elevation of the DSG3 protein expression is shown in all five clinical samples.

As a result, of the five cases of tissue sections from cancer patients affected by lung squamous cell carcinoma, all five cases showed a positive reaction in which the section is stained by the anti-DSG3 antibody (5G11) (FIG. 3). Since a lung cancer-specific staining image was obtained, it became apparent that in lung cancer, the DSG3 expression is enhanced at the protein level as well. This indicated that development of lung cancer can be detected using an anti-DSG3 antibody.

[Example 3] Preparation of Anti-DSG3 Antibody 3-1) Cloning of a Full-Length cDNA Encoding Human DSG3

A full-length cDNA encoding human DSG3 was obtained by PCR amplification using Human Small Intestine Marathon-Ready cDNA (CLONTECH) as a template. Specifically, 50 μL of a reaction solution containing 2 μL of cDNA, 1 μL of sense primer (SEQ ID NO: 37), 1 μL of antisense primer (SEQ ID NO: 38), 5 μL of 10×KOD-Plus buffer, 5 μL of 2 mM dNTPs, 2 μL of 25 mM MgSO$_4$, and 1 μL of KOD-Plus was subjected to a PCR reaction performed by five cycles of a reaction cycle consisting of reactions at 94° C. for 15 seconds and 70° C. for two minutes, five cycles of a reaction cycle consisting of reactions at 94° C. for 15 seconds and 68° C. for two minutes, and 28 cycles of a reaction cycle consisting of reactions at 94° C. for 15 seconds and 66° C. for two minutes. The amplified product obtained by the above-mentioned PCR reaction was inserted into pGEM-T easy using a pGEM-T Easy Vector System I (Promega). This was sequenced using an ABI3730 DNA sequencer to confirm that the human DSG3-encoding cDNA sequence was successfully cloned. The sequence represented by SEQ ID NO: 39 shows the nucleotide sequence of the human DSG3 gene, and the sequence represented by SEQ ID NO: 40 shows the amino acid sequence of the human DSG3 protein.

3-2) Establishment of Cells Showing Constant Expression of Full-Length Human DSG3

The full-length human DSG3 cDNA was cloned into a vector (pMCN) for expression in mammalian cells (pMCN/hDSG3). pMCN enables induced expression under the control of a mouse CMV promoter (ACCESSION No. U68299), and is a vector into which a neomycin resistance gene has been incorporated. A CHO cell line that shows constant expression of full-length human DSG3 was established by introducing pMCN/hDSG3 into the CHO DG44 cell strain (Invitrogen) by electroporation, and subjecting them to selection with 500 μg/mL of Geneticin. Similarly, an A549 cell line that shows constant expression of full-length human DSG3 was established by introducing pMCN/hDSG3 into A549 cells (human lung epithelial cancer cell line) that do not show DSG3 expression, and selection with 1000 μg/mL of Geneticin.

3-3) Preparation of Soluble Human DSG3/Mouse IgG2a Fc-Fusion Protein

Soluble human DSG3/mouse IgG2a Fc-fusion protein (hereinafter, shDSG3_mIgG2aFc) was prepared as an immunizing antigen for anti-DSG3 antibody production. shDSG3_mIgG2aFc was prepared by linking the extracellular domain of human DSG3 (Met1-Leu616) with the mouse IgG2a constant region through the CpoI recognition sequence in the hinge region, and cloned into the pMCDN vector prepared by incorporating the DHFR gene to the pMCN expression vector (pMCDN/shDSG3_mIgG2aFc). The sequence represented by SEQ ID NO: 41 shows the nucleotide sequence of the shDSG3_mIgG2aFc gene, and the sequence represented by SEQ ID NO: 42 shows the amino acid sequence of shDSG3_mIgG2aFc. A CHO cell line that shows constant expression of shDSG3_mIgG2aFc was established by introducing pMCDN/shDSG3_mIgG2aFc into DG44 cells by electroporation, and selection with 500 μg/mL of Geneticin. Next, shDSG3_mIgG2aFc was purified from culture supernatant of the established shDSG3_mIgG2aFc-expressing CHO cell line. The culture supernatant was applied to a Hi Trap Protein G HP (GE Healthcare Bio-Sciences) column, and after washing with a binding buffer (20 mM sodium phosphate (pH 7.0)), elution was carried out using an elution buffer (0.1 M glycine-HCl (pH 2.7)). The eluate was immediately neutralized by elution into a tube containing a neutralization buffer (1 M Tris-HCl (pH 9.0)). This eluate was subjected to gel filtration using Superdex 200 HR 10/30 (GE Healthcare Bio-Sciences) so that the solvent of the solution containing the desired antibody is replaced by a PBS buffer. The purified protein was quantified using a DC protein assay kit (BIO-RAD) and converted into a concentration using bovine IgG included in the kit as standard preparation.

3-4) Preparation of Anti-DSG3 Antibody

Balb/c mice or MRL/MpJUmmCrj-lpr/lpr mice (hereinafter MRL/lpr mice, purchased from Charles River Japan) were used as the animals for immunization. Immunization was initiated at the 7$^{th}$ week or 8th week. For the first immunization, an antigen was prepared using a PBS buffer so as to include 100 μg of shDSG3_mIgG2aFc for each mouse, emulsified using Freund's complete adjuvant (Beckton Dickinson), and administered subcutaneously. Two weeks later, an antigen was prepared using a PBS buffer so as to include 50 μg for each mouse, emulsified using Freund's incomplete adjuvant (Beckton Dickinson), and administered subcutaneously. Subsequently, boosting immunization was performed at 1-week intervals for two to four times, and for the final immunization, the antigen was diluted in PBS at 50 μg/mouse, and then administered into the tail vein. Four days after the final immunization, spleen cells were extirpated and mixed with mouse myeloma cells P3-X63Ag8U1 (P3U1, purchased from ATCC) at 2:1 ratio, and cell fusion was carried out by gradual addition of PEG 1500 (Roche Diagnostics). Next, RPMI1640 medium (Invitrogen) was added carefully to dilute PEG 1500, and then PEG 1500 was removed by centrifuging and removing the supernatant. The group of fused cells suspended in RPMI1640 containing 10% FBS was seeded into a 96-well culture plate at 100 μL/well. The following day, RPMI1640 containing 10% FBS, 1x HAT media supplement (SIGMA), and 0.5×BM-Condimed H1 Hybridoma cloning supplement (Roche Diagnostics) (hereinafter referred to as HAT medium) was added at 100 μL/well. On the second or third day, half of the culture solution was replaced with HAT medium, and the culture supernatant from the seventh day was used in the screening in which binding activity to the DSG3 molecule was used as an indicator. The screening was performed by flow cytometric analysis which detects binding to CHO cells that show constant expression of full-length human DSG3. Positive clones obtained by this analysis were monocloned by the limiting dilution method. Specifically, DF120, DF122, DF148, DF151, DF153, DF168, DF331, DF364, and DF366 were established as antibodies that specifically bind to DSG3.

In a similar manner to the case with shDSG3_mIgG2aFc, the monoclonal antibodies were purified using a Hi Trap Protein G HP column, from the culture supernatant of hybridomas cultured in HAT medium that uses FBS (Ultra low IgG) (Invitrogen) as the serum. The eluted fractions were subjected to solvent replacement with PBS using a PD-10 column (GE Healthcare Bio-Sciences), and then stored at 4° C. The purified antibodies were quantified using a DC protein assay kit (BIO-RAD) and converted into concentration using bovine IgG included in the kit as the standard preparation.

3-5) Evaluation of Binding Activity by Flow Cytometry

Figure 4:
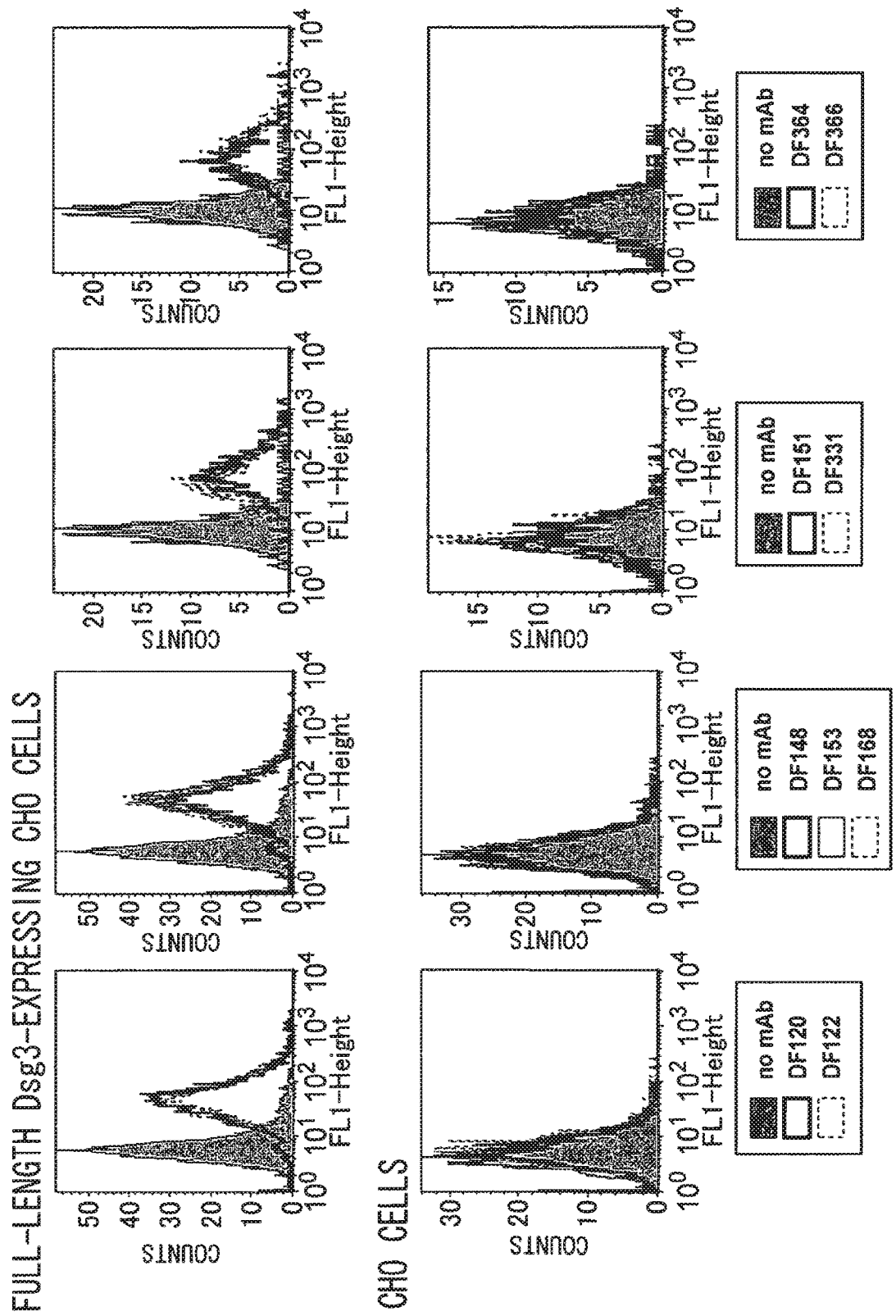
FIG. 4 depicts the result of flow cytometric analysis which shows binding of all the anti-DSG3 monoclonal antibodies DF120, DF122, DF148, DF151, DF153, DF168, DF331, DF364, and DF366 to a CHO cell line that constitutively expresses full-length DSG3.

Flow cytometry was used to evaluate the binding of the obtained antibodies to CHO cells that show constant expression of full-length human DSG3. The cells were suspended in FACS Buffer (1% FBS/PBS) at $5 \times 10^5$ cells/mL and dispensed into Multiscreen-HV Filter Plates (Millipore), and the supernatant was removed from this cell suspension solution by centrifugation. After adding to the supernatant-free cells an FACS buffer containing anti-DSG3 monoclonal antibodies which have been diluted to a suitable concentration (3 μg/mL) in the FACS buffer, this was left to stand for 30 minutes on ice to let the cells react with the monoclonal antibodies. After removing the supernatant from this reaction solution by centrifugation, the cells were washed once with FACS buffer. Next, by suspending the cells in a FACS buffer containing FITC-labeled anti-mouse IgG antibody as the secondary antibody, the cells were reacted with the secondary antibody for 30 minutes on ice. After the reaction was completed, the supernatant was removed from the cells by centrifugation. The cells were suspended in 100 μL of FACS buffer, and then subjected to flow cytometric analysis. FACS Calibur (Becton Dickinson) was used as the flow cytometer. The living cell population was gated to a histogram of forward scatter and side scatter. As shown in FIG. 4, 3 μg/mL of anti-DSG3 monoclonal antibodies (DF120, DF122, DF148, DF151, DF153, DF168, DF331, DF364, and DF366) bound strongly to the DSG3-expressing CHO cells and did not bind to the parent CHO cells, indicating that the anti-DSG3 monoclonal antibodies specifically bind to DSG3 present on the cell membrane.

[Example 4] Measurement of Cytotoxic Activities of the Anti-DSG3 Antibodies 4-1) Measurement of Complement-Dependent Cytotoxicity (CDC) Activities of the Anti-DSG3 Antibodies The CHO cell line showing constant expression of full-length human DSG3 (DSG3-CHO, described in Example 3-2)) was used as the target cell. CHO-S-SFM II medium (Invitrogen) containing 500 μg/mL Geneticin (Invitrogen), HT supplement (Invitrogen), and penicillin/streptomycin (Invitrogen) (hereinafter referred to as "medium") was used to culture the DSG3-CHO cell line. The cell pellet obtained by centrifuging $5 \times 10^5$ DSG3-CHO cell line cells (1000 rpm) for five minutes at 4° C. was suspended in approximately 200 μL of medium containing 3.7 MBq of Chromium-51 (GE Healthcare Bio-Sciences), and then cultured in a 5% carbon dioxide incubator for one hour at 37° C. These cells were washed three times with the medium, then adjusted to cell density of $1 \times 10^5$ cells/mL in the medium, and then dispensed into a 96-well flat-bottomed plate at 100 μL/well. Next, the anti-DSG3 antibodies and a control mouse IgG2a antibody (BD Biosciences Pharmingen) diluted with the medium were individually added at 50 μL/well. The final concentration of the antibodies was adjusted to 10 μg/mL. Next, baby rabbit complement (Cedarlane) diluted 5-fold in the medium was added at 50 μL/well, and then the plate was left to stand in a 5% carbon dioxide incubator for 1.5 hours at 37° C. Thereafter, this was centrifuged (1000 rpm) for five minutes at 4° C., 100 μL of the supernatant was collected from each well of the plate, and the radioactivity was measured using a gamma counter (1480 WIZARD 3", Wallac). The specific chromium release rate was determined based on the following equation:

$$\text{Specific chromium release rate (\%)} = (A-C) \times 100/(B-C)$$

where A represents the radioactivity (cpm) in each well, B represents the mean value of radioactivity (cpm) in wells where 100 μL of the cells and 100 μL of 2% Nonidet P-40 solution (Nacalai Tesque) have been added, and C represents the mean value of radioactivity (cpm) in wells where 100 μL of the cells and 100 μL of the medium have been added. The measurements were conducted in duplicate, and the mean value and standard deviation were calculated for the specific chromium release rate.

Figure 5:
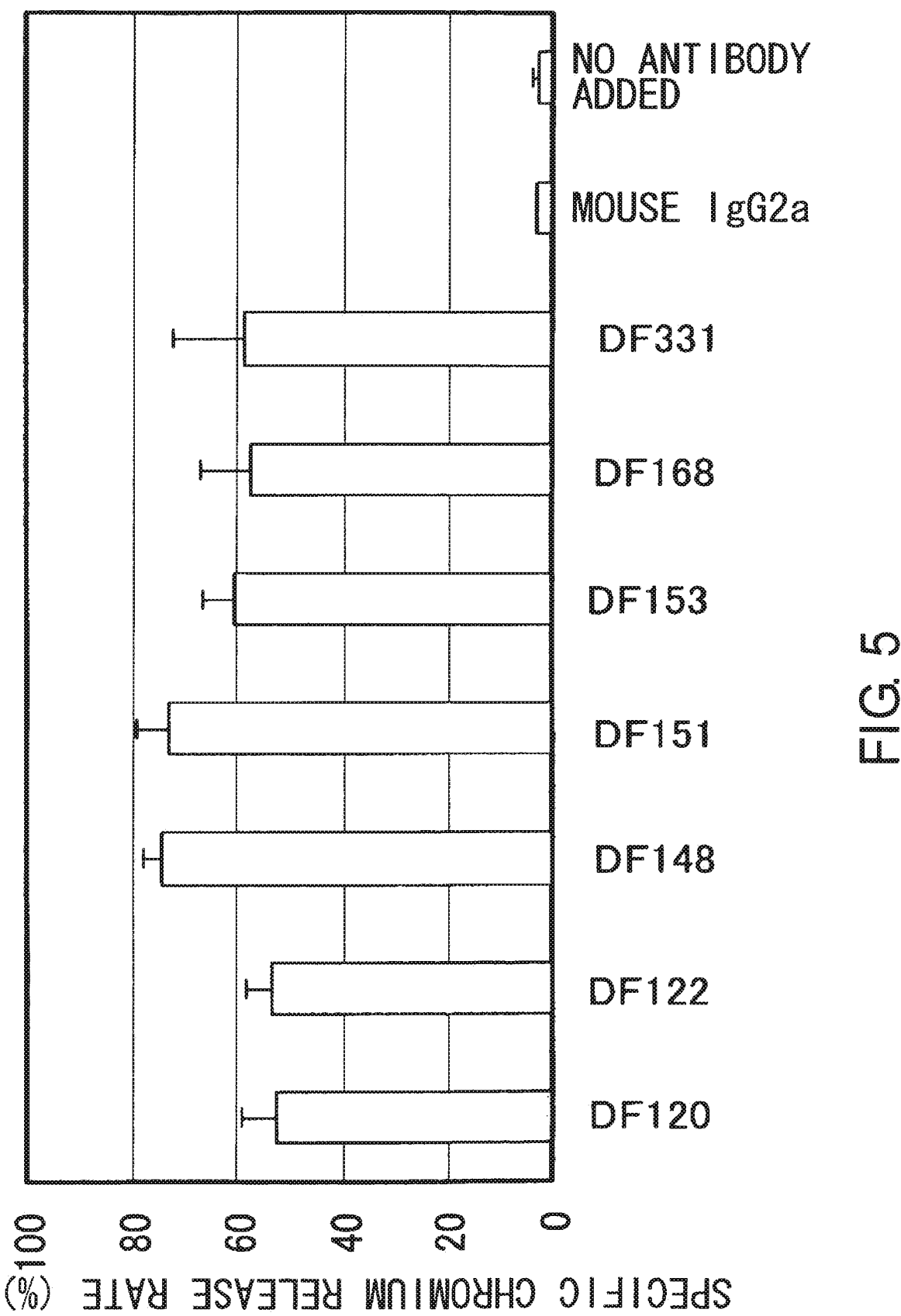
FIG. 5 depicts the CDC activity of anti-DSG3 monoclonal antibodies DF120, DF122, DF148, DF151, DF153, DF168, and DF331 towards a CHO cell line that constitutively expresses full-length DSG3.

All of the anti-DSG3 antibodies used in the experiment were confirmed to have CDC activity (FIG. 5). On the other hand, the control mouse IgG2a antibody did not show CDC activity at the same concentration.

Next, human epidermoid carcinoma cell line A431 (purchased from ATCC), human lung epithelial cancer cell line A549 (purchased from ATCC), and an A549 cell line showing constant expression of full-length human DSG3 (DSG3-A549, described in Example 3-2)) were used as target cells to examine whether the antibodies have CDC activity. A431 and DSG3-A549 express DSG3 on the cell membrane. Dulbecco's Modified Eagle Medium (Invitrogen) (hereinafter referred to as DMEM medium) containing 10% fetal bovine serum (Invitrogen) and penicillin/streptomycin was used to culture A431 and A549. DMEM medium containing 1 mg/mL Geneticin was used to culture the DSG3-A549 cell line. A431, A549, and DSG3-A549 cells were individually added to a 96-well flat-bottomed plate at $2 \times 10^3$ cells/well (A549 and DSG3-A549) or $4 \times 10^3$ cells/well (A431), and cultured in a 5% carbon dioxide incubator for three days at 37° C. After culturing, Chromium-51 was added at a final concentration of 1.85 MBq/mL, and culturing was continued for another hour. Each well was washed with 300 μL of DMEM medium, and then 100 μL of DMEM medium was added. Next, specific chromium release rates were determined by adding an anti-DSG3 antibody and baby rabbit complement under conditions similar to those used for the examination using DSG3-CHO cell line.

Figure 6:
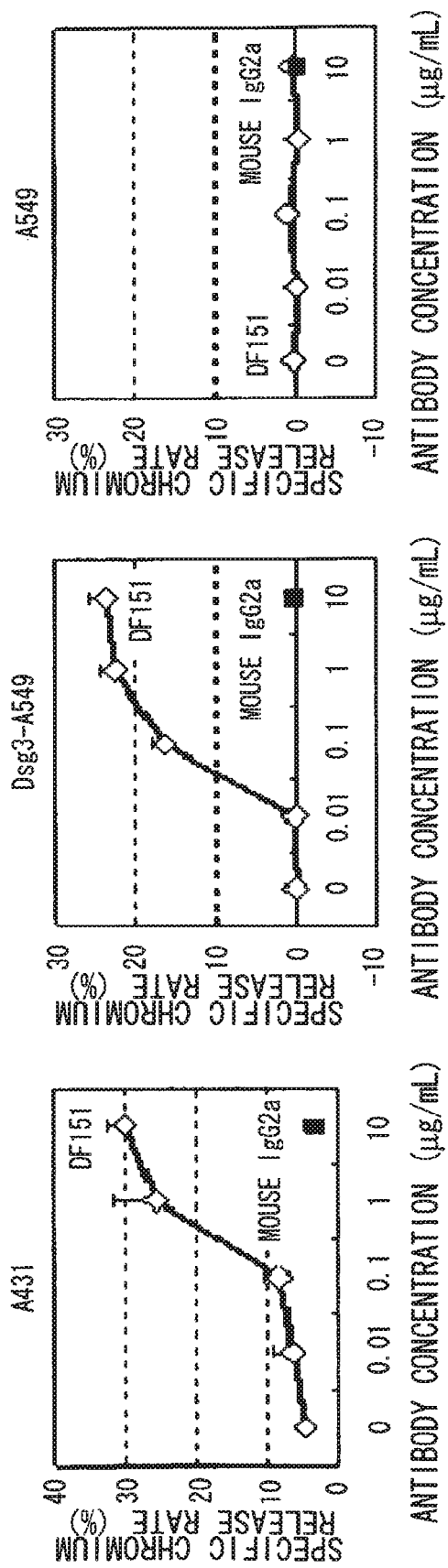
FIG. 6 depicts the CDC activity of the DF151 anti-DSG3 monoclonal antibody towards the human epidermoid carcinoma cell line A431, and the DSG3-A549 cell line, which is a human lung carcinoma cell line that constitutively expresses DSG3.

Anti-DSG3 antibody DF151 induced concentration-dependent CDC activity against DSG3-expressing A431 and DSG3-A549 cell lines, but did not show CDC activity against A549 cell line which does not express DSG3 (FIG. 6). These results showed that the anti-DSG3 antibody exhibits antigen-specific CDC activity.

4-2) Measurement of Antibody-Dependent Cellular Cytotoxicity (ADCC) Activity of Anti-DSG3 Antibodies DSG3-A549 cell line and A431 cell line were used for ADCC activity measurements. Similar to the case of CDC activity measurements, the above-mentioned cells were cultured in a 96-well flat-bottomed plate and then reacted with Chromium-51. Thereafter, each well was washed with RPMI1640 medium (Invitrogen) containing 10% fetal bovine serum and penicillin/streptomycin (hereinafter referred to as RPMI medium), and then 100 μL of RPMI medium was added. Next, 50 μL each of an anti-DSG3 antibody and the control mouse IgG2a antibody diluted in RPMI medium was added to each well. The final concentration of the antibody was adjusted to 10 μg/mL (bone marrow-derived effector cells) or 1 μg/mL (spleen-derived effector cells). Next, 50 μL of an effector cell solution ($1 \times 10^7$ cells/mL), which will be described later, was added to each well, and then the plate was left to stand in a 5% carbon dioxide incubator for four hours at 37° C. Specific chromium release rate was determined from the measured radioactivity of each well in this plate. Cells obtained by culturing the spleen cells of a Balb/c mouse (Charles River Japan) in RPMI medium containing 50 ng/mL recombinant human interleukin-2 (Peprotech) for five days or cells obtained by culturing the bone marrow cells of the same mouse in RPMI medium containing 50 ng/mL of recombinant human interleukin-2 and 10 ng/mL of recombinant mouse GM-CSF (Peprotech) for six days were used as effector cells.

Figure 7:
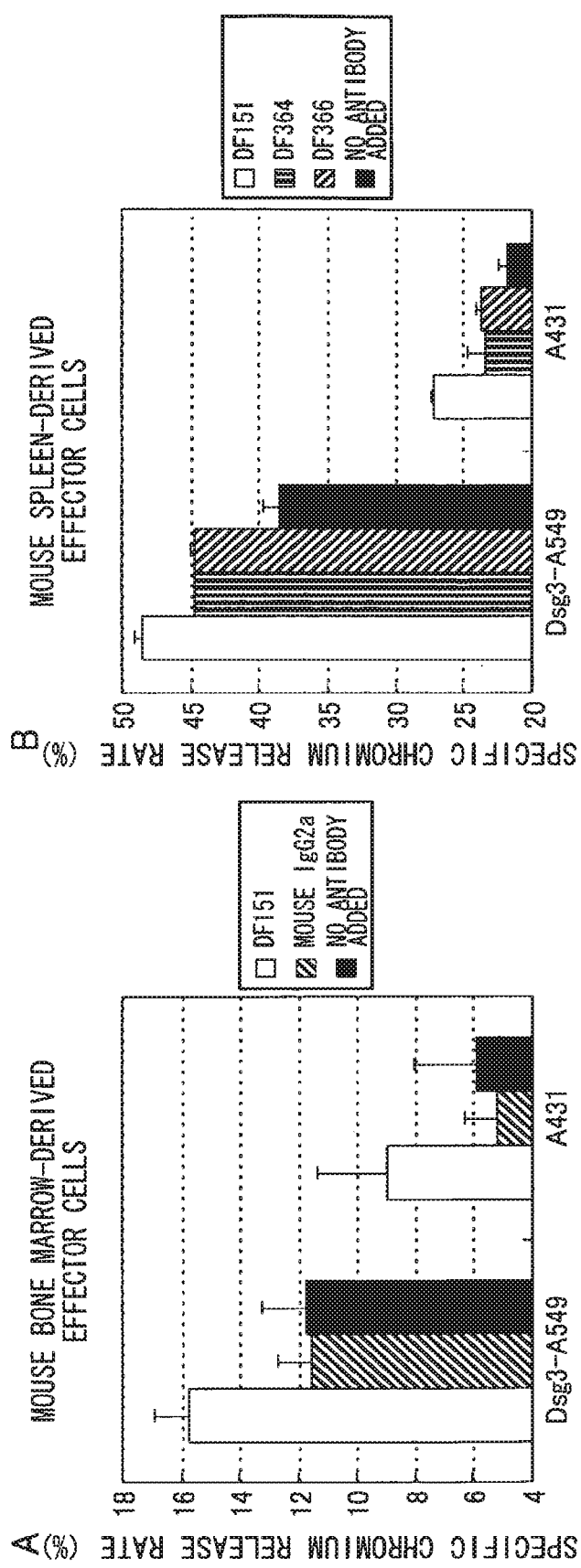
FIG. 7 depicts the ADCC activity of anti-DSG3 monoclonal antibodies DF151, DF364, and DF366 towards the DSG3-A549 cell line which is a human lung carcinoma cell line that constitutively expresses DSG3.

Anti-DSG3 antibodies DF151, DF364, and DF366 induced ADCC against DSG3-A549 and A431 cell lines (FIG. 7). The above-mentioned results showed that anti-DSG3 antibodies induce cell damage in DSG3 protein-expressing cells through ADCC activity.

[Example 5] Determination of the Anti-DSG3 Antibody Variable-Region Gene Sequences Antibody variable region genes were cloned from hybridomas that produce monoclonal antibodies DF151, DF364, and DF366, which are antibodies showing ADCC activity and CDC activity in DSG3-expressing cells, and their sequences were determined. Antibody genes encoding monoclonal antibodies DF151, DF364, and DF366 were amplified by the RT-PCR method using total RNAs extracted from the anti-DSG3 antibody-producing hybridomas. Total RNA was extracted from $1 \times 10^7$ hybridoma cells using the RNeasy Plant Mini Kit (QIAGEN). Using 1 μg of total RNA, the 5'-end gene fragment was amplified by the SMART RACE cDNA Amplification Kit (CLONTECH), using synthetic oligonucleotide MHC-IgG2b (SEQ ID NO: 43) complementary to the mouse IgG2b constant region sequence, synthetic oligonucleotide MHC-IgG1 (SEQ ID NO: 100) complementary to the mouse IgG1 constant region sequence, or synthetic oligonucleotide kappa (SEQ ID NO: 44) complementary to the mouse κ chain constant region nucleotide sequence. The reverse transcription reaction was performed for one hour and thirty minutes at 42° C. The PCR reaction was performed in 504 of PCR reaction solution containing 5 μL of 10× Advantage 2 PCR Buffer, 5 μL of 10× Universal Primer A Mix, 0.2 mM dNTPs (dATP, dGTP, dCTP, and dTTP), 1 μL of Advantage 2 Polymerase Mix (the above were manufactured by CLONTECH), 2.5 μL of reverse transcription reaction product, and 10 pmol of synthetic oligonucleotide MHC-IgG2b, MHC-IgG1, or kappa. The PCR reaction was performed under the reaction conditions of reaction at an initial temperature of 94° C. for 30 seconds, followed by five cycles of a reaction cycle consisting of reactions at 94° C. for 5 seconds and 72° C. for three minutes, five cycles of a reaction cycle consisting of reactions at 94° C. for 5 seconds, 70° C. for 10 seconds, and 72° C. for three minutes, and 25 cycles of a reaction cycle consisting of reactions at 94° C. for five seconds, 68° C. for ten seconds, and 72° C. for three minutes. Finally, the reaction product was heated at 72° C. for seven minutes. Each PCR product was purified from agarose gel using the QIAquick Gel Extraction Kit (manufactured by QIAGEN), then cloned into pGEM-T Easy vector (manufactured by Promega), and the nucleotide sequence of the clone was determined.

For the H chain of DF151, the nucleotide sequence and amino acid sequence of CDR1 are shown in SEQ ID NO: 1 and SEQ ID NO: 2, respectively, the nucleotide sequence and amino acid sequence of CDR2 are shown in SEQ ID NO: 3 and SEQ ID NO: 4, respectively, and the nucleotide sequence and amino acid sequence of CDR3 are shown in SEQ ID NO: 5 and SEQ ID NO: 6, respectively. For the L chain of DF151, the nucleotide sequence and amino acid sequence of CDR1 are shown in SEQ ID NO: 11 and SEQ ID NO: 12, respectively, the nucleotide sequence and amino acid sequence of CDR2 are shown in SEQ ID NO: 13 and SEQ ID NO: 14, respectively, and the nucleotide sequence and amino acid sequence of CDR3 are shown in SEQ ID NO: 15 and SEQ ID NO: 16, respectively.

For the H chain of DF364, the nucleotide sequence and amino acid sequence of CDR1 are shown in SEQ ID NO: 21 and SEQ ID NO: 22, respectively, the nucleotide sequence and amino acid sequence of CDR2 are shown in SEQ ID NO: 23 and SEQ ID NO: 24, respectively, and the nucleotide sequence and amino acid sequence of CDR3 are shown in SEQ ID NO: 25 and SEQ ID NO: 26, respectively. For the L chain of DF364, the nucleotide sequence and amino acid sequence of CDR1 are shown in SEQ ID NO: 29 and SEQ ID NO: 30, respectively, the nucleotide sequence and amino acid sequence of CDR2 are shown in SEQ ID NO: 31 and SEQ ID NO: 32, respectively, and the nucleotide sequence and amino acid sequence of CDR3 are shown in SEQ ID NO: 33 and SEQ ID NO: 34, respectively.

For the H chain of DF366, the nucleotide sequence and amino acid sequence of CDR1 are shown in SEQ ID NO: 80 and SEQ ID NO: 81, respectively, the nucleotide sequence and amino acid sequence of CDR2 are shown in SEQ ID NO: 82 and SEQ ID NO: 83, respectively, and the nucleotide sequence and amino acid sequence of CDR3 are shown in SEQ ID NO: 84 and SEQ ID NO: 85, respectively. For the L chain of DF366, the nucleotide sequence and amino acid sequence of CDR1 are shown in SEQ ID NO: 86 and SEQ ID NO: 87, respectively, the nucleotide sequence and amino acid sequence of CDR2 are shown in SEQ ID NO: 88 and SEQ ID NO: 89, respectively, and the nucleotide sequence and amino acid sequence of CDR3 are shown in SEQ ID NO: 90 and SEQ ID NO: 91, respectively.

For DF151, the nucleotide sequence and the amino acid sequence of the H-chain variable region are shown in SEQ ID NO: 45 and SEQ ID NO: 46, respectively, and the nucleotide sequence and the amino acid sequence of the L-chain variable region are shown in SEQ ID NO: 47 and SEQ ID NO: 48, respectively. For DF364, the nucleotide sequence and the amino acid sequence of the H-chain variable region are shown in SEQ ID NO: 49 and SEQ ID NO: 50, respectively, and the nucleotide sequence and the amino acid sequence of the L-chain variable region are shown in SEQ ID NO: 51 and SEQ ID NO: 52, respectively. For DF366, the nucleotide sequence and the amino acid sequence of the H-chain variable region are shown in SEQ ID NO: 92 and SEQ ID NO: 93, respectively, and the nucleotide sequence and the amino acid sequence of the L-chain variable region are shown in SEQ ID NO: 94 and SEQ ID NO: 95, respectively.

[Example 6] Determination of Full-Length Gene Sequences of Anti-DSG3 Antibodies

When the variable region gene sequences of DF151, DF364, and DF366 were determined, the gene sequences of the constant regions adjacent to the variable regions were also determined. By searching for genes that have the same sequences as these sequences using the Basic Local Alignment Search Tool (BLAST) of the National Center for Biotechnology Information (http://www.ncbi.nlm.nih.gov/BLAST/), the nucleotide sequences of the entire constant regions can be obtained. The full-length nucleotide sequence can be determined by linking the obtained nucleotide sequence of the constant region to the variable region nucleotide sequence. In this manner, the mouse IgG2b nucleotide sequence (DDBJ Accession No. BC025447), mouse kappa light chain nucleotide sequence (DDBJ Accession No. AY704179), and mouse IgG1 nucleotide sequence (DDBJ Accession No. BC057688) can be obtained from the nucleotide sequence of the H-chain constant region of DF151 (SEQ ID NO: 53), the nucleotide sequence of the L-chain constant region of DF151, DF364, and DF366 (SEQ ID NO: 54), and the nucleotide sequence of the H-chain constant region of DF364 and DF366 (SEQ ID NO: 55), respectively.

The isotypes of DF151 (mouse IgG2bκ), DF364 (mouse IgG1κ), and DF366 (mouse IgG1κ) were determined in advance using the IsoStrip Mouse Monoclonal Antibody Isotyping Kit (ROCHE). The predicted nucleotide sequence and amino acid sequence of the full-length DF151 H chain are shown in SEQ ID NO: 56 and SEQ ID NO: 57, respectively, and the predicted nucleotide sequence and amino acid sequence of the full-length DF151 L chain are shown in SEQ ID NO: 58 and SEQ ID NO: 59, respectively. The predicted nucleotide sequence and amino acid sequence of the full-length DF364 H chain are shown in SEQ ID NO: 60 and SEQ ID NO: 61, respectively, and the predicted nucleotide sequence and amino acid sequence of the full-length DF364 L chain are shown in SEQ ID NO: 62 and SEQ ID NO: 63, respectively. The predicted nucleotide sequence and amino acid sequence of the full-length DF366 H chain are shown in SEQ ID NO: 101 and SEQ ID NO: 102, respectively, and the predicted nucleotide sequence and amino acid sequence of the full-length DF366 L chain are shown in SEQ ID NO: 103 and SEQ ID NO: 104, respectively. For DF151, the nucleotide sequence and the amino acid sequence of the H-chain constant region are shown in SEQ ID NO: 7 and SEQ ID NO: 8, respectively, and the nucleotide sequence and the amino acid sequence of the L-chain constant region are shown in SEQ ID NO: 17 and SEQ ID NO: 18, respectively. For DF364 and DF366, the nucleotide sequence and the amino acid sequence of the H-chain constant region are shown in SEQ ID NO: 27 and SEQ ID NO: 28, respectively, and the nucleotide sequence and the amino acid sequence of the L-chain constant region are shown in SEQ ID NO: 35 and SEQ ID NO: 36, respectively.

[Example 7] Production of Anti-DSG3 Mouse-Human Chimeric Antibodies

The H-chain and L-chain variable region sequences of each antibody were ligated in frame with human H-chain and L-chain constant region sequences. PCR was performed using a synthetic oligonucleotide having a sequence complementary to a Kozak sequence and an EcoRI site at the 5' end of a nucleotide sequence encoding the H-chain variable region, and a synthetic oligonucleotide complementary to the 3' end nucleotide sequence which has a NheI site inserted. PCR was performed using a synthetic oligonucleotide having a sequence complementary to a Kozak sequence and a BamHI site at the 5' end of a nucleotide sequence encoding the L-chain variable region, and a synthetic oligonucleotide complementary to the 3' end nucleotide sequence which has a BsiWI site inserted. The obtained PCR products were cloned into antibody expression plasmid pMCDN_G1k. pMCDN_G1k has the human IgG1 constant region (the nucleotide sequence is shown in SEQ ID NO: 9 and the amino acid sequence is shown in SEQ ID NO: 10) cloned into the pMCDN vector, and has a structure in which the mouse H-chain variable region and the human H-chain (γ1 chain) constant region are linked by a NheI site. Furthermore, another expression unit comprising a mouse CMV promoter, and a human κ constant region (the nucleotide sequence is shown in SEQ ID NO: 19, and the amino acid sequence is shown in SEQ ID NO: 20) are inserted, and it has a structure in which the mouse L-chain variable region and human L chain (κ chain) constant region are linked by a BsiWI site. This plasmid expresses the neomycin resistance gene, DHFR gene, and anti-DSG3 mouse-human chimeric antibody gene in animal cells.

pMCDN_G1k DF151, pMCDN_G1k_DF364, and pMCDN_G1k_DF366 prepared as described above were introduced into DG44 cells by electroporation. Geneticin selection (500 μg/mL) established CHO cells that show constant expression of DF151 mouse-human chimeric antibody (hereinafter referred to as DF151c), DF364 mouse-human chimeric antibody (hereinafter referred to as DF364c), and DF366 mouse-human chimeric antibody (hereinafter referred to as DF366c). Next, the anti-DSG3 mouse-human chimeric antibodies were purified from the culture supernatants of the CHO cells using a Hi Trap rProtein A column (GE Healthcare Bio-Sciences). The purified antibodies were subjected to buffer replacement with PBS buffer using PD-10 columns (GE Healthcare Bio-Sciences), quantified by DC Protein Assay, and then stored at 4° C. The purified anti-DSG3 mouse-human chimeric antibodies were subjected to flow cytometric analysis to confirm that they bind specifically to DSG3 in the same way as the mouse antibodies. The nucleotide sequence and amino acid sequence of the full-length DF151c H chain are shown in SEQ ID NO: 64 and SEQ ID NO: 65, respectively, and the nucleotide sequence and amino acid sequence of the full-length DF151c L chain are shown in SEQ ID NO: 66 and SEQ ID NO: 67, respectively. The nucleotide sequence and amino acid sequence of the full-length DF364c H chain are shown in SEQ ID NO: 68 and SEQ ID NO: 69, respectively, and the nucleotide sequence and amino acid sequence of the full-length DF364c L chain are shown in SEQ ID NO: 70 and SEQ ID NO: 71, respectively. The nucleotide sequence and amino acid sequence of the full-length DF366c H chain are shown in SEQ ID NO: 96 and SEQ ID NO: 97, respectively, and the nucleotide sequence and amino acid sequence of the full-length DF366c L chain are shown in SEQ ID NO: 98 and SEQ ID NO: 99, respectively.

[Example 8] Production of Low-Fucose Anti-DSG3 Mouse-Human Chimeric Antibodies

The method of modifying the sugar chain of an antibody is a known method for enhancing the ADCC activity of an antibody. For example, improvement of ADCC activity by modified antibody glycosylation is described in WO 99/54342. Furthermore, WO 00/61739 describes the adjustment of ADCC activity by the presence or absence of fucose on an antibody sugar chain. WO 02/31140 describes the use of a YB2/0 cell line to prepare an antibody comprising a sugar chain that does not have α-1,6-core fucose. Whether the ADCC improvement techniques described above enhance the activity of the anti-DSG3 antibodies was examined. First, as host cells, the YB2/0 cell line (purchased from ATCC) was cultured in RPMI1640 medium containing 10% FBS. An anti-DSG3 mouse-human chimeric antibody expression vector prepared in Example 7 was introduced into the YB2/0 cell line by the electroporation method under conditions of 1.4 kV and 25 μF. By Geneticin selection (500 μg/mL), YB2/0 cell lines that show constant expression of low-fucose DF151 mouse-human chimeric antibody (hereinafter referred to as YB-DF151c), low-fucose DF364 mouse-human chimeric antibody (hereinafter referred to as YB-DF364c), and low-fucose DF366 mouse-human chimeric antibody (hereinafter referred to as YB-DF366c) were established. Next, the low-fucose anti-DSG3 mouse-human chimeric antibodies were purified from the culture supernatant using a Hi Trap rProtein A column. Purified antibodies were subjected to buffer exchange with PBS buffer using a PD-10 column, quantified by DC Protein Assay, and then stored at 4° C. The purified low-fucose anti-DSG3 mouse-human chimeric antibodies were subjected to flow cytometric analysis to confirm that they bind specifically to DSG3 in the same way as the anti-DSG3 mouse-human chimeric antibodies.

[Example 9] Measurement of CDC Activity and ADCC Activity of Anti-DSG3 Mouse-Human Chimeric Antibodies and Low-Fucose Anti-DSG3 Mouse-Human Chimeric Antibodies 9-1) Establishment of Cell Lines that Show Constant Expression of Full-Length Human DSG3

The full-length human DSG3 cDNA was cloned into a vector (pMCDN) for expression in mammalian cells (pMCDN/hDSG3). The pMCDN vector, into which a neomycin resistance gene and a DHFR gene are incorporated, enables induced expression under the control of a mouse CMV promoter (ACCESSION No. U68299). A Ba/F3 cell line (DSG3-Ba/F3) that shows constant expression of full-length human DSG3 was established by introducing pMCDN/hDSG3 into Ba/F3 cells (purchased from RIKEN BioResource Center) by electroporation, and subjecting them to selection with 500 μg/mL of Geneticin (Invitrogen). DSG3-Ba/F3 cells were cultured using RPMI1640 medium (Invitrogen) containing 500 μg/mL Geneticin, penicillin/streptomycin (Invitrogen), recombinant mouse interleukin-3 (R&D Systems), and 10% fetal bovine serum (Invitrogen).

9-2) Establishment of Cells Showing Constant Expression of Full-Length Human CD16

Full-length human CD16 (RefSeq ID, NM 000569) was cloned into pMCDN, then introduced into NK-92 cells (purchased from ATCC) by electroporation and then subjected to Geneticin selection (500 µg/mL) to establish a NK-92 cell line (CD16-NK92) that shows constant expression of full-length human CD16. The CD16-NK92 cell line was cultured using Minimum Essential Medium Alpha Medium with L-glutamine, without ribonucleosides, deoxyribonucleosides (Invitrogen) containing 500 µg/mL Geneticin, penicillin/streptomycin, 0.2 mM inositol (Sigma), 0.1 mM 2-mercaptoethanol (Invitrogen), 0.02 mM folic acid (Sigma), 100 U/mL recombinant human interleukin-2 (Peprotech), 12.5% horse serum (Invitrogen), and 12.5% fetal bovine serum.

9-3) Measurement of CDC Activity of Anti-DSG3 Mouse-Human Chimeric Antibodies

Figure 8:
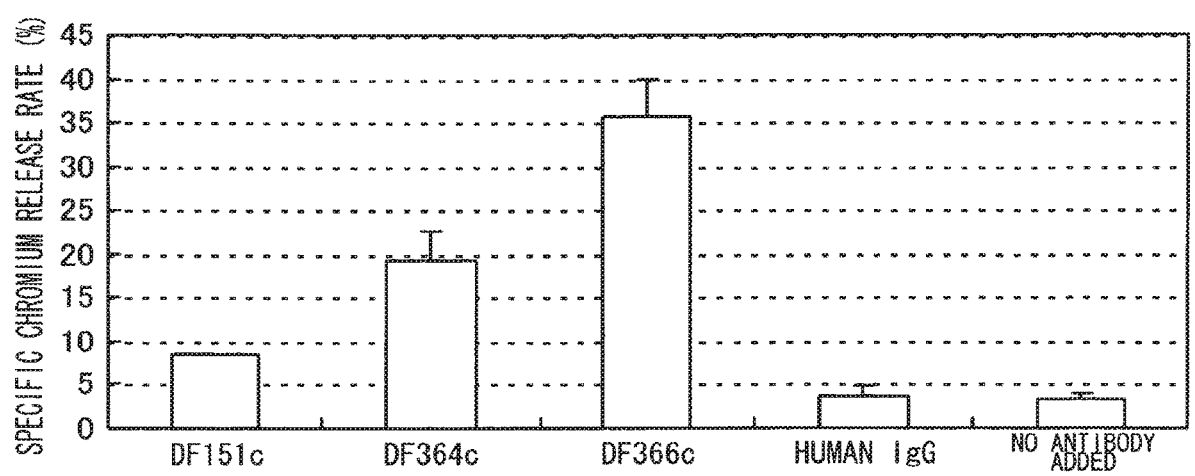
FIG. 8 depicts the CDC activity of anti-DSG3 mouse-human chimeric antibodies DF151c, DF364c, and DF366c towards the DSG3-Ba/F3 cell line, which is a Ba/F3 cell line that constitutively expresses DSG3.

A suspension of 5×10⁵ DSG3-Ba/F3 cells was centrifuged (1000 rpm for five minutes at 4° C.), the resulting cell pellet was suspended in approximately 200 µL of RPMI1640 medium containing 10% fetal bovine serum and penicillin/streptomycin (hereinafter referred to as medium), which was added with 3.7 MBq of Chromium-51 (GE Healthcare Bio-Sciences), and the cells were cultured in a 5% carbon dioxide incubator for one hour at 37° C. These cells were washed three times in the medium, then adjusted to 2×10⁵ cells/mL, and then added to a 96-well round-bottomed plate at 50 µL/well. Next, DF151c, DF364c, DF366c, and a control human IgG antibody (Zymed) were individually added at 50 µL/well. Final concentration of the antibodies was adjusted to 10 µg/mL. Next, baby rabbit complement (Cedarlane) diluted 5-fold in the medium was added at 100 µL each. The plate was left to stand in a 5% carbon dioxide incubator at 37° C. for four hours. After the culturing, the plate was centrifuged (1000 rpm for five minutes at 4° C.), and 100 µL of the supernatant was used for the radioactivity measurement on a gamma counter (1480 WIZARD 3", Wallac). The specific chromium release rate was determined according to the following equation:

Specific chromium release rate (%)=(A−C)×100/(B−C)

where A represents the radioactivity (cpm) in each well, B represents the mean value of radioactivity (cpm) in wells where 50 µL of the cells and 150 µL of 2% Nonidet P-40 solution (Nacalai Tesque) have been added, and C represents the mean value of radioactivity (cpm) in wells where 50 µL of the cells and 150 µL of the medium have been added. The assay was conducted in duplicate, and the mean value and standard deviation were calculated for the specific chromium release rate. DF151c, DF364c, and DF366c were shown to have CDC activity (FIG. 8).

9-4) Measurement of ADCC Activity of Anti-DSG3 Mouse-Human Chimeric Antibodies and Low-Fucose Anti-DSG3 Mouse-Human Chimeric Antibodies DSG3-Ba/F3 cells were labeled with Chromium-51, and then added to a 96-well round-bottomed plate at 50 µL/well. Next, DF364c, DF366c, YB-DF364c, YB-DF366c, and a control human IgG antibody were individually added at 50 µL/well. Final concentrations of the antibodies were adjusted by four 10-fold serial dilutions starting from 1 µg/mL. Subsequently, CD16-NK92 cells at 2×10⁵ cells/mL were added at 100 µL/well. The plate was left to stand in a 5% carbon dioxide incubator at 37° C. for four hours, and then the specific chromium release rate was determined using the same method as that of 9-3).

Figure 9:
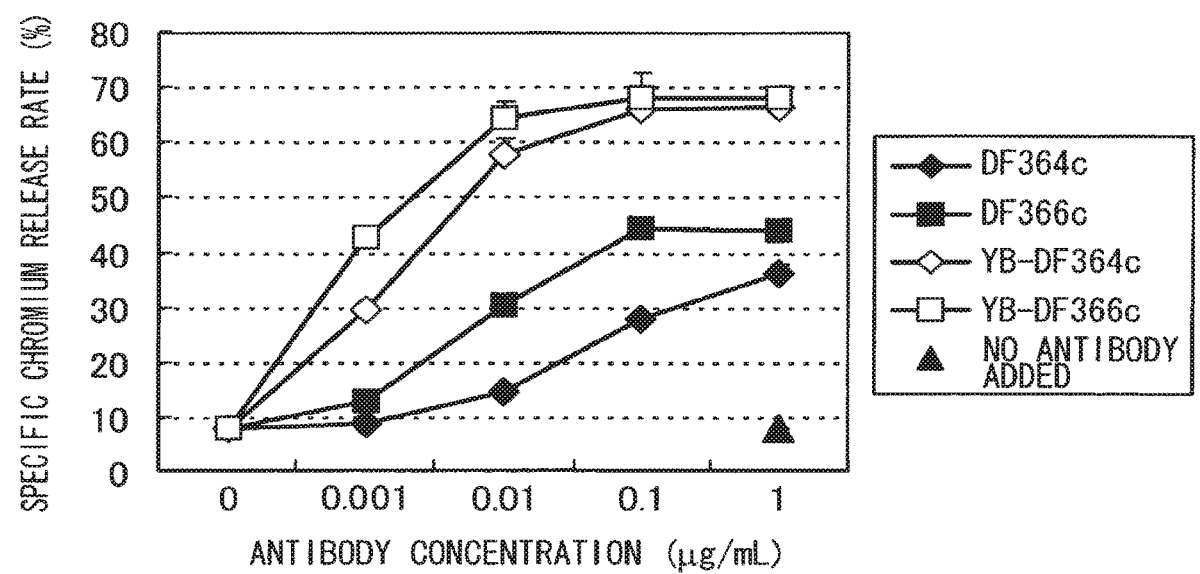
FIG. 9 depicts the ADCC activity of anti-DSG3 mouse-human chimeric antibodies DF364c and DF366c, and low-fucose anti-DSG3 mouse-human chimeric antibodies YB-DF364c and YB-DF366c, towards the DSG3-Ba/F3 cell line, which is a Ba/F3 cell line that constitutively expresses DSG3.

All antibodies showed ADCC activity in an antibody concentration-dependent manner (FIG. 9). In particular, low-fucose antibodies YB-DF364c and YB-DF366c showed strong ADCC activity.

[Example 10] Immunohistological Staining of DSG3 in Lung Cancer, Skin Cancer, and Uterine Cancer The DSG3 expression was enhanced at the protein level in lung squamous cell carcinoma (see Example 2). Therefore, immunohistological staining analyses were newly performed to confirm the DSG3 protein expression in skin cancer, uterine cancer, and lung adenocarcinoma which is a lung cancer that affects a large number of people. First, 4% paraformaldehyde (PFA) or periodate-lysine-paraformaldehyde (PLP)-fixed AMeX embedded paraffin block and 10% neutral buffer formaldehyde (NBF)-fixed paraffin-embedded block were prepared from each sample, and 3-µm-thin sections were prepared. After deparaffinization, these sections were stained immunohistochemically as described below using the Ventana HX Discovery System (Ventana Medical Systems, Inc., Arizona, USA). Each preparation was washed with water after deparaffinization, and reacted with 3.0% hydrogen peroxide solution (Inhibitor D) for four minutes at room temperature to eliminate endogenous peroxidase. This was washed, and with addition of protein blocker to eliminate non-specific reactions, this was reacted for 30 minutes at room temperature. After washing, a mouse anti-human Desmoglein 3 antibody (Clone 5G11, ZYMED Laboratories Inc., California, USA) was added as a primary antibody, and then reacted for one hour at room temperature. After washing, a secondary antibody (Ventana Universal Secondary Antibody, Ventana Medical Systems) was added and reacted for 30 minutes at room temperature. After washing, reaction with Blocker D was carried out for two minutes at room temperature to remove non-specific reactions, and then streptavidin horseradish peroxidase (SA-HRP, Ventana Medical Systems) was added and reacted at 37° C. for 16 minutes. After washing, a mixture of diaminobenzidine (DAB map solution, Ventana Medical Systems) and hydrogen peroxide solution (DAB map solution, Ventana Medical Systems) was added and reacted for eight minutes at 37° C. for substrate color development. Next, the color was intensified using a copper sulfate solution (Ventana Medical Systems). After washing, this was subjected to nuclear staining with hematoxylin, dehydration, penetration, and inclusion.

As a result, the DSG3 expression was confirmed in two out of three cases in lung squamous cell carcinoma, one out of nine cases in lung adenocarcinoma, two out of two cases in skin squamous cell carcinoma, one out of one case in skin basal cell carcinoma, and one out of one case in uterine squamous cell carcinoma (Table 3).

TABLE 3

| | Lung[a] | | | | | | | | | | | Skin | | Uterus |
|---|---|---|---|---|---|---|---|---|---|---|---|---|---|---|
| SCC[b] | | Adenocarcinoma | | | | | | | | | | SCC | BCC | SCC |
| 2[c] | 3 | 3-M | 1 | 2 | 2 | 2-M | 3 | 3 | 3 | 3-M | 3-M | 1 | 3 | — | 2 |
| 1[d] | 2 | 3 | 4 | 5 | 6 | 7 | 8 | 9 | 10 | 11 | 12 | 14 | 15 | 16 | 17 |
| Desmoglein-3 | | | | | | | | | | | | | | | |
| Intensity 3-4[e] | 2-4 | 0 | 0 | 0 | 0 | 0 | 2-4 | 0 | 0 | 0 | 0 | 2-4 | 1-4 | 1-4 | 2-4 |
| Frequency 4[f] | 4 | — | — | — | — | — | 2 | — | — | — | — | 4 | 3 | 3 | 4 |

Abbreviations:
BCC, basal cell carcinoma;
M, metastatic cancer;
SCC, squamous cell carcinoma
[a] tissue site of cancer
[b] tissue type
[c] grade of cancer (1, well-differentiated; 2, moderately-differentiated; 3, poorly-differentiated)
[d] case number
[e] 1, faint; 2, weak; 3, moderate; 4, strong
[f] 1, rare (less than 10%); 2, occasional (10% and above, less than 50%); 3, frequent (50% and above, less than 90%); 4, constant (90% and above)

[Example 11] Evaluation of Antitumor Activity of Anti-DSG3 Antibodies

11-1) Production of Mouse IgG2a Chimeric DF366 Antibody (DF366m)

The nucleotide sequence of the H-chain variable region gene of DF366 antibody was ligated in frame to the nucleotide sequence of H-chain constant region gene of mouse IgG2a. First, PCR was performed using a primer (SEQ ID NO: 105) having the 5' end nucleotide sequence of the H-chain variable region gene, a Kozak sequence, and an EcoRI restriction enzyme sequence, and an antisense primer (SEQ ID NO: 106) having a c residue attached to a sequence complementary to the 3'-end nucleotide sequence. The obtained amplified product was treated with the EcoRI restriction enzyme, and then incorporated into the EcoRI-NruI site of a mouse IgG2a chimeric H-chain expression plasmid (pMCD/G2a) to construct a mouse IgG2a chimeric DF366 antibody H-chain expression vector (pMCD/G2a-DF366). pMCD/G2a has the H-chain constant region gene of mouse IgG2a (nucleotide sequence: SEQ ID NO: 107; amino acid sequence: SEQ ID NO: 108) cloned into a pMCD plasmid for expression in mammalian cells, and the NruI restriction enzyme sequence of the H-chain constant region is ligated to the H-chain variable region. The pMCD vector, into which a DHFR gene has been incorporated, enables induced expression under the control of a mouse CMV promoter (ACCESSION No. U68299).

The nucleotide sequence of the L-chain variable region gene of DF366 antibody was ligated in frame to the nucleotide sequence of the L-chain (κ chain) constant region gene of mouse IgG2a. First, PCR was performed using a primer (SEQ ID NO: 109) having the 5'-end nucleotide sequence of the L-chain variable region gene, a Kozak sequence, and the EcoRI restriction enzyme sequence, and an antisense primer (SEQ ID NO: 110) having gcccg residues attached to a sequence complementary to the 3'-end nucleotide sequence. The amplified product obtained was treated with EcoRI restriction enzyme, and then incorporated into the EcoRI-NruI site of a mouse IgG2a chimeric L-chain (κ chain) expression plasmid (pMCN/k) to construct a mouse IgG2a chimeric DF366 antibody L-chain expression vector (pMCN/k-DF366). pMCN/k has the L-chain (κ chain) constant region gene of mouse IgG2a (nucleotide sequence: SEQ ID NO: 111; amino acid sequence: SEQ ID NO: 112) cloned into the plasmid pMCN, and the NruI restriction enzyme sequence of the L-chain (κ chain) constant region is ligated to the L-chain variable region.

The plasmid pMCD/G2a-DF366 and the plasmid pMCN/k-DF366 were introduced into DG44 cells by electroporation. CHO cells (DF366m-DG44) showing constant expression of the mouse IgG2a chimeric DF366 antibody (DF366m) were established by Geneticin selection (500 μg/mL) and nucleic acid (HT supplement)-free medium. Subsequently, the DF366m antibody was purified from the culture supernatant of DF366m-DG44 using a Hi Trap Protein G HP column. The solvent was substituted with PBS using a PD-10 column. The concentration of the purified DF366m antibody was quantified using a DC Protein Assay kit. The DF366m antibody was subjected to flow cytometric analysis to confirm that it specifically binds to DSG3 in the same way as the DF366 antibody (described in Example 3-5). The nucleotide sequence of the full-length DF366m antibody H-chain gene and the corresponding amino acid sequence are shown in SEQ ID NO: 113 and SEQ ID NO: 114, respectively, and the nucleotide sequence of the full-length DF366m antibody L-chain gene and the corresponding amino acid sequence are shown in SEQ ID NO: 115 and SEQ ID NO: 116, respectively.

11-2) Production of Low-Fucose Mouse IgG2a Chimeric DF366 Antibody (Low Fucose DF366m)

The plasmid pMCD/G2a-DF366 and the plasmid pMCN/k-DF366 were introduced into fucose transporter knockout CHO cells (FTPKO-DXB11 cells, International Patent Publication Nos. WO 2006/067913 and WO 2006/067847) by electroporation. CHO cells (DF366m-DXB11) showing constant expression of the low-fucose mouse IgG2a chimeric DF366 antibody (low fucose DF366m) were established by Geneticin selection (500 μg/mL) and nucleic acid (HT supplement)-free medium. Subsequently, the low-fucose DF366m antibody was purified from the culture supernatant of DF366m-DXB11 using a Hi Trap Protein G HP column. The solvent was substituted with PBS using a PD-10 column, and the antibody concentration was quantified using a DC Protein Assay kit.

11-3) Measurement of ADCC Activity

RPMI1640 medium (Invitrogen) containing penicillin/streptomycin and 10% fetal bovine serum (hereinafter referred to as RPMI medium) was used for the experiment. $1\times10^6$ DSG3-Ba/F3 cells were suspended in approximately 200 μL of RPMI medium containing 3.7 MBq of Chromium-51 (GE Healthcare Bio-Sciences), and then cultured in a 5% carbon dioxide incubator for one hour at 37° C. After washing, the cell density was adjusted to $2\times10^5$ cells/mL, and then dispensed into a 96-well U-bottom plate at 50 μL/well. Next, the antibody solution was added at 50 μL/well. After incubating at room temperature for 15 minutes, effector cells (described later) were added at 100 μL each. The plate was left to stand in a 5% carbon dioxide incubator at 37° C. for six hours. Thereafter, 100 μL of the supernatant was collected from each well, and the radioactivity was measured with a gamma counter (1480 WIZARD 3", Wallac). The specific chromium release rate was calculated according to the following equation:

Specific chromium release rate (%)=$(A-C)\times100/(B-C)$ where A represents the radioactivity (cpm) in each well, B represents the mean value of radioactivity (cpm) in wells where 50 μL of the cells and 150 μL of 2% Nonidet P-40 solution (Nacalai Tesque) have been added, and C represents the mean value of radioactivity (cpm) in wells where 50 μL of the cells and 150 μL of RPMI medium have been added. The measurements were conducted in duplicate, and the mean value and standard deviation were calculated for the specific chromium release rate.

Cells obtained by adding 50 ng/mL recombinant human interleukin-2 (Peprotech) to spleen cells prepared from a C3H mouse (Charles River Japan) (hereinafter referred to as SPL) or cells obtained by culturing spleen cells for four days in the presence of 50 ng/mL of recombinant human interleukin-2 (hereinafter referred to as SPL-LAK) were used as effector cells. The number of effector cells per well was set to $5\times10^5$ cells (SPL) or $2\times10^5$ cells (SPL-LAK). Mouse IgG2a (Cat. No. 553453, Becton Dickinson) and human IgG1 (Cat. No. PHP010, Serotec) were used as negative controls.

Figure 10:
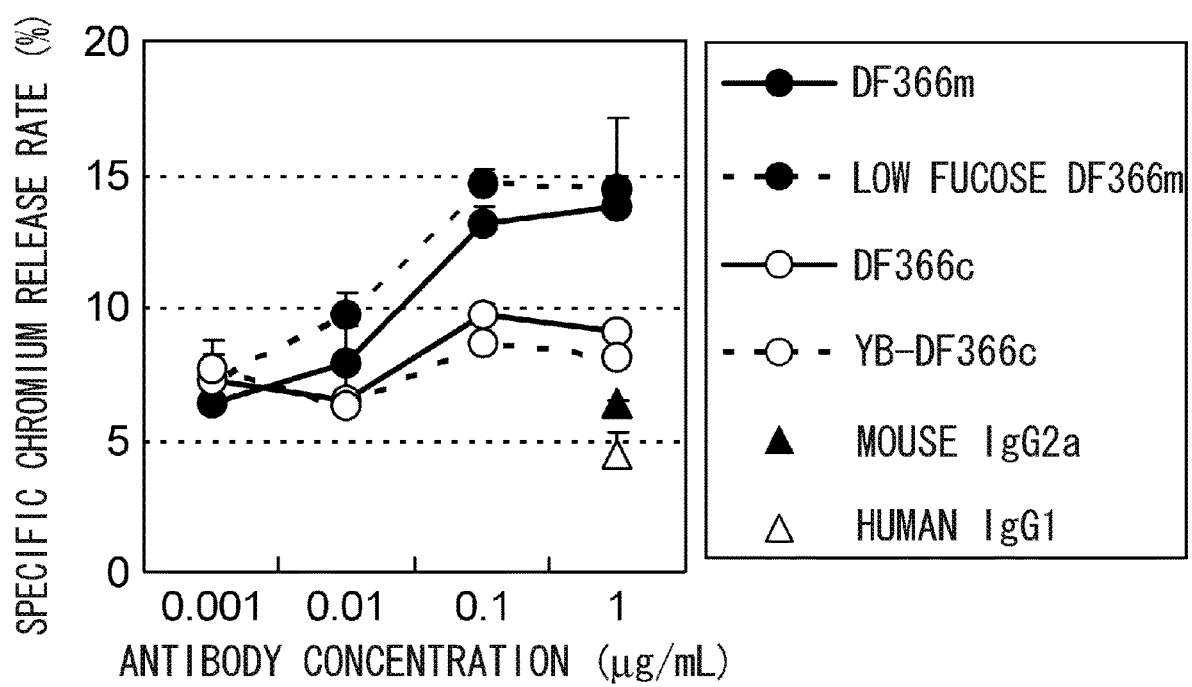
FIG. 10 depicts the ADCC activity of anti-DSG3 antibodies DF366m (mouse IgG2a chimeric antibody), low-fucose DF366m (low-fucose mouse IgG2a chimeric antibody), DF366c (mouse-human chimeric antibody) and YB-DF366c (low-fucose mouse-human chimeric antibody) towards the DSG3-Ba/F3 cell line, which is a Ba/F3 cell line that constitutively expresses DSG3. Mouse spleen cells that have added interleukin-2 were used as effector cells.
Figure 11:
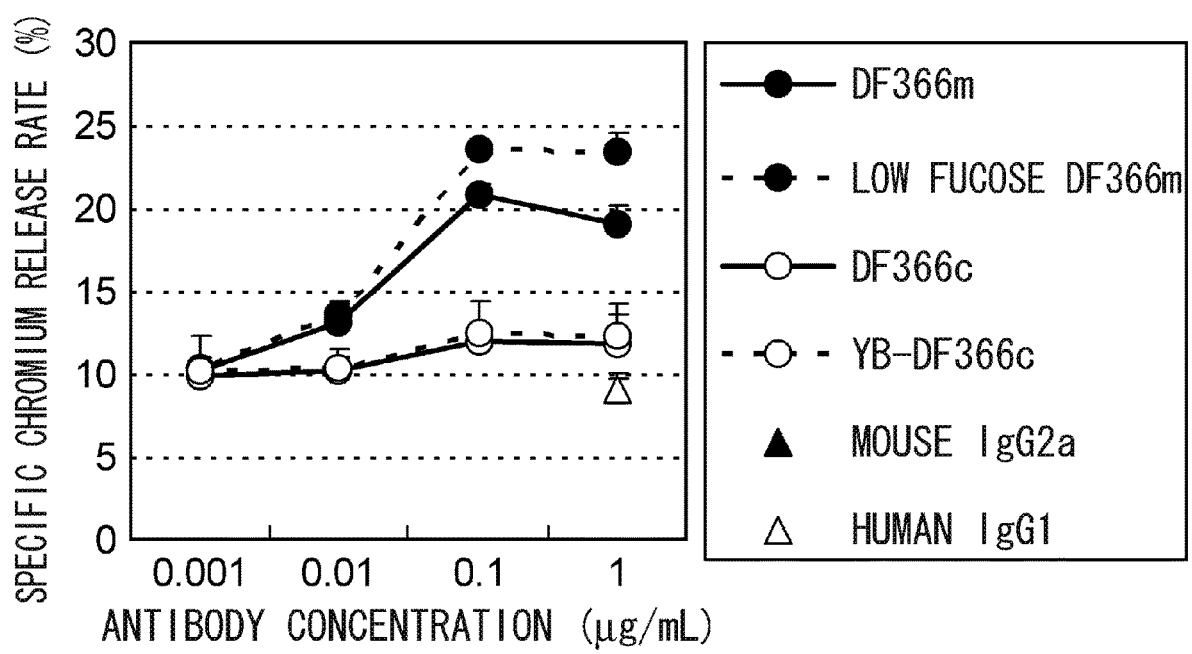
FIG. 11 depicts the ADCC activity of anti-DSG3 antibodies DF366m (mouse IgG2a chimeric antibody), low-fucose DF366m (low-fucose mouse IgG2a chimeric antibody), DF366c (mouse-human chimeric antibody) and YB-DF366c (low-fucose mouse-human chimeric antibody) towards the DSG3-Ba/F3 cell line, which is a Ba/F3 cell line that constitutively expresses DSG3. Mouse spleen cells cultured for four days in the presence of interlekin-2 were used as effector cells.

ADCC activity was detected in DF366m and low-fucose DF366m, but ADCC activity was hardly observed in DF366c and YB-DF366c (FIGS. 10 and 11). Therefore, DF366m and low-fucose DF366m were considered to show stronger medicinal effect than DF366c and YB-DF366c in mice.

11-4) Establishment of Cell Line Showing Constant Expression of Full-Length Human DSG3

After digesting pMCDN/hDSG3 with the PvuI restriction enzyme, this was introduced into SK-HEP-1 cells (purchased from ATCC) by transfection using FuGENE (Roche), and a SK-HEP-1 cell line (hereinafter referred to as DSG3-SK) showing constant expression of full-length human DSG3 was established by Geneticin selection (1 mg/mL). D-MEM medium (Sigma) containing 1 mg/mL Geneticin and 10% fetal bovine serum was used to culture the DSG3-SK cells.

11-5) Evaluation of Antitumor Activity of DF366m and Low-Fucose DF366m

DSG3-SK cells were adjusted to $1\times10^8$ cells/mL in a solution containing a 1:1 ratio of D-MEM medium and MATRIGEL (Cat. No. 354234, BD Bioscience), and 100 μL of this cell solution was subcutaneously transplanted to the abdomen of a SCID mouse (female, 9-weeks old, CLEA Japan) that had been subjected to intraperitoneal administration of 100 μL of anti-asialo GM1 antibody (Wako Pure Chemicals, after dissolving one vial using 1 mL of distilled water for injection, 4 mL of physiological saline solution was added) on the previous day. From the 19th day after transplantation, DF366m and low-fucose DF366m were administered through the tail vein once a week for four weeks. The antibodies were prepared in PBS at 1 mg/mL (10 mg/kg administration group) or 0.2 mg/mL (2 mg/kg administration group), and administered at 10 mL/kg. PBS (vehicle) was administered similarly as a negative control. The assay was carried out using five animals in each group. Antitumor activity was evaluated based on tumor volume. The tumor volume was determined based on the following equation, and the mean value and standard deviation were calculated:

Tumor volume=major axis×minor axis×minor axis/2

Non-parametric Dunnett's multiple comparison was used for the significant difference test, and P value less than 0.05 was considered significant.

Figure 12:
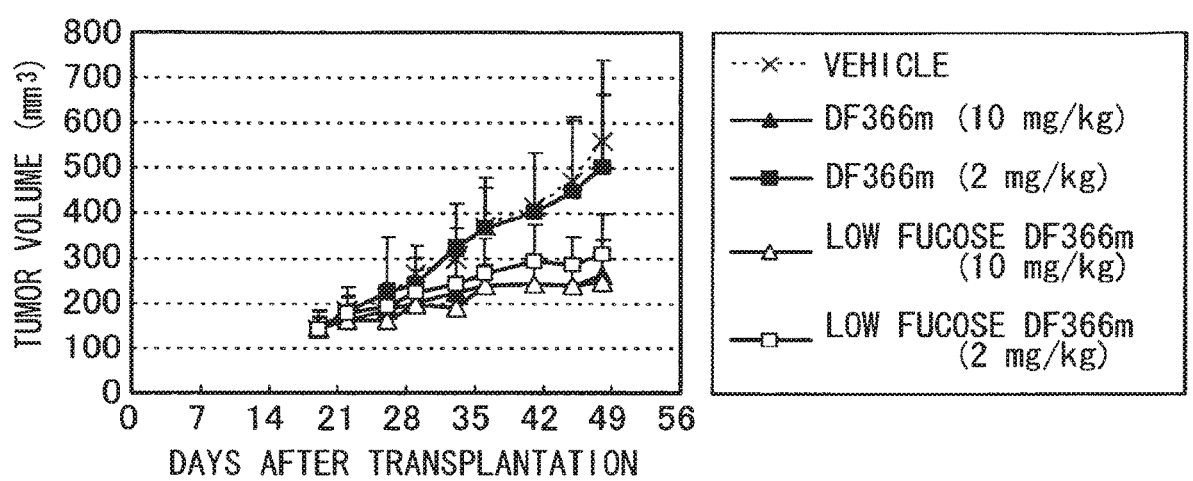
FIG. 12 depicts the antitumor activity of anti-DSG3 antibodies DF366m (mouse IgG2a chimeric antibody) and low-fucose DF366m (low-fucose mouse IgG2a chimeric antibody).

As a result of the examination, DF366m and low-fucose DF366m significantly suppressed tumor growth in the 10 mg/kg administration group as compared to the vehicle administration group (FIG. 12). Furthermore, although not significant, low-fucose DF366m indicated a suppressive tendency also at 2 mg/kg. From the above, anti-DSG3 antibodies were confirmed to show antitumor activity.

INDUSTRIAL APPLICABILITY

The DSG3 protein-specific antibodies of the present invention can be used as a diagnostic agent not only for lung cancer but also for colon cancer, esophageal cancer, stomach cancer, pancreatic cancer, skin cancer, and uterine cancer. Furthermore, by using the anti-DSG3 antibodies after labeling them with a chemical substance or a radioisotope, the presence of lung cancer, colon cancer, esophageal cancer, stomach cancer, pancreatic cancer, skin cancer, or uterine cancer can be detected in vivo.

Furthermore, anti-DSG3 antibodies having cytotoxic activity according to the present invention can be used as cytotoxic agents or cell growth inhibitors for various types of cancer cells that express a DSG3 protein, such as cells of lung cancer, colon cancer, esophageal cancer, stomach cancer, pancreatic cancer, skin cancer, or uterine cancer.

Furthermore, anti-DSG3 antibodies having cytotoxic activity according to the present invention can be used as therapeutic agents against various types of cancers such as lung cancer, colon cancer, esophageal cancer, stomach cancer, pancreatic cancer, skin cancer, or uterine cancer. In addition, anti-DSG3 antibodies of the present invention can be used as therapeutic agents for these cancers without inducing pemphigus conditions.

Additionally, genes encoding antibodies of the present invention and recombinant cells transformed by these genes can be used to produce recombinant antibodies that exhibit the above-mentioned effects and more preferred effects.

The invention claimed is:

1. A humanized monoclonal antibody that specifically binds to a Desmoglein-3 (DSG3) protein, wherein the antibody comprises an Heavy (H) chain having the amino acid sequence of SEQ ID NO: 81 as complementarity determining region (CDR)1, the amino acid sequence of SEQ ID NO: 83 as CDR2, and the amino acid sequence of SEQ ID NO: 85 as CDR3, and an Light (L) chain having the amino acid sequence of SEQ ID NO: 87 as CDR1, the amino acid sequence of SEQ ID NO: 89 as CDR2, and the amino acid sequence of SEQ ID NO: 91 as CDR3.

2. The humanized monoclonal antibody of claim 1, wherein the antibody comprises an H chain having the amino acid sequence of SEQ ID NO: 28 and an L chain having the amino acid sequence of SEQ ID NO: 36.

3. The humanized monoclonal antibody of claim 1, which has antibody-dependent cellular cytotoxicity (ADCC) or Complement-dependent cytotoxicity (CDC) activity.

4. The humanized monoclonal antibody of claim 1, which is an isolated monoclonal antibody.

5. The humanized monoclonal antibody of claim 2, which has ADCC or CDC activity.

6. The humanized monoclonal antibody of claim 2, which is an isolated monoclonal antibody.

7. The humanized monoclonal antibody of claim 1, wherein the antibody comprises an H chain having the amino acid sequence of SEQ ID NO: 10 and an L chain having the amino acid sequence of SEQ ID NO: 20.

8. The humanized monoclonal antibody of claim 7, which has ADCC or CDC activity.

9. The humanized monoclonal antibody of claim 7, which is an isolated monoclonal antibody.

* * * * *

UNITED STATES PATENT AND TRADEMARK OFFICE
CERTIFICATE OF CORRECTION

PATENT NO. : 10,696,743 B2
APPLICATION NO. : 15/430031
DATED : June 30, 2020
INVENTOR(S) : Aburatani et al.

It is certified that error appears in the above-identified patent and that said Letters Patent is hereby corrected as shown below:

On the Title Page

Item (73), please amend the Assignee from, "Chugai Seiyaku Kabushiki Kaisha, Tokyo (JP)" to
-- Chugai Seiyaku Kabushiki Kaisha, Tokyo (JP); The University of Tokyo, Tokyo (JP) --.

Signed and Sealed this
Fourteenth Day of February, 2023

Katherine Kelly Vidal
*Director of the United States Patent and Trademark Office*

SEQUENCE LISTING

<160> NUMBER OF SEQ ID NOS: 116

<210> SEQ ID NO 1

```
<211> LENGTH: 15
<212> TYPE: DNA
<213> ORGANISM: Mus musculus

<400> SEQUENCE: 1
gcctactaca tgcac                                                       15

<210> SEQ ID NO 2
<211> LENGTH: 5
<212> TYPE: PRT
<213> ORGANISM: Mus musculus

<400> SEQUENCE: 2

Ala Tyr Tyr Met His
1               5

<210> SEQ ID NO 3
<211> LENGTH: 51
<212> TYPE: DNA
<213> ORGANISM: Mus musculus

<400> SEQUENCE: 3
cagattaatc ctagcactgg tggtactacc tacaaccaga agttcaaggc c                51

<210> SEQ ID NO 4
<211> LENGTH: 17
<212> TYPE: PRT
<213> ORGANISM: Mus musculus

<400> SEQUENCE: 4

Gln Ile Asn Pro Ser Thr Gly Gly Thr Thr Tyr Asn Gln Lys Phe Lys
1               5                   10                  15
Ala

<210> SEQ ID NO 5
<211> LENGTH: 12
<212> TYPE: DNA
<213> ORGANISM: Mus musculus

<400> SEQUENCE: 5
tggggtgact ct                                                          12

<210> SEQ ID NO 6
<211> LENGTH: 4
<212> TYPE: PRT
<213> ORGANISM: Mus musculus

<400> SEQUENCE: 6

Trp Gly Asp Ser
1

<210> SEQ ID NO 7
<211> LENGTH: 1011
<212> TYPE: DNA
<213> ORGANISM: Mus musculus

<400> SEQUENCE: 7
gccaaaacaa cacccccatc agtctatcca ctggcccctg ggtgtggaga taacaactggt     60 tcctctgtga ctctgggatg cctggtcaag ggctacttcc ctgagtcagt gactgtgact    120
tggaactctg gatccctgtc cagcagtgtg cacaccttcc cagctctcct gcagtctgga    180
ctctacacta tgagcagctc agtgactgtc ccctccagca cctggccaag tcagaccgtc    240
```

```
acctgcagcg ttgctcaccc agccagcagc accacggtgg acaaaaaact tgagcccagc    300
gggcccattt caacaatcaa ccctgtcct ccatgcaagg agtgtcacaa atgcccagct    360
cctaacctcg agggtggacc atccgtcttc atcttccctc caaatatcaa ggatgtactc    420
atgatctccc tgacacccaa ggtcacgtgt gtggtggtgg atgtgagcga ggatgaccca    480
gacgtccaga tcagctggtt tgtgaacaac gtggaagtac acacagctca gacacaaacc    540
catagagagg attacaacag tactatccgg gtggtcagtg ccctccccat ccagcaccag    600
gactggatga gtggcaagga gttcaaatgc aaggtcaaca caaagacct cccatcaccc    660
atcgagagaa ccatctcaaa aattaaaggg ctagtcagag ctccacaagt atacatcttg    720
ccgccaccag cagagcagtt gtccaggaaa gatgtcagtc tcacttgcct ggtcgtgggc    780
ttcaaccctg agacatcag tgtggagtgg accagcaatg gcatacaga ggagaactac    840
aaggacaccg caccagtcct ggactctgac ggttcttact tcatatacag caagctcgat    900
ataaaaacaa gcaagtggga gaaacagat tccttctcat gcaacgtgag acacgagggt    960
ctgaaaaatt actacctgaa gaagaccatc tcccggtctc cgggtaaatg a          1011
```

<210> SEQ ID NO 8
<211> LENGTH: 336
<212> TYPE: PRT
<213> ORGANISM: Mus musculus

<400> SEQUENCE: 8

```
Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
            20                  25                  30

Phe Pro Glu Ser Val Thr Val Thr Trp Asn Ser Gly Ser Leu Ser Ser
        35                  40                  45

Ser Val His Thr Phe Pro Ala Leu Leu Gln Ser Gly Leu Tyr Thr Met
    50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95

Leu Glu Pro Ser Gly Pro Ile Ser Thr Ile Asn Pro Cys Pro Pro Cys
            100                 105                 110

Lys Glu Cys His Lys Cys Pro Ala Pro Asn Leu Glu Gly Gly Pro Ser
        115                 120                 125

Val Phe Ile Phe Pro Pro Asn Ile Lys Asp Val Leu Met Ile Ser Leu
    130                 135                 140

Thr Pro Lys Val Thr Cys Val Val Val Asp Val Ser Glu Asp Asp Pro
145                 150                 155                 160

Asp Val Gln Ile Ser Trp Phe Val Asn Asn Val Glu Val His Thr Ala
                165                 170                 175

Gln Thr Gln Thr His Arg Glu Asp Tyr Asn Ser Thr Ile Arg Val Val
            180                 185                 190

Ser Ala Leu Pro Ile Gln His Gln Asp Trp Met Ser Gly Lys Glu Phe
        195                 200                 205

Lys Cys Lys Val Asn Asn Lys Asp Leu Pro Ser Pro Ile Glu Arg Thr
    210                 215                 220

Ile Ser Lys Ile Lys Gly Leu Val Arg Ala Pro Gln Val Tyr Ile Leu
225                 230                 235                 240
```

-continued

```
Pro Pro Pro Ala Glu Gln Leu Ser Arg Lys Asp Val Ser Leu Thr Cys
            245                 250                 255

Leu Val Val Gly Phe Asn Pro Gly Asp Ile Ser Val Glu Trp Thr Ser
        260                 265                 270

Asn Gly His Thr Glu Glu Asn Tyr Lys Asp Thr Ala Pro Val Leu Asp
    275                 280                 285

Ser Asp Gly Ser Tyr Phe Ile Tyr Ser Lys Leu Asp Ile Lys Thr Ser
290                 295                 300

Lys Trp Glu Lys Thr Asp Ser Phe Ser Cys Asn Val Arg His Glu Gly
305                 310                 315                 320

Leu Lys Asn Tyr Tyr Leu Lys Lys Thr Ile Ser Arg Ser Pro Gly Lys
                325                 330                 335
```

<210> SEQ ID NO 9
<211> LENGTH: 1004
<212> TYPE: DNA
<213> ORGANISM: Homo sapiens

<400> SEQUENCE: 9

```
gctagcacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagaa agttgagccc   300
aaatcttgtg acaaaactca cacatgccca ccgtgcccag cacctgaact cctggggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggatgag   720
ctgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa tgataagcgg ccgc                   1004
```

<210> SEQ ID NO 10
<211> LENGTH: 330
<212> TYPE: PRT
<213> ORGANISM: Homo sapiens

<400> SEQUENCE: 10

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 11
<211> LENGTH: 45
<212> TYPE: DNA
<213> ORGANISM: Mus musculus

<400> SEQUENCE: 11
agagccagtg aaagtgttga atattatggc actagtttaa tgcag            45

<210> SEQ ID NO 12
<211> LENGTH: 15
<212> TYPE: PRT
<213> ORGANISM: Mus musculus

<400> SEQUENCE: 12

Arg Ala Ser Glu Ser Val Glu Tyr Tyr Gly Thr Ser Leu Met Gln
1               5                   10                  15

<210> SEQ ID NO 13
<211> LENGTH: 21
<212> TYPE: DNA
<213> ORGANISM: Mus musculus
```

<400> SEQUENCE: 13
ggtgcatccg acgtagaatc t                                          21

<210> SEQ ID NO 14
<211> LENGTH: 7
<212> TYPE: PRT
<213> ORGANISM: Mus musculus

<400> SEQUENCE: 14

Gly Ala Ser Asp Val Glu Ser
1               5

<210> SEQ ID NO 15
<211> LENGTH: 27
<212> TYPE: DNA
<213> ORGANISM: Mus musculus

<400> SEQUENCE: 15
cagcaaagta ggaaggttcc gtatacg                                    27

<210> SEQ ID NO 16
<211> LENGTH: 9
<212> TYPE: PRT
<213> ORGANISM: Mus musculus

<400> SEQUENCE: 16

Gln Gln Ser Arg Lys Val Pro Tyr Thr
1               5

<210> SEQ ID NO 17
<211> LENGTH: 324
<212> TYPE: DNA
<213> ORGANISM: Mus musculus

<400> SEQUENCE: 17
cgggctgatg ctgcaccaac tgtatccatc ttcccaccat ccagtgagca gttaacatct    60
ggaggtgcct cagtcgtgtg cttcttgaac aacttctacc ccaaagacat caatgtcaag   120
tggaagattg atggcagtga acgacaaaat ggcgtcctga acagttggac tgatcaggac   180
agcaaagaca gcacctacag catgagcagc accctcacgt tgaccaagga cgagtatgaa   240
cgacataaca gctatacctg tgaggccact cacaagacat caacttcacc cattgtcaag   300
agcttcaaca ggaatgagtg ttag                                        324

<210> SEQ ID NO 18
<211> LENGTH: 107
<212> TYPE: PRT
<213> ORGANISM: Mus musculus

<400> SEQUENCE: 18

Arg Ala Asp Ala Ala Pro Thr Val Ser Ile Phe Pro Pro Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 19
<211> LENGTH: 335
<212> TYPE: DNA
<213> ORGANISM: Homo sapiens

<400> SEQUENCE: 19
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct caatcgggt aactcccagg agagtgtcac agagcaggac      180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttgataagcg gccgc                                335

<210> SEQ ID NO 20
<211> LENGTH: 107
<212> TYPE: PRT
<213> ORGANISM: Homo sapiens

<400> SEQUENCE: 20

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 21
<211> LENGTH: 15
<212> TYPE: DNA
<213> ORGANISM: Mus musculus

<400> SEQUENCE: 21
agctactgga ttcac                                                       15

<210> SEQ ID NO 22
<211> LENGTH: 5
<212> TYPE: PRT
<213> ORGANISM: Mus musculus

<400> SEQUENCE: 22

Ser Tyr Trp Ile His
1               5

<210> SEQ ID NO 23
<211> LENGTH: 51

<212> TYPE: DNA
<213> ORGANISM: Mus musculus

<400> SEQUENCE: 23
tctatttatc ctggaaatag tgatactacc tacaaccaga agttcaaggg c         51

<210> SEQ ID NO 24
<211> LENGTH: 17
<212> TYPE: PRT
<213> ORGANISM: Mus musculus

<400> SEQUENCE: 24

Ser Ile Tyr Pro Gly Asn Ser Asp Thr Thr Tyr Asn Gln Lys Phe Lys
1               5                   10                  15

Gly

<210> SEQ ID NO 25
<211> LENGTH: 42
<212> TYPE: DNA
<213> ORGANISM: Mus musculus

<400> SEQUENCE: 25
cctacttact atagttacga cgattactat gctatggact at                   42

<210> SEQ ID NO 26
<211> LENGTH: 14
<212> TYPE: PRT
<213> ORGANISM: Mus musculus

<400> SEQUENCE: 26

Pro Thr Tyr Tyr Ser Tyr Asp Asp Tyr Tyr Ala Met Asp Tyr
1               5                   10

<210> SEQ ID NO 27
<211> LENGTH: 975
<212> TYPE: DNA
<213> ORGANISM: Mus musculus

<400> SEQUENCE: 27
gccaaaacga cacccccatc tgtctatcca ctggcccctg gatctgctgc ccaaactaac    60
tccatggtga ccctgggatg cctggtcaag ggctatttcc ctgagccagt gacagtgacc   120
tggaactctg gatccctgtc cagcggtgtg cacaccttcc cagctgtcct gcagtctgac   180
ctctacactc tgagcagctc agtgactgtc ccctccagca cctggcccag ccagaccgtc   240
acctgcaacg ttgcccaccc ggccagcagc accaaggtgg acaagaaaat tgtgcccagg   300
gattgtggtt gtaagccttg catatgtaca gtcccagaag tatcatctgt cttcatcttc   360
cccccaaagc ccaaggatgt gctcaccatt actctgactc ctaaggtcac gtgtgttgtg   420
gtagacatca gcaaggatga tcccgaggtc cagttcagct ggtttgtaga tgatgtggag   480
gtgcacacag ctcagacaaa accccgggag gagcagttca acagcacttt ccgttcagtc   540
agtgaacttc ccatcatgca ccaggactgg ctcaatggca aggagttcaa atgcagggtc   600
aacagtgcag ctttccctgc ccccatcgag aaaaccatct ccaaaaccaa aggcagaccg   660
aaggctccac aggtgtacac cattccacct cccaaggagc agatggccaa ggataaagtc   720
agtctgacct gcatgataac agacttcttc cctgaagaca ttactgtgga gtggcagtgg   780
aatgggcagc cagcggagaa ctacaagaac actcagccca tcatggacac agatggctct   840
tacttcgtct acagcaagct caatgtgcag aagagcaact gggaggcagg aaatactttc   900

```
acctgctctg tgttacatga gggcctgcac aaccaccata ctgagaagag cctctcccac    960
tctcctggta aatga                                                    975
```

<210> SEQ ID NO 28
<211> LENGTH: 324
<212> TYPE: PRT
<213> ORGANISM: Mus musculus

<400> SEQUENCE: 28

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Lys Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 29
<211> LENGTH: 36
<212> TYPE: DNA
<213> ORGANISM: Mus musculus

```
<400> SEQUENCE: 29
agtgtcagct caagtataag ttccagcaac ttacac                                36

<210> SEQ ID NO 30
<211> LENGTH: 12
<212> TYPE: PRT
<213> ORGANISM: Mus musculus

<400> SEQUENCE: 30

Ser Val Ser Ser Ser Ile Ser Ser Ser Asn Leu His
1               5                   10

<210> SEQ ID NO 31
<211> LENGTH: 21
<212> TYPE: DNA
<213> ORGANISM: Mus musculus

<400> SEQUENCE: 31
ggcacatcca accttgcttc t                                               21

<210> SEQ ID NO 32
<211> LENGTH: 7
<212> TYPE: PRT
<213> ORGANISM: Mus musculus

<400> SEQUENCE: 32

Gly Thr Ser Asn Leu Ala Ser
1               5

<210> SEQ ID NO 33
<211> LENGTH: 27
<212> TYPE: DNA
<213> ORGANISM: Mus musculus

<400> SEQUENCE: 33
caacagtgga gtagttaccc gctcacg                                         27

<210> SEQ ID NO 34
<211> LENGTH: 9
<212> TYPE: PRT
<213> ORGANISM: Mus musculus

<400> SEQUENCE: 34

Gln Gln Trp Ser Ser Tyr Pro Leu Thr
1               5

<210> SEQ ID NO 35
<211> LENGTH: 324
<212> TYPE: DNA
<213> ORGANISM: Mus musculus

<400> SEQUENCE: 35
cgggctgatg ctgcaccaac tgtatccatc ttcccaccat ccagtgagca gttaacatct    60
ggaggtgcct cagtcgtgtg cttcttgaac aacttctacc ccaaagacat caatgtcaag   120
tggaagattg atggcagtga acgacaaaat ggcgtcctga cagttggac tgatcaggac    180 agcaaagaca gcacctacag catgagcagc accctcacgt tgaccaagga cgagtatgaa   240
cgacataaca gctatacctg tgaggccact cacaagacat caacttcacc cattgtcaag   300
agcttcaaca ggaatgagtg ttag                                           324
```

-continued

```
<210> SEQ ID NO 36
<211> LENGTH: 107
<212> TYPE: PRT
<213> ORGANISM: Mus musculus

<400> SEQUENCE: 36
```

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

```
<210> SEQ ID NO 37
<211> LENGTH: 34
<212> TYPE: DNA
<213> ORGANISM: Artificial Sequence
<220> FEATURE:
<223> OTHER INFORMATION: Synthetic primer sequence

<400> SEQUENCE: 37
taacccgggc caccatgatg gggctcttcc ccag                          34

<210> SEQ ID NO 38
<211> LENGTH: 35
<212> TYPE: DNA
<213> ORGANISM: Artificial Sequence
<220> FEATURE:
<223> OTHER INFORMATION: Synthetic primer sequence

<400> SEQUENCE: 38
ttagcggccg cttatcatat tagacgggag caagg                         35

<210> SEQ ID NO 39
<211> LENGTH: 3000
<212> TYPE: DNA
<213> ORGANISM: Homo sapiens

<400> SEQUENCE: 39 atgatgggc tcttccccag aactacaggg gctctggcca tcttcgtggt ggtcatattg     60
gttcatggag aattgcgaat agagactaaa ggtcaatatg atgaagaaga gatgactatg    120
caacaagcta aagaaggca aaacgtgaa tgggtgaaat tgccaaaacc ctgcagagaa      180
ggagaagata actcaaaaag aaacccaatt gccaagatta cttcagatta ccaagcaacc    240
cagaaaatca cctaccgaat ctctggagtg ggaatcgatc agccgccttt tggaatcttt    300
gttgttgaca aaaacactgg agatattaac ataacagcta tagtcgaccg ggaggaaact    360
ccaagcttcc tgatcacatg tcgggctcta atgcccaag actagatgt agagaaacca     420 cttatactaa cggttaaaat tttggatatt aatgataatc ctccagtatt ttcacaacaa    480
attttcatgg gtgaaattga agaaatagt gcctcaaact cactggtgat gatactaaat    540
gccacagatg cagatgaacc aaaccacttg aattctaaaa ttgccttcaa aattgtctct    600
```

```
caggaaccag caggcacacc catgttcctc ctaagcagaa acactgggga agtccgtact    660
ttgaccaatt ctcttgaccg agagcaagct agcagctatc gtctggttgt gagtggtgca    720
gacaaagatg gagaaggact atcaactcaa tgtgaatgta atattaaagt gaaagatgtc    780
aacgataact tcccaatgtt tagagactct cagtattcag cacgtattga agaaaatatt    840
ttaagttctg aattacttcg atttcaagta acagatttgg atgaagagta cacagataat    900
tggcttgcag tatatttctt tacctctggg aatgaaggaa attggtttga aatacaaact    960
gatcctagaa ctaatgaagg catcctgaaa gtggtgaagg ctctagatta tgaacaacta   1020
caaagcgtga aacttagtat tgctgtcaaa acaaagctg aatttcacca atcagttatc    1080
tctcgatacc gagttcagtc aaccccagtc acaattcagg taataaatgt aagagaagga   1140
attgcattcc gtcctgcttc caagacattt actgtgcaaa aaggcataag tagcaaaaaa   1200
ttggtggatt atatcctggg aacatatcaa gccatcgatg aggacactaa caaagctgcc   1260
tcaaatgtca aatatgtcat gggacgtaac gatggtggat acctaatgat tgattcaaaa   1320
actgctgaaa tcaaatttgt caaaaatatg aaccgagatt ctactttcat agttaacaaa   1380
acaatcacag ctgaggttct ggccatagat gaatacacgg gtaaaacttc tacaggcacg   1440
gtatatgtta gagtacccga tttcaatgac aattgtccaa cagctgtcct cgaaaaagat   1500
gcagtttgca gttcttcacc ttccgtggtt gtctccgcta aacactgaa taatagatac    1560 actggcccct atacatttgc actggaagat caacctgtaa agttgcctgc cgtatggagt   1620
atcacaaccc tcaatgctac ctcggccctc ctcagagccc aggaacagat acctcctgga   1680
gtataccaca tctccctggt acttacagac agtcagaaca tcggtgtga gatgccacgc    1740 agcttgacac tggaagtctg tcagtgtgac aacaggggca tctgtggaac ttcttaccca   1800
accacaagcc ctgggaccag gtatggcagg ccgcactcag ggaggctggg gcctgccgcc   1860
atcggcctgc tgctccttgg tctcctgctg ctgctgttgg ccccccttct gctgttgacc   1920
tgtgactgtg ggcaggttc tactggggga gtgacaggtg gttttatccc agttcctgat    1980
ggctcagaag gaacaattca tcagtgggga attgaaggag cccatcctga agacaaggaa   2040
atcacaaata tttgtgtgcc tcctgtaaca gccaatggag ccgatttcat ggaaagttct   2100
gaagtttgta caaatacgta tgccagaggc acagcggtgg aaggcacttc aggaatggaa   2160
atgaccacta agcttggagc agccactgaa tctggaggtg ctgcaggctt tgcaacaggg   2220
acagtgtcag gagctgcttc aggattcgga gcagccactg agttggcat ctgttcctca    2280 gggcagtctg gaaccatgag aacaaggcat tccactggag gaaccaataa ggactacgct   2340 gatgggcga taagcatgaa ttttctggac tcctactttt ctcagaaagc atttgcctgt    2400
gcggaggaag acgatggcca ggaagcaaat gactgcttgt tgatctatga taatgaaggc   2460
gcagatgcca ctggttctcc tgtgggctcc gtgggttgtt gcagttttat tgctgatgac   2520
ctggatgaca gcttcttgga ctcacttgga cccaaattta aaaacttgc agagataagc    2580 cttggtgttg atggtgaagg caaagaagtt cagccaccct ctaaagacag cggttatggg   2640
attgaatcct gtggccatcc catagaagtc cagcagacag gatttgttaa gtgccagact   2700
ttgtcaggaa gtcaaggagc ttctgctttg tccgcctctg gtctgtcca gccagctgtt    2760 tccatccctg accctctgca gcatggtaac tatttagtaa cggagactta ctcggcttct   2820
ggttccctcg tgcaaccttc cactgcaggc tttgatccac ttctcacaca aaatgtgata   2880
gtgacagaaa gggtgatctg tcccatttcc agtgttcctg caacctagc tggcccaacg    2940
```
cagctacgag ggtcacatac tatgctctgt acagaggatc cttgctcccg tctaatatga    3000

<210> SEQ ID NO 40
<211> LENGTH: 999
<212> TYPE: PRT
<213> ORGANISM: Homo sapiens

<400> SEQUENCE: 40

Met Met Gly Leu Phe Pro Arg Thr Thr Gly Ala Leu Ala Ile Phe Val
1               5                   10                  15

Val Val Ile Leu Val His Gly Glu Leu Arg Ile Glu Thr Lys Gly Gln
            20                  25                  30

Tyr Asp Glu Glu Glu Met Thr Met Gln Gln Ala Lys Arg Arg Gln Lys
        35                  40                  45

Arg Glu Trp Val Lys Phe Ala Lys Pro Cys Arg Glu Gly Glu Asp Asn
    50                  55                  60

Ser Lys Arg Asn Pro Ile Ala Lys Ile Thr Ser Asp Tyr Gln Ala Thr
65                  70                  75                  80

Gln Lys Ile Thr Tyr Arg Ile Ser Gly Val Gly Ile Asp Gln Pro Pro
                85                  90                  95

Phe Gly Ile Phe Val Val Asp Lys Asn Thr Gly Asp Ile Asn Ile Thr
            100                 105                 110

Ala Ile Val Asp Arg Glu Glu Thr Pro Ser Phe Leu Ile Thr Cys Arg
        115                 120                 125

Ala Leu Asn Ala Gln Gly Leu Asp Val Glu Lys Pro Leu Ile Leu Thr
    130                 135                 140

Val Lys Ile Leu Asp Ile Asn Asp Asn Pro Pro Val Phe Ser Gln Gln
145                 150                 155                 160

Ile Phe Met Gly Glu Ile Glu Glu Asn Ser Ala Ser Asn Ser Leu Val
                165                 170                 175

Met Ile Leu Asn Ala Thr Asp Ala Asp Glu Pro Asn His Leu Asn Ser
            180                 185                 190

Lys Ile Ala Phe Lys Ile Val Ser Gln Glu Pro Ala Gly Thr Pro Met
        195                 200                 205

Phe Leu Leu Ser Arg Asn Thr Gly Glu Val Arg Thr Leu Thr Asn Ser
    210                 215                 220

Leu Asp Arg Glu Gln Ala Ser Ser Tyr Arg Leu Val Val Ser Gly Ala
225                 230                 235                 240

Asp Lys Asp Gly Glu Gly Leu Ser Thr Gln Cys Glu Cys Asn Ile Lys
                245                 250                 255

Val Lys Asp Val Asn Asp Asn Phe Pro Met Phe Arg Asp Ser Gln Tyr
            260                 265                 270

Ser Ala Arg Ile Glu Glu Asn Ile Leu Ser Ser Glu Leu Leu Arg Phe
        275                 280                 285

Gln Val Thr Asp Leu Asp Glu Glu Tyr Thr Asp Asn Trp Leu Ala Val
    290                 295                 300

Tyr Phe Phe Thr Ser Gly Asn Glu Gly Asn Trp Phe Glu Ile Gln Thr
305                 310                 315                 320

Asp Pro Arg Thr Asn Glu Gly Ile Leu Lys Val Val Lys Ala Leu Asp
                325                 330                 335

Tyr Glu Gln Leu Gln Ser Val Lys Leu Ser Ile Ala Val Lys Asn Lys
            340                 345                 350

Ala Glu Phe His Gln Ser Val Ile Ser Arg Tyr Arg Val Gln Ser Thr
        355                 360                 365

-continued

Pro Val Thr Ile Gln Val Ile Asn Val Arg Glu Gly Ile Ala Phe Arg
370                 375                 380

Pro Ala Ser Lys Thr Phe Thr Val Gln Lys Gly Ile Ser Ser Lys Lys
385                 390                 395                 400

Leu Val Asp Tyr Ile Leu Gly Thr Tyr Gln Ala Ile Asp Glu Asp Thr
            405                 410                 415

Asn Lys Ala Ala Ser Asn Val Lys Tyr Val Met Gly Arg Asn Asp Gly
            420                 425                 430

Gly Tyr Leu Met Ile Asp Ser Lys Thr Ala Glu Ile Lys Phe Val Lys
            435                 440                 445

Asn Met Asn Arg Asp Ser Thr Phe Ile Val Asn Lys Thr Ile Thr Ala
450                 455                 460

Glu Val Leu Ala Ile Asp Glu Tyr Thr Gly Lys Thr Ser Thr Gly Thr
465                 470                 475                 480

Val Tyr Val Arg Val Pro Asp Phe Asn Asp Asn Cys Pro Thr Ala Val
            485                 490                 495

Leu Glu Lys Asp Ala Val Cys Ser Ser Pro Ser Val Val Ser
            500                 505                 510

Ala Arg Thr Leu Asn Asn Arg Tyr Thr Gly Pro Tyr Thr Phe Ala Leu
            515                 520                 525

Glu Asp Gln Pro Val Lys Leu Pro Ala Val Trp Ser Ile Thr Thr Leu
530                 535                 540

Asn Ala Thr Ser Ala Leu Leu Arg Ala Gln Glu Gln Ile Pro Pro Gly
545                 550                 555                 560

Val Tyr His Ile Ser Leu Val Leu Thr Asp Ser Gln Asn Asn Arg Cys
            565                 570                 575

Glu Met Pro Arg Ser Leu Thr Leu Glu Val Cys Gln Cys Asp Asn Arg
            580                 585                 590

Gly Ile Cys Gly Thr Ser Tyr Pro Thr Thr Ser Pro Gly Thr Arg Tyr
            595                 600                 605

Gly Arg Pro His Ser Gly Arg Leu Gly Pro Ala Ala Ile Gly Leu Leu
            610                 615                 620

Leu Leu Gly Leu Leu Leu Leu Leu Ala Pro Leu Leu Leu Leu Thr
625                 630                 635                 640

Cys Asp Cys Gly Ala Gly Ser Thr Gly Val Thr Gly Gly Phe Ile
            645                 650                 655

Pro Val Pro Asp Gly Ser Glu Gly Thr Ile His Gln Trp Gly Ile Glu
            660                 665                 670

Gly Ala His Pro Glu Asp Lys Glu Ile Thr Asn Ile Cys Val Pro Pro
            675                 680                 685

Val Thr Ala Asn Gly Ala Asp Phe Met Glu Ser Ser Glu Val Cys Thr
690                 695                 700

Asn Thr Tyr Ala Arg Gly Thr Ala Val Glu Gly Thr Ser Gly Met Glu
705                 710                 715                 720

Met Thr Thr Lys Leu Gly Ala Ala Thr Glu Ser Gly Ala Ala Gly
            725                 730                 735

Phe Ala Thr Gly Thr Val Ser Gly Ala Ala Ser Gly Phe Gly Ala Ala
            740                 745                 750

Thr Gly Val Gly Ile Cys Ser Ser Gly Gln Ser Gly Thr Met Arg Thr
            755                 760                 765

Arg His Ser Thr Gly Gly Thr Asn Lys Asp Tyr Ala Asp Gly Ala Ile
770                 775                 780

Ser Met Asn Phe Leu Asp Ser Tyr Phe Ser Gln Lys Ala Phe Ala Cys

| | | | |
|---|---|---|---|
| | 785 | 790 | 795 | 800 |

Ala Glu Glu Asp Asp Gly Gln Glu Ala Asn Asp Cys Leu Leu Ile Tyr
                    805                 810                 815

Asp Asn Glu Gly Ala Asp Ala Thr Gly Ser Pro Val Gly Ser Val Gly
                820                 825                 830

Cys Cys Ser Phe Ile Ala Asp Leu Asp Asp Ser Phe Leu Asp Ser
            835                 840                 845

Leu Gly Pro Lys Phe Lys Lys Leu Ala Glu Ile Ser Leu Gly Val Asp
        850                 855                 860

Gly Glu Gly Lys Glu Val Gln Pro Pro Ser Lys Asp Ser Gly Tyr Gly
865                 870                 875                 880

Ile Glu Ser Cys Gly His Pro Ile Glu Val Gln Gln Thr Gly Phe Val
                885                 890                 895

Lys Cys Gln Thr Leu Ser Gly Ser Gln Gly Ala Ser Ala Leu Ser Ala
                900                 905                 910

Ser Gly Ser Val Gln Pro Ala Val Ser Ile Pro Asp Pro Leu Gln His
            915                 920                 925

Gly Asn Tyr Leu Val Thr Glu Thr Tyr Ser Ala Ser Gly Ser Leu Val
        930                 935                 940

Gln Pro Ser Thr Ala Gly Phe Asp Pro Leu Leu Thr Gln Asn Val Ile
945                 950                 955                 960

Val Thr Glu Arg Val Ile Cys Pro Ile Ser Ser Val Pro Gly Asn Leu
                965                 970                 975

Ala Gly Pro Thr Gln Leu Arg Gly Ser His Thr Met Leu Cys Thr Glu
            980                 985                 990

Asp Pro Cys Ser Arg Leu Ile
        995

```
<210> SEQ ID NO 41
<211> LENGTH: 2550
<212> TYPE: DNA
<213> ORGANISM: Artificial Sequence
<220> FEATURE:
<223> OTHER INFORMATION: Synthetic nucleotide sequence

<400> SEQUENCE: 41 atgatgggc tcttccccag aactacaggg gctctggcca tcttcgtggt ggtcatattg      60
gttcatggag aattgcgaat agagactaaa ggtcaatatg atgaagaaga gatgactatg     120
caacaagcta aagaaggca aaaacgtgaa tgggtgaaat tgccaaaacc ctgcagagaa      180
ggagaagata actcaaaaag aaacccaatt gccaagatta cttcagatta ccaagcaacc     240
cagaaaatca cctaccgaat ctctggagtg gaatcgatc agccgccttt tggaatcttt      300
gttgttgata aaacactgg agatattaac ataacagcta tagtcgaccg ggaggaaact      360
ccaagcttcc tgatcacatg tcgggctcta aatgcccaag actagatgt agagaaacca     420 cttatactaa cggttaaaat tttggatatt aatgataatc ctccagtatt ttcacaacaa     480
attttcatgg gtgaaattga agaaaatagt gcctcaaact cactggtgat gatactaaat     540
gccacagatg cagatgaacc aaaccacttg aactctaaaa ttgccttcaa aattgtctct     600
caggaaccag caggcacacc catgttcctc ctaagcagaa acactgggga agtccgtact     660
ttgaccaatt ctcttgaccg agagcaagct agcagctatc gtctggttgt gagtggtgca     720
gacaaagatg gagaaggact atcaactcaa tgtgaatgta atattaaagt gaaagatgtc     780
aacgataact tcccaatgtt tagagactct cagtattcag cacgtattga agaaaatatt     840
```

-continued

```
ttaagttctg aattacttcg atttcaagta acagatttgg atgaagagta cacagataat    900
tggcttgcag tatatttctt tacctctggg aatgaaggaa attggtttga aatacaaact    960
gatcctagaa ctaatgaagg catcctgaaa gtggtgaagg ctctagatta tgaacaacta   1020
caaagcgtga aacttagtat tgctgtcaaa acaaaagctg aatttcacca atcagttatc   1080
tctcgatacc gagttcagtc aaccccagtc acaattcagg taataaatgt aagagaagga   1140
attgcattcc gtcctgcttc caagacattt actgtgcaaa aaggcataag tagcaaaaaa   1200
ttggtggatt atatcctggg aacatatcaa gccatcgatg aggacactaa caaagctgcc   1260
tcaaatgtca aatatgtcat gggacgtaac gatggtggat acctaatgat tgattcaaaa   1320
actgctgaaa tcaaatttgt caaaaatatg aaccgagatt ctactttcat agttaacaaa   1380
acaatcacag ctgaggttct ggccatagat gaatacacgg gtaaaacttc tacaggcacg   1440
gtatatgtta gagtacccga tttcaatgac aattgtccaa cagctgtcct cgaaaaagat   1500
gcagtttgca gttcttcacc ttccgtggtt gtctccgcta gaacactgaa taatagatac   1560
actggcccct atacatttgc actggaagat caacctgtaa agttgcctgc cgtatggagt   1620
atcacaaccc tcaatgctac ctcggccctc ctcagagccc aggaacagat acctcctgga   1680
gtataccaca tctccctggt acttacagac agtcagaaca tcggtgtga  gatgccacgc   1740 agcttgacac tggaagtctg tcagtgtgac aacaggggca tctgtggaac ttcttaccca   1800
accacaagcc ctgggaccag gtatggcagg ccgcactcag ggaggctgga acctcgcgga   1860
ccgacaatca agccctgtcc tccatgcaaa tgcccagcac ctaacctctt gggtggacca   1920
tccgtcttca tcttccctcc aaagatcaag gatgtactca tgatctccct gagccccata   1980
gtcacatgtg tggtggtgga tgtgagcgag gatgacccag atgtccagat cagctggttt   2040
gtgaacaacg tggaagtaca cacagctcag acacaaaccc atagagagga ttacaacagt   2100
actctccggg tggtcagtgc cctccccatc cagcaccagg actggatgag tggcaaggag   2160
ttcaaatgca aggtcaacaa caaagacctc cagcgcccca tcgagagaac catctcaaaa   2220
cccaaagggt cagtaagagc tccacaggta tatgtcttgc ctccaccaga agaagagatg   2280
actaagaaac aggtcactct gacctgcatg gtcacagact tcatgcctga agacatttac   2340
gtggagtgga ccaacaacgg gaaaacagag ctaaactaca gaacactgac cagtcctgtg   2400
gactctgatg gttcttactt catgtacagc aagctgagag tggaaaagaa gaactgggtg   2460
gaaagaaata gctactcctg ttcagtggtc cacgagggtc tgcacaatca ccacacgact   2520
aagagcttct cccggactcc gggtaaatga                                    2550
```

<210> SEQ ID NO 42
<211> LENGTH: 849
<212> TYPE: PRT
<213> ORGANISM: Artificial Sequence
<220> FEATURE:
<223> OTHER INFORMATION: Synthetic peptide sequence

<400> SEQUENCE: 42

```
Met Met Gly Leu Phe Pro Arg Thr Thr Gly Ala Leu Ala Ile Phe Val
1               5                   10                  15

Val Val Ile Leu Val His Gly Glu Leu Arg Ile Glu Thr Lys Gly Gln
                20                  25                  30

Tyr Asp Glu Glu Glu Met Thr Met Gln Gln Ala Lys Arg Arg Gln Lys
            35                  40                  45

Arg Glu Trp Val Lys Phe Ala Lys Pro Cys Arg Glu Gly Glu Asp Asn
        50                  55                  60
```

```
Ser Lys Arg Asn Pro Ile Ala Lys Ile Thr Ser Asp Tyr Gln Ala Thr
 65                  70                  75                  80

Gln Lys Ile Thr Tyr Arg Ile Ser Gly Val Gly Ile Asp Gln Pro Pro
                 85                  90                  95

Phe Gly Ile Phe Val Val Asp Lys Asn Thr Gly Asp Ile Asn Ile Thr
                100                 105                 110

Ala Ile Val Asp Arg Glu Glu Thr Pro Ser Phe Leu Ile Thr Cys Arg
                115                 120                 125

Ala Leu Asn Ala Gln Gly Leu Asp Val Glu Lys Pro Leu Ile Leu Thr
                130                 135                 140

Val Lys Ile Leu Asp Ile Asn Asp Asn Pro Pro Val Phe Ser Gln Gln
145                 150                 155                 160

Ile Phe Met Gly Glu Ile Glu Glu Asn Ser Ala Ser Asn Ser Leu Val
                165                 170                 175

Met Ile Leu Asn Ala Thr Asp Ala Asp Glu Pro Asn His Leu Asn Ser
                180                 185                 190

Lys Ile Ala Phe Lys Ile Val Ser Gln Glu Pro Ala Gly Thr Pro Met
                195                 200                 205

Phe Leu Leu Ser Arg Asn Thr Gly Glu Val Arg Thr Leu Thr Asn Ser
210                 215                 220

Leu Asp Arg Glu Gln Ala Ser Ser Tyr Arg Leu Val Val Ser Gly Ala
225                 230                 235                 240

Asp Lys Asp Gly Glu Gly Leu Ser Thr Gln Cys Glu Cys Asn Ile Lys
                245                 250                 255

Val Lys Asp Val Asn Asp Asn Phe Pro Met Phe Arg Asp Ser Gln Tyr
                260                 265                 270

Ser Ala Arg Ile Glu Glu Asn Ile Leu Ser Ser Glu Leu Leu Arg Phe
                275                 280                 285

Gln Val Thr Asp Leu Asp Glu Glu Tyr Thr Asp Asn Trp Leu Ala Val
                290                 295                 300

Tyr Phe Phe Thr Ser Gly Asn Glu Gly Asn Trp Phe Glu Ile Gln Thr
305                 310                 315                 320

Asp Pro Arg Thr Asn Glu Gly Ile Leu Lys Val Val Lys Ala Leu Asp
                325                 330                 335

Tyr Glu Gln Leu Gln Ser Val Lys Leu Ser Ile Ala Val Lys Asn Lys
                340                 345                 350

Ala Glu Phe His Gln Ser Val Ile Ser Arg Tyr Arg Val Gln Ser Thr
                355                 360                 365

Pro Val Thr Ile Gln Val Ile Asn Val Arg Glu Gly Ile Ala Phe Arg
                370                 375                 380

Pro Ala Ser Lys Thr Phe Thr Val Gln Lys Gly Ile Ser Ser Lys Lys
385                 390                 395                 400

Leu Val Asp Tyr Ile Leu Gly Thr Tyr Gln Ala Ile Asp Glu Asp Thr
                405                 410                 415

Asn Lys Ala Ala Ser Asn Val Lys Tyr Val Met Gly Arg Asn Asp Gly
                420                 425                 430

Gly Tyr Leu Met Ile Asp Ser Lys Thr Ala Glu Ile Lys Phe Val Lys
                435                 440                 445

Asn Met Asn Arg Asp Ser Thr Phe Ile Val Asn Lys Thr Ile Thr Ala
                450                 455                 460

Glu Val Leu Ala Ile Asp Glu Tyr Thr Gly Lys Thr Ser Thr Gly Thr
465                 470                 475                 480
```

```
Val Tyr Val Arg Val Pro Asp Phe Asn Asp Asn Cys Pro Thr Ala Val
            485                 490                 495

Leu Glu Lys Asp Ala Val Cys Ser Ser Ser Pro Ser Val Val Ser
        500                 505                 510

Ala Arg Thr Leu Asn Asn Arg Tyr Thr Gly Pro Tyr Thr Phe Ala Leu
            515                 520                 525

Glu Asp Gln Pro Val Lys Leu Pro Ala Val Trp Ser Ile Thr Thr Leu
        530                 535                 540

Asn Ala Thr Ser Ala Leu Leu Arg Ala Gln Glu Gln Ile Pro Pro Gly
545                 550                 555                 560

Val Tyr His Ile Ser Leu Val Leu Thr Asp Ser Gln Asn Asn Arg Cys
            565                 570                 575

Glu Met Pro Arg Ser Leu Thr Leu Glu Val Cys Gln Cys Asp Asn Arg
            580                 585                 590

Gly Ile Cys Gly Thr Ser Tyr Pro Thr Thr Ser Pro Gly Thr Arg Tyr
            595                 600                 605

Gly Arg Pro His Ser Gly Arg Leu Glu Pro Arg Gly Pro Thr Ile Lys
            610                 615                 620

Pro Cys Pro Pro Cys Lys Cys Pro Ala Pro Asn Leu Leu Gly Gly Pro
625                 630                 635                 640

Ser Val Phe Ile Phe Pro Pro Lys Ile Lys Asp Val Leu Met Ile Ser
            645                 650                 655

Leu Ser Pro Ile Val Thr Cys Val Val Val Asp Val Ser Glu Asp Asp
            660                 665                 670

Pro Asp Val Gln Ile Ser Trp Phe Val Asn Asn Val Glu Val His Thr
            675                 680                 685

Ala Gln Thr Gln Thr His Arg Glu Asp Tyr Asn Ser Thr Leu Arg Val
        690                 695                 700

Val Ser Ala Leu Pro Ile Gln His Gln Asp Trp Met Ser Gly Lys Glu
705                 710                 715                 720

Phe Lys Cys Lys Val Asn Asn Lys Asp Leu Pro Ala Pro Ile Glu Arg
            725                 730                 735

Thr Ile Ser Lys Pro Lys Gly Ser Val Arg Ala Pro Gln Val Tyr Val
            740                 745                 750

Leu Pro Pro Pro Glu Glu Glu Met Thr Lys Lys Gln Val Thr Leu Thr
            755                 760                 765

Cys Met Val Thr Asp Phe Met Pro Glu Asp Ile Tyr Val Glu Trp Thr
            770                 775                 780

Asn Asn Gly Lys Thr Glu Leu Asn Tyr Lys Asn Thr Glu Pro Val Leu
785                 790                 795                 800

Asp Ser Asp Gly Ser Tyr Phe Met Tyr Ser Lys Leu Arg Val Glu Lys
            805                 810                 815

Lys Asn Trp Val Glu Arg Asn Ser Tyr Ser Cys Ser Val Val His Glu
            820                 825                 830

Gly Leu His Asn His His Thr Thr Lys Ser Phe Ser Arg Thr Pro Gly
            835                 840                 845

Lys
```

<210> SEQ ID NO 43
<211> LENGTH: 24
<212> TYPE: DNA
<213> ORGANISM: Artificial Sequence
<220> FEATURE:
<223> OTHER INFORMATION: Synthetic oligonucleotide sequence

<400> SEQUENCE: 43 cagggggccag tggatagact gatg                                          24

<210> SEQ ID NO 44
<211> LENGTH: 23
<212> TYPE: DNA
<213> ORGANISM: Artificial Sequence
<220> FEATURE:
<223> OTHER INFORMATION: Synthetic oligonucleotide sequence

<400> SEQUENCE: 44
gctcactgga tggtgggaag atg                                            23

<210> SEQ ID NO 45
<211> LENGTH: 396
<212> TYPE: DNA
<213> ORGANISM: Mus musculus

<400> SEQUENCE: 45
atgggatgga actggatctt tattttaatc ctgtcagtaa ctacaggtgt ccactctgag     60
gtccagctgc agcagtctgg acctgagctg gtgaagcctg gggcttcagt gaagatatcc    120
tgcaaggctt ctggttactc attcactgcc tactacatgc actgggtgaa gcaaagtcct    180
gaaaagtgcc ttgagtggat tggacagatt aatcctagca ctggtggtac tacctacaac    240
cagaagttca aggccaaggc acattgact gtagacaaat cctccagcac agcctacatg     300
cagctcaaga gcctgacatc tgaggactct gcagtctatt attgtgcaag atggggtgac    360
tcttggggcc aaggcaccac tctcacagtc tcctca                              396

<210> SEQ ID NO 46
<211> LENGTH: 132
<212> TYPE: PRT
<213> ORGANISM: Mus musculus

<400> SEQUENCE: 46

Met Gly Trp Asn Trp Ile Phe Ile Leu Ile Leu Ser Val Thr Thr Gly
1               5                   10                  15

Val His Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

Thr Ala Tyr Tyr Met His Trp Val Lys Gln Ser Pro Glu Lys Cys Leu
    50                  55                  60

Glu Trp Ile Gly Gln Ile Asn Pro Ser Thr Gly Gly Thr Thr Tyr Asn
65                  70                  75                  80

Gln Lys Phe Lys Ala Lys Ala Thr Leu Thr Val Asp Lys Ser Ser Ser
                85                  90                  95

Thr Ala Tyr Met Gln Leu Lys Ser Leu Thr Ser Glu Asp Ser Ala Val
            100                 105                 110

Tyr Tyr Cys Ala Arg Trp Gly Asp Ser Trp Gly Gln Gly Thr Thr Leu
        115                 120                 125

Thr Val Ser Ser
    130

<210> SEQ ID NO 47
<211> LENGTH: 393
<212> TYPE: DNA
<213> ORGANISM: Mus musculus

<400> SEQUENCE: 47

```
atggagacag acacactcct gctatgggtg ctgctgctct gggttccagg ctccactggt    60
gacattgtgc tcacccaatc tccagcttct ttggctgtgt ctctagggca gagtgtcacc   120
atctcctgca gagccagtga aagtgttgaa tattatggca ctagtttaat gcagtggtac   180
caacagaaac caggacagcc acccaaactc ctcatctatg gtgcatccga cgtagaatct   240
ggggtccctg ccaggtttag tggcagtggg tctgggacag acttcagcct caacatccat   300
cctgtggagg aggatgatat tgcaatgtat ttctgtcagc aaagtaggaa ggttccgtat   360
acgttcggat cggggaccaa gttggaaata aaa                                393
```

<210> SEQ ID NO 48
<211> LENGTH: 131
<212> TYPE: PRT
<213> ORGANISM: Mus musculus

<400> SEQUENCE: 48

```
Met Glu Thr Asp Thr Leu Leu Leu Trp Val Leu Leu Leu Trp Val Pro
1               5                   10                  15
Gly Ser Thr Gly Asp Ile Val Leu Thr Gln Ser Pro Ala Ser Leu Ala
            20                  25                  30
Val Ser Leu Gly Gln Ser Val Thr Ile Ser Cys Arg Ala Ser Glu Ser
        35                  40                  45
Val Glu Tyr Tyr Gly Thr Ser Leu Met Gln Trp Tyr Gln Gln Lys Pro
    50                  55                  60
Gly Gln Pro Pro Lys Leu Leu Ile Tyr Gly Ala Ser Asp Val Glu Ser
65                  70                  75                  80
Gly Val Pro Ala Arg Phe Ser Gly Ser Gly Ser Gly Thr Asp Phe Ser
                85                  90                  95
Leu Asn Ile His Pro Val Glu Glu Asp Asp Ile Ala Met Tyr Phe Cys
            100                 105                 110
Gln Gln Ser Arg Lys Val Pro Tyr Thr Phe Gly Ser Gly Thr Lys Leu
        115                 120                 125
Glu Ile Lys
    130
```

<210> SEQ ID NO 49
<211> LENGTH: 426
<212> TYPE: DNA
<213> ORGANISM: Mus musculus

<400> SEQUENCE: 49

```
atggaatcta actggatact tcctttatt ctgtcggtaa cttcagggt ctactcagag      60
gttcagctcc agcagtctgg gactgtgctg gcaaggcctg ggcttcagt gaagatgtcc    120
tgcaaggctt ctggctacac ctttgccagc tactggattc actgggtaaa gcagaggcct   180
ggacagggtc tggaatggat tggctctatt tatcctggaa atagtgatac tacctacaac   240
cagaagttca gggcaaggc caaactgact gtagtcacat ctgccagctc tgcctacatg   300
gagctcagca gcctgacaaa tgaggactct gcggtctatt actgtacaga acctacttac   360
tatagttacg acgattacta tgctatggac tattggggtc aaggaacctc agtcaccgtc   420
tcctca                                                              426
```

<210> SEQ ID NO 50
<211> LENGTH: 142
<212> TYPE: PRT

<213> ORGANISM: Mus musculus

<400> SEQUENCE: 50

Met Glu Ser Asn Trp Ile Leu Pro Phe Ile Leu Ser Val Thr Ser Gly
1               5                   10                  15

Val Tyr Ser Glu Val Gln Leu Gln Gln Ser Gly Thr Val Leu Ala Arg
            20                  25                  30

Pro Gly Ala Ser Val Lys Met Ser Cys Lys Ala Ser Gly Tyr Thr Phe
        35                  40                  45

Ala Ser Tyr Trp Ile His Trp Val Lys Gln Arg Pro Gly Gln Gly Leu
    50                  55                  60

Glu Trp Ile Gly Ser Ile Tyr Pro Gly Asn Ser Asp Thr Thr Tyr Asn
65                  70                  75                  80

Gln Lys Phe Lys Gly Lys Ala Lys Leu Thr Val Thr Ser Ala Ser
                85                  90                  95

Ser Ala Tyr Met Glu Leu Ser Ser Leu Thr Asn Glu Asp Ser Ala Val
            100                 105                 110

Tyr Tyr Cys Thr Glu Pro Thr Tyr Ser Tyr Asp Asp Tyr Tyr Ala
        115                 120                 125

Met Asp Tyr Trp Gly Gln Gly Thr Ser Val Thr Val Ser Ser
    130                 135                 140

<210> SEQ ID NO 51
<211> LENGTH: 390
<212> TYPE: DNA
<213> ORGANISM: Mus musculus

<400> SEQUENCE: 51
atggattttc atgtgcagat tttcagcttc atgctaatca gtgtcacagt catattgtcc      60
agtggagaaa ttgtgctcac ccagtctcca gcactcatgg ctgcatctcc aggggagaag     120
gtcaccatca cctgcagtgt cagctcaagt ataagttcca gcaacttaca ctggtaccag     180
cagaagtcag gaacctcccc caaaccctgg atttatggca catccaacct tgcttctgga     240
gtccctgttc gcttcagtgg cagtggatct gggacctctt attctctcac aatcagcacc     300
atggaggctg aagatgctgc cacttattac tgtcaacagt ggagtagtta cccgctcacg     360
ttcggtgctg ggaccaagct ggagctgaaa                                      390

<210> SEQ ID NO 52
<211> LENGTH: 130
<212> TYPE: PRT
<213> ORGANISM: Mus musculus

<400> SEQUENCE: 52

Met Asp Phe His Val Gln Ile Phe Ser Phe Met Leu Ile Ser Val Thr
1               5                   10                  15

Val Ile Leu Ser Ser Gly Glu Ile Val Leu Thr Gln Ser Pro Ala Leu
            20                  25                  30

Met Ala Ala Ser Pro Gly Glu Lys Val Thr Ile Thr Cys Ser Val Ser
        35                  40                  45

Ser Ser Ile Ser Ser Ser Asn Leu His Trp Tyr Gln Gln Lys Ser Gly
    50                  55                  60

Thr Ser Pro Lys Pro Trp Ile Tyr Gly Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

```
               Thr Ile Ser Thr Met Glu Ala Glu Asp Ala Ala Thr Tyr Tyr Cys Gln
                           100                 105                 110

Gln Trp Ser Ser Tyr Pro Leu Thr Phe Gly Ala Gly Thr Lys Leu Glu
                       115                 120                 125

Leu Lys
                   130

<210> SEQ ID NO 53
<211> LENGTH: 32
<212> TYPE: DNA
<213> ORGANISM: Mus musculus

<400> SEQUENCE: 53
gccaaaacaa caccccatc agtctatcca ct                                      32

<210> SEQ ID NO 54
<211> LENGTH: 30
<212> TYPE: DNA
<213> ORGANISM: Mus musculus

<400> SEQUENCE: 54
cgggctgatg ctgcaccaac tgtatccatc                                        30

<210> SEQ ID NO 55
<211> LENGTH: 33
<212> TYPE: DNA
<213> ORGANISM: Mus musculus

<400> SEQUENCE: 55
gccaaaacga caccccatc tgtctatcca ctg                                     33

<210> SEQ ID NO 56
<211> LENGTH: 1407
<212> TYPE: DNA
<213> ORGANISM: Mus musculus

<400> SEQUENCE: 56
atgggatgga actggatctt tatttaatc ctgtcagtaa ctacaggtgt ccactctgag        60
gtccagctgc agcagtctgg acctgagctg gtgaagcctg ggcttcagt gaagatatcc       120 tgcaaggctt ctggttactc attcactgcc tactacatgc actgggtgaa gcaaagtcct     180
gaaaagtgcc ttgagtggat tggacagatt aatcctagca ctggtggtac tacctacaac     240
cagaagttca aggccaaggc cacattgact gtagacaaat cctccagcac agcctacatg     300
cagctcaaga gcctgacatc tgaggactct gcagtctatt attgtgcaag atgggggtgac    360 tcttggggcc aaggcaccac tctcacagtc tcctcagcca aaacaacacc cccatcagtc     420
tatccactgg ccctggggtg tggagataca actggttcct ctgtgactct gggatgcctg     480
gtcaagggct acttccctga gtcagtgact gtgacttgga actctggatc cctgtccagc     540
agtgtgcaca ccttcccagc tctcctgcag tctggactct acactatgag cagctcagtg     600
actgtcccct ccagcacctg gccaagtcag accgtcacct gcagcgttgc tcacccagcc     660
agcagcacca cggtggacaa aaaacttgag cccagcgggc ccatttcaac aatcaacccc     720
tgtcctccat gcaaggagtg tcacaaatgc ccagctccta acctcgaggg tggaccatcc     780
gtcttcatct tcctcccaaa tatcaaggat gtactcatga tctccctgac acccaaggtc     840
acgtgtgtgg tggtggatgt gagcgaggat gacccagacg tccagatcag ctggtttgtg     900
aacaacgtgg aagtacacac agctcagaca caaacccata gagaggatta caacagtact     960
```

```
atccgggtgg tcagtgccct ccccatccag caccaggact ggatgagtgg caaggagttc    1020
aaatgcaagg tcaacaacaa agacctccca tcacccatcg agagaaccat ctcaaaaatt    1080
aaagggctag tcagagctcc acaagtatac atcttgccgc caccagcaga gcagttgtcc    1140
aggaaagatg tcagtctcac ttgcctggtc gtgggcttca accctggaga catcagtgtg    1200
gagtggacca gcaatgggca tacagaggag aactacaagg acaccgcacc agtcctggac    1260
tctgacggtt cttacttcat atacagcaag ctcgatataa aacaagcaa gtgggagaaa     1320 acagattcct tctcatgcaa cgtgagacac gagggtctga aaaattacta cctgaagaag    1380
accatctccc ggtctccggg taaatga                                       1407
```

<210> SEQ ID NO 57
<211> LENGTH: 468
<212> TYPE: PRT
<213> ORGANISM: Mus musculus

<400> SEQUENCE: 57

```
Met Gly Trp Asn Trp Ile Phe Ile Leu Ile Leu Ser Val Thr Thr Gly
1               5                   10                  15

Val His Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

Thr Ala Tyr Tyr Met His Trp Val Lys Gln Ser Pro Glu Lys Cys Leu
    50                  55                  60

Glu Trp Ile Gly Gln Ile Asn Pro Ser Thr Gly Gly Thr Thr Tyr Asn
65                  70                  75                  80

Gln Lys Phe Lys Ala Lys Ala Thr Leu Thr Val Asp Lys Ser Ser Ser
                85                  90                  95

Thr Ala Tyr Met Gln Leu Lys Ser Leu Thr Ser Glu Asp Ser Ala Val
            100                 105                 110

Tyr Tyr Cys Ala Arg Trp Gly Asp Ser Trp Gly Gln Gly Thr Thr Leu
        115                 120                 125

Thr Val Ser Ser Ala Lys Thr Thr Pro Pro Ser Val Tyr Pro Leu Ala
    130                 135                 140

Pro Gly Cys Gly Asp Thr Thr Gly Ser Ser Val Thr Leu Gly Cys Leu
145                 150                 155                 160

Val Lys Gly Tyr Phe Pro Glu Ser Val Thr Val Thr Trp Asn Ser Gly
                165                 170                 175

Ser Leu Ser Ser Val His Thr Phe Pro Ala Leu Leu Gln Ser Gly
            180                 185                 190

Leu Tyr Thr Met Ser Ser Ser Val Thr Val Pro Ser Ser Thr Trp Pro
        195                 200                 205

Ser Gln Thr Val Thr Cys Ser Val Ala His Pro Ala Ser Ser Thr Thr
    210                 215                 220

Val Asp Lys Lys Leu Glu Pro Ser Gly Pro Ile Ser Thr Ile Asn Pro
225                 230                 235                 240

Cys Pro Pro Cys Lys Glu Cys His Lys Cys Pro Ala Pro Asn Leu Glu
                245                 250                 255

Gly Gly Pro Ser Val Phe Ile Phe Pro Pro Asn Ile Lys Asp Val Leu
            260                 265                 270

Met Ile Ser Leu Thr Pro Lys Val Thr Cys Val Val Val Asp Val Ser
        275                 280                 285

Glu Asp Asp Pro Asp Val Gln Ile Ser Trp Phe Val Asn Asn Val Glu
```

```
            290                 295                 300

Val His Thr Ala Gln Thr Gln Thr His Arg Glu Asp Tyr Asn Ser Thr
305                 310                 315                 320

Ile Arg Val Val Ser Ala Leu Pro Ile Gln His Gln Asp Trp Met Ser
                325                 330                 335

Gly Lys Glu Phe Lys Cys Lys Val Asn Asn Lys Asp Leu Pro Ser Pro
                340                 345                 350

Ile Glu Arg Thr Ile Ser Lys Ile Lys Gly Leu Val Arg Ala Pro Gln
            355                 360                 365

Val Tyr Ile Leu Pro Pro Pro Ala Glu Gln Leu Ser Arg Lys Asp Val
370                 375                 380

Ser Leu Thr Cys Leu Val Val Gly Phe Asn Pro Gly Asp Ile Ser Val
385                 390                 395                 400

Glu Trp Thr Ser Asn Gly His Thr Glu Glu Asn Tyr Lys Asp Thr Ala
                405                 410                 415

Pro Val Leu Asp Ser Asp Gly Ser Tyr Phe Ile Tyr Ser Lys Leu Asp
                420                 425                 430

Ile Lys Thr Ser Lys Trp Glu Lys Thr Asp Ser Phe Ser Cys Asn Val
            435                 440                 445

Arg His Glu Gly Leu Lys Asn Tyr Tyr Leu Lys Thr Ile Ser Arg
        450                 455                 460

Ser Pro Gly Lys
465

<210> SEQ ID NO 58
<211> LENGTH: 717
<212> TYPE: DNA
<213> ORGANISM: Mus musculus

<400> SEQUENCE: 58
atggagacag acacactcct gctatgggtg ctgctgctct gggttccagg ctccactggt      60
gacattgtgc tcacccaatc tccagcttct ttggctgtgt ctctagggca gagtgtcacc     120
atctcctgca gagccagtga aagtgttgaa tattatggca ctagtttaat gcagtggtac     180
caacagaaac aggacagcc acccaaactc ctcatctatg gtgcatccga cgtagaatct     240
ggggtccctg ccaggtttag tggcagtggg tctgggacag acttcagcct caacatccat     300
cctgtggagg aggatgatat tgcaatgtat ttctgtcagc aaagtaggaa ggttccgtat     360
acgttcggat cggggaccaa gttggaaata aaacgggctg atgctgcacc aactgtatcc     420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600 agcacccctca cgttgaccaa ggacgagtat gaacgacata cagctatac ctgtgaggcc     660 actcacaaga catcaacttc acccattgtc aagagcttca caggaatga gtgttag       717

<210> SEQ ID NO 59
<211> LENGTH: 238
<212> TYPE: PRT
<213> ORGANISM: Mus musculus

<400> SEQUENCE: 59

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
```

```
                    20                  25                  30
Val Ser Leu Gly Gln Ser Val Thr Ile Ser Cys Arg Ala Ser Glu Ser
                35                  40                  45
Val Glu Tyr Tyr Gly Thr Ser Leu Met Gln Trp Tyr Gln Gln Lys Pro
            50                  55                  60
Gly Gln Pro Pro Lys Leu Leu Ile Tyr Gly Ala Ser Asp Val Glu Ser
65                  70                  75                  80
Gly Val Pro Ala Arg Phe Ser Gly Ser Gly Ser Gly Thr Asp Phe Ser
                85                  90                  95
Leu Asn Ile His Pro Val Glu Glu Asp Asp Ile Ala Met Tyr Phe Cys
            100                 105                 110
Gln Gln Ser Arg Lys Val Pro Tyr Thr Phe Gly Ser Gly Thr Lys Leu
            115                 120                 125
Glu Ile Lys Arg Ala Asp Ala Ala Pro Thr Val Ser Ile Phe Pro Pro
        130                 135                 140
Ser Ser Glu Gln Leu Thr Ser Gly Gly Ala Ser Val Val Cys Phe Leu
145                 150                 155                 160
Asn Asn Phe Tyr Pro Lys Asp Ile Asn Val Lys Trp Lys Ile Asp Gly
                165                 170                 175
Ser Glu Arg Gln Asn Gly Val Leu Asn Ser Trp Thr Asp Gln Asp Ser
            180                 185                 190
Lys Asp Ser Thr Tyr Ser Met Ser Ser Thr Leu Thr Leu Thr Lys Asp
            195                 200                 205
Glu Tyr Glu Arg His Asn Ser Tyr Thr Cys Glu Ala Thr His Lys Thr
        210                 215                 220
Ser Thr Ser Pro Ile Val Lys Ser Phe Asn Arg Asn Glu Cys
225                 230                 235

<210> SEQ ID NO 60
<211> LENGTH: 1401
<212> TYPE: DNA
<213> ORGANISM: Mus musculus

<400> SEQUENCE: 60
atggaatcta actggatact tccttttatt ctgtcggtaa cttcaggggt ctactcagag       60
gttcagctcc agcagtctgg gactgtgctg gcaaggcctg ggcttcagt gaagatgtcc      120 tgcaaggctt ctggctacac ctttgccagc tactggattc actgggtaaa gcagaggcct     180
ggacagggtc tggaatggat tggctctatt tatcctggaa atagtgatac tacctacaac     240
cagaagttca gggcaaggc caaactgact gtagtcacat ctgccagctc tgcctacatg      300
gagctcagca gcctgacaaa tgaggactct gcggtctatt actgtacaga acctacttac    360
tatagttacg acgattacta tgctatggac tattggggtc aaggaacctc agtcaccgtc    420
tcctcagcca aaacgacacc cccatctgtc tatccactgg cccctggatc tgctgcccaa    480
actaactcca tggtgaccct gggatgcctg gtcaagggct atttccctga gccagtgaca    540
gtgacctgga actctggatc cctgtccagc ggtgtgcaca ccttcccagc tgtcctgcag    600
tctgacctct acactctgag cagctcagtg actgtcccct ccagcacctg gcccagccag    660
accgtcacct gcaacgttgc cacccggcc agcagcacca aggtggacaa gaaaattgtg    720
cccagggatt gtggttgtaa gccttgcata tgtacagtcc agaagtatc atctgtcttc    780 atcttccccc caaagcccaa ggatgtgctc accattactc tgactcctaa ggtcacgtgt    840
gttgtggtag acatcagcaa ggatgatccc gaggtccagt tcagctggtt tgtagatgat    900
```

-continued

```
gtggaggtgc acacagctca gacaaaaccc cgggaggagc agttcaacag cactttccgt    960
tcagtcagtg aacttcccat catgcaccag gactggctca atggcaagga gttcaaatgc   1020
agggtcaaca gtgcagcttt ccctgccccc atcgagaaaa ccatctccaa aaccaaaggc   1080
agaccgaagg ctccacaggt gtacaccatt ccacctccca aggagcagat ggccaaggat   1140
aaagtcagtc tgacctgcat gataacagac ttcttccctg aagacattac tgtggagtgg   1200
cagtggaatg ggcagccagc ggagaactac aagaacactc agcccatcat ggacacagat   1260
ggctcttact tcgtctacag caagctcaat gtgcagaaga gcaactggga ggcaggaaat   1320
actttcacct gctctgtgtt acatgagggc ctgcacaacc accatactga aagagcctc   1380 tcccactctc ctggtaaatg a                                             1401
```

<210> SEQ ID NO 61
<211> LENGTH: 466
<212> TYPE: PRT
<213> ORGANISM: Mus musculus

<400> SEQUENCE: 61

```
Met Glu Ser Asn Trp Ile Leu Pro Phe Ile Leu Ser Val Thr Ser Gly
1               5                   10                  15

Val Tyr Ser Glu Val Gln Leu Gln Gln Ser Gly Thr Val Leu Ala Arg
            20                  25                  30

Pro Gly Ala Ser Val Lys Met Ser Cys Lys Ala Ser Gly Tyr Thr Phe
        35                  40                  45

Ala Ser Tyr Trp Ile His Trp Val Lys Gln Arg Pro Gly Gln Gly Leu
    50                  55                  60

Glu Trp Ile Gly Ser Ile Tyr Pro Gly Asn Ser Asp Thr Thr Tyr Asn
65                  70                  75                  80

Gln Lys Phe Lys Gly Lys Ala Lys Leu Thr Val Thr Ser Ala Ser
                85                  90                  95

Ser Ala Tyr Met Glu Leu Ser Ser Leu Thr Asn Glu Asp Ser Ala Val
            100                 105                 110

Tyr Tyr Cys Thr Glu Pro Thr Tyr Tyr Ser Tyr Asp Asp Tyr Tyr Ala
        115                 120                 125

Met Asp Tyr Trp Gly Gln Gly Thr Ser Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Gln Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285
```

```
Asp Pro Glu Val Gln Phe Ser Trp Phe Val Asp Asp Val Glu Val His
        290                 295                 300

Thr Ala Gln Thr Lys Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
        370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Val Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465

<210> SEQ ID NO 62
<211> LENGTH: 714
<212> TYPE: DNA
<213> ORGANISM: Mus musculus

<400> SEQUENCE: 62
atggattttc atgtgcagat tttcagcttc atgctaatca gtgtcacagt catattgtcc      60
agtggagaaa ttgtgctcac ccagtctcca gcactcatgg ctgcatctcc aggggagaag    120
gtcaccatca cctgcagtgt cagctcaagt ataagttcca gcaacttaca ctggtaccag    180
cagaagtcag gaacctcccc caaaccctgg atttatggca catccaacct tgcttctgga    240
gtccctgttc gcttcagtgg cagtggatct gggacctctt attctctcac aatcagcacc    300
atggaggctg aagatgctgc cacttattac tgtcaacagt ggagtagtta cccgctcacg    360
ttcggtgctg ggaccaagct ggagctgaaa cgggctgatg ctgcaccaac tgtatccatc    420
ttcccaccat ccagtgagca gttaacatct ggaggtgcct cagtcgtgtg cttcttgaac    480
aacttctacc ccaaagacat caatgtcaag tggaagattg atggcagtga acgacaaaat    540
ggcgtcctga acagttggac tgatcaggac agcaaagaca gcacctacag catgagcagc    600
accctcacgt tgaccaagga cgagtatgaa cgacataaca gctatacctg tgaggccact    660
cacaagacat caacttcacc cattgtcaag agcttcaaca ggaatgagtg ttag          714

<210> SEQ ID NO 63
<211> LENGTH: 237
<212> TYPE: PRT
<213> ORGANISM: Mus musculus

<400> SEQUENCE: 63

Met Asp Phe His Val Gln Ile Phe Ser Phe Met Leu Ile Ser Val Thr
1               5                   10                  15
```

Val Ile Leu Ser Ser Gly Glu Ile Val Leu Thr Gln Ser Pro Ala Leu
            20                  25                  30

Met Ala Ala Ser Pro Gly Glu Lys Val Thr Ile Thr Cys Ser Val Ser
            35                  40                  45

Ser Ser Ile Ser Ser Ser Asn Leu His Trp Tyr Gln Gln Lys Ser Gly
50                  55                  60

Thr Ser Pro Lys Pro Trp Ile Tyr Gly Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Thr Met Glu Ala Glu Asp Ala Ala Thr Tyr Tyr Cys Gln
            100                 105                 110

Gln Trp Ser Ser Tyr Pro Leu Thr Phe Gly Ala Gly Thr Lys Leu Glu
            115                 120                 125

Leu Lys Arg Ala Asp Ala Ala Pro Thr Val Ser Ile Phe Pro Pro Ser
130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
            195                 200                 205

Tyr Glu Arg His Asn Ser Tyr Thr Cys Glu Ala Thr His Lys Thr Ser
        210                 215                 220

Thr Ser Pro Ile Val Lys Ser Phe Asn Arg Asn Glu Cys
225                 230                 235

<210> SEQ ID NO 64
<211> LENGTH: 1389
<212> TYPE: DNA
<213> ORGANISM: Artificial Sequence
<220> FEATURE:
<223> OTHER INFORMATION: Synthetic nucleotide sequence

<400> SEQUENCE: 64
atgggatgga actggatctt tattttaatc ctgtcagtaa ctacaggtgt ccactctgag     60
gtccagctgc agcagtctgg acctgagctg gtgaagcctg gggcttcagt gaagatatcc    120
tgcaaggctt ctggttactc attcactgcc tactacatgc actgggtgaa gcaaagtcct    180
gaaaagtgcc ttgagtggat tggacagatt aatcctagca ctggtggtac tacctacaac    240
cagaagttca aggccaaggc cacattgact gtagacaaat cctccagcac agcctacatg    300
cagctcaaga gcctgacatc tgaggactct gcagtctatt attgtgcaag atgggtgac    360 tcttggggcc aaggcaccac tctcacagtc tcctcagcta gcaccaaggg cccatcggtc    420
ttccccctgg caccctcctc caagagcacc tctggggca gcggccct gggctgcctg    480 gtcaaggact acttccccga accggtgacg gtgtcgtgga actcaggcgc cctgaccagc    540
ggcgtgcaca ccttcccggc tgtcctacag tcctcaggac tctactccct cagcagcgtg    600
gtgaccgtgc cctccagcag cttgggcacc cagacctaca tctgcaacgt gaatcacaag    660
cccagcaaca ccaaggtgga caagaaagtt gagcccaaat cttgtgacaa aactcacaca    720
tgcccaccgt gcccagcacc tgaactcctg ggggaccgt cagtcttcct cttcccccca    780

```
aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaaagggca gccccgagaa   1080
ccacaggtgt acaccctgcc cccatcccgg gatgagctga ccaagaacca ggtcagcctg   1140
acctgcctgg tcaaaggctt ctatcccagc gacatcgccg tggagtggga gagcaatggg   1200
cagccggaga acaactacaa gaccacgcct cccgtgctgg actccgacgg ctccttcttc   1260
ctctacagca agctcaccgt ggacaagagc aggtggcagc aggggaacgt cttctcatgc   1320
tccgtgatgc atgaggctct gcacaaccac tacacgcaga agagcctctc cctgtctccg   1380
ggtaaatga                                                           1389
```

<210> SEQ ID NO 65
<211> LENGTH: 462
<212> TYPE: PRT
<213> ORGANISM: Artificial Sequence
<220> FEATURE:
<223> OTHER INFORMATION: Synthetic peptide sequence

<400> SEQUENCE: 65

```
Met Gly Trp Asn Trp Ile Phe Ile Leu Ile Leu Ser Val Thr Thr Gly
1               5                   10                  15

Val His Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

Thr Ala Tyr Tyr Met His Trp Val Lys Gln Ser Pro Glu Lys Cys Leu
    50                  55                  60

Glu Trp Ile Gly Gln Ile Asn Pro Ser Thr Gly Gly Thr Thr Tyr Asn
65                  70                  75                  80

Gln Lys Phe Lys Ala Lys Ala Thr Leu Thr Val Asp Lys Ser Ser Ser
                85                  90                  95

Thr Ala Tyr Met Gln Leu Lys Ser Leu Thr Ser Glu Asp Ser Ala Val
            100                 105                 110

Tyr Tyr Cys Ala Arg Trp Gly Asp Ser Trp Gly Gln Gly Thr Thr Leu
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255
```

-continued

Leu Phe Pro Pro Lys Pro Lys Asp Thr Leu Met Ile Ser Arg Thr Pro
              260                 265                 270

Glu Val Thr Cys Val Val Val Asp Val Ser His Glu Asp Pro Glu Val
          275                 280                 285

Lys Phe Asn Trp Tyr Val Asp Gly Val Glu Val His Asn Ala Lys Thr
      290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
              325                 330                 335

Lys Val Ser Asn Lys Ala Leu Pro Ala Pro Ile Glu Lys Thr Ile Ser
          340                 345                 350

Lys Ala Lys Gly Gln Pro Arg Glu Pro Gln Val Tyr Thr Leu Pro Pro
      355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
              405                 410                 415

Gly Ser Phe Phe Leu Tyr Ser Lys Leu Thr Val Asp Lys Ser Arg Trp
          420                 425                 430

Gln Gln Gly Asn Val Phe Ser Cys Ser Val Met His Glu Ala Leu His
      435                 440                 445

Asn His Tyr Thr Gln Lys Ser Leu Ser Leu Ser Pro Gly Lys
          450                 455                 460

<210> SEQ ID NO 66
<211> LENGTH: 717
<212> TYPE: DNA
<213> ORGANISM: Artificial Sequence
<220> FEATURE:
<223> OTHER INFORMATION: Synthetic nucleotide sequence

<400> SEQUENCE: 66
atggagacag acacactcct gctatgggtg ctgctgctct gggttccagg ctccactggt      60
gacattgtgc tcacccaatc tccagcttct ttggctgtgt ctctaggca gagtgtcacc     120 atctcctgca gagccagtga agtgttgaa tattatggca ctagtttaat gcagtggtac     180
caacagaaac caggacagcc acccaaactc ctcatctatg gtgcatccga cgtagaatct     240
ggggtccctg ccaggtttag tggcagtggg tctgggacag acttcagcct caacatccat     300
cctgtggagg aggatgatat tgcaatgtat ttctgtcagc aaagtaggaa ggttccgtat     360
acgttcggat cggggaccaa gttggaaata aaacgtacgg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta gcctcagc     600 agcaccctga cgctgagcaa agcagactac gagaaacaca agtctacgc ctgcgaagtc     660 acccatcagg gcctgagctc gcccgtcaca aagagcttca caggggaga gtgttga       717

<210> SEQ ID NO 67
<211> LENGTH: 238
<212> TYPE: PRT
<213> ORGANISM: Artificial Sequence
<220> FEATURE:
<223> OTHER INFORMATION: Synthetic peptide sequence

<400> SEQUENCE: 67

```
Met Glu Thr Asp Thr Leu Leu Leu Trp Val Leu Leu Leu Trp Val Pro
1               5                   10                  15
Gly Ser Thr Gly Asp Ile Val Leu Thr Gln Ser Pro Ala Ser Leu Ala
            20                  25                  30
Val Ser Leu Gly Gln Ser Val Thr Ile Ser Cys Arg Ala Ser Glu Ser
        35                  40                  45
Val Glu Tyr Tyr Gly Thr Ser Leu Met Gln Trp Tyr Gln Gln Lys Pro
    50                  55                  60
Gly Gln Pro Pro Lys Leu Leu Ile Tyr Gly Ala Ser Asp Val Glu Ser
65                  70                  75                  80
Gly Val Pro Ala Arg Phe Ser Gly Ser Gly Ser Gly Thr Asp Phe Ser
                85                  90                  95
Leu Asn Ile His Pro Val Glu Glu Asp Asp Ile Ala Met Tyr Phe Cys
            100                 105                 110
Gln Gln Ser Arg Lys Val Pro Tyr Thr Phe Gly Ser Gly Thr Lys Leu
        115                 120                 125
Glu Ile Lys Arg Thr Val Ala Ala Pro Ser Val Phe Ile Phe Pro Pro
    130                 135                 140
Ser Asp Glu Gln Leu Lys Ser Gly Thr Ala Ser Val Val Cys Leu Leu
145                 150                 155                 160
Asn Asn Phe Tyr Pro Arg Glu Ala Lys Val Gln Trp Lys Val Asp Asn
                165                 170                 175
Ala Leu Gln Ser Gly Asn Ser Gln Glu Ser Val Thr Glu Gln Asp Ser
            180                 185                 190
Lys Asp Ser Thr Tyr Ser Leu Ser Ser Thr Leu Thr Leu Ser Lys Ala
        195                 200                 205
Asp Tyr Glu Lys His Lys Val Tyr Ala Cys Glu Val Thr His Gln Gly
    210                 215                 220
Leu Ser Ser Pro Val Thr Lys Ser Phe Asn Arg Gly Glu Cys
225                 230                 235
```

<210> SEQ ID NO 68
<211> LENGTH: 1419
<212> TYPE: DNA
<213> ORGANISM: Artificial Sequence
<220> FEATURE:
<223> OTHER INFORMATION: Synthetic nucleotide sequence

<400> SEQUENCE: 68

| | | | | | | |
|---|---|---|---|---|---|---|
| atggaatcta | actggatact | tccttttatt | ctgtcggtaa | cttcagggt | ctactcagag | 60 |
| gttcagctcc | agcagtctgg | gactgtgctg | gcaaggcctg | gggcttcagt | gaagatgtcc | 120 |
| tgcaaggctt | ctggctacac | ctttgccagc | tactggattc | actgggtaaa | gcagaggcct | 180 |
| ggacagggtc | tggaatggat | tggctctatt | tatcctggaa | atagtgatac | tacctacaac | 240 |
| cagaagttca | aggcaaggc | caaactgact | gtagtcacat | ctgccagctc | tgcctacatg | 300 |
| gagctcagca | gcctgacaaa | tgaggactct | gcggtctatt | actgtacaga | acctacttac | 360 |
| tatagttacg | acgattacta | tgctatggac | tattggggtc | aaggaacctc | agtcaccgtc | 420 |
| tcctcagcta | gcaccaaggg | cccatcggtc | ttccccctgg | caccctcctc | caagagcacc | 480 |
| tctgggggca | cagcggccct | gggctgcctg | gtcaaggact | acttccccga | accggtgacg | 540 |
| gtgtcgtgga | actcaggcgc | cctgaccagc | ggcgtgcaca | ccttcccggc | tgtcctacag | 600 |

```
tcctcaggac tctactccct cagcagcgtg gtgaccgtgc cctccagcag cttgggcacc    660
cagacctaca tctgcaacgt gaatcacaag cccagcaaca ccaaggtgga caagaaagtt    720
gagcccaaat cttgtgacaa aactcacaca tgcccaccgt gcccagcacc tgaactcctg    780
gggggaccgt cagtcttcct cttccccccaaaacccaagg acaccctcat gatctcccgg     840 accctgagg tcacatgcgt ggtggtggac gtgagccacg aagaccctga ggtcaagttc     900
aactggtacg tggacggcgt ggaggtgcat aatgccaaga caaagccgcg ggaggagcag    960
tacaacagca cgtaccgtgt ggtcagcgtc ctcaccgtcc tgcaccagga ctggctgaat    1020
ggcaaggagt acaagtgcaa ggtctccaac aaagcccctcc cagcccccat cgagaaaacc   1080
atctccaaag ccaaagggca gccccgagaa ccacaggtgt acaccctgcc cccatcccgg    1140
gatgagctga ccaagaacca ggtcagcctg acctgcctgg tcaaaggctt ctatcccagc    1200
gacatcgccg tggagtggga gagcaatggg cagccggaga caactacaa gaccacgcct     1260 cccgtgctgg actccgacgg ctccttcttc ctctacagca agctcaccgt ggacaagagc    1320
aggtggcagc aggggaacgt cttctcatgc tccgtgatgc atgaggctct gcacaaccac    1380
tacacgcaga gagcctctc cctgtctccg ggtaaatga                            1419
```

<210> SEQ ID NO 69
<211> LENGTH: 472
<212> TYPE: PRT
<213> ORGANISM: Artificial Sequence
<220> FEATURE:
<223> OTHER INFORMATION: Synthetic peptide sequence

<400> SEQUENCE: 69

```
Met Glu Ser Asn Trp Ile Leu Pro Phe Ile Leu Ser Val Thr Ser Gly
1               5                   10                  15

Val Tyr Ser Glu Val Gln Leu Gln Gln Ser Gly Thr Val Leu Ala Arg
            20                  25                  30

Pro Gly Ala Ser Val Lys Met Ser Cys Lys Ala Ser Gly Tyr Thr Phe
        35                  40                  45

Ala Ser Tyr Trp Ile His Trp Val Lys Gln Arg Pro Gly Gln Gly Leu
    50                  55                  60

Glu Trp Ile Gly Ser Ile Tyr Pro Gly Asn Ser Asp Thr Thr Tyr Asn
65                  70                  75                  80

Gln Lys Phe Lys Gly Lys Ala Lys Leu Thr Val Val Thr Ser Ala Ser
                85                  90                  95

Ser Ala Tyr Met Glu Leu Ser Ser Leu Thr Asn Glu Asp Ser Ala Val
            100                 105                 110

Tyr Tyr Cys Thr Glu Pro Thr Tyr Tyr Ser Tyr Asp Asp Tyr Ala
        115                 120                 125

Met Asp Tyr Trp Gly Gln Gly Thr Ser Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
```

Cys Asn Val Asn His Lys Pro Ser Asn Thr Lys Val Asp Lys Val
225                 230                 235                 240

Glu Pro Lys Ser Cys Asp Lys Thr His Thr Cys Pro Pro Cys Pro Ala
            245                 250                 255

Pro Glu Leu Leu Gly Gly Pro Ser Val Phe Leu Phe Pro Pro Lys Pro
        260                 265                 270

Lys Asp Thr Leu Met Ile Ser Arg Thr Pro Glu Val Thr Cys Val Val
    275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
            325                 330                 335

Asp Trp Leu Asn Gly Lys Glu Tyr Lys Cys Lys Val Ser Asn Lys Ala
        340                 345                 350

Leu Pro Ala Pro Ile Glu Lys Thr Ile Ser Lys Ala Lys Gly Gln Pro
    355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Pro Pro Val Leu Asp Ser Asp Gly Ser Phe Phe Leu Tyr
        420                 425                 430

Ser Lys Leu Thr Val Asp Lys Ser Arg Trp Gln Gln Gly Asn Val Phe
    435                 440                 445

Ser Cys Ser Val Met His Glu Ala Leu His Asn His Tyr Thr Gln Lys
450                 455                 460

Ser Leu Ser Leu Ser Pro Gly Lys
465                 470

<210> SEQ ID NO 70
<211> LENGTH: 714
<212> TYPE: DNA
<213> ORGANISM: Artificial Sequence
<220> FEATURE:
<223> OTHER INFORMATION: Synthetic nucleotide sequence

<400> SEQUENCE: 70
atggattttc atgtgcagat tttcagcttc atgctaatca gtgtcacagt catattgtcc     60
agtggagaaa ttgtgctcac ccagtctcca gcactcatgg ctgcatctcc aggggagaag    120
gtcaccatca cctgcagtgt cagctcaagt ataagttcca gcaacttaca ctggtaccag    180
cagaagtcag gaacctcccc caaaccctgg atttatggca catccaacct tgcttctgga    240
gtccctgttc gcttcagtgg cagtggatct gggacctctt attctctcac aatcagcacc    300
atggaggctg aagatgctgc cacttattac tgtcaacagt ggagtagtta cccgctcacg    360
ttcggtgctg ggaccaagct ggagctgaaa cgtacggtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg ttga          714

<210> SEQ ID NO 71
<211> LENGTH: 237
<212> TYPE: PRT
<213> ORGANISM: Artificial Sequence
<220> FEATURE:
<223> OTHER INFORMATION: Synthetic peptide sequence

<400> SEQUENCE: 71

Met Asp Phe His Val Gln Ile Phe Ser Phe Met Leu Ile Ser Val Thr
1               5                   10                  15

Val Ile Leu Ser Ser Gly Glu Ile Val Leu Thr Gln Ser Pro Ala Leu
            20                  25                  30

Met Ala Ala Ser Pro Gly Glu Lys Val Thr Ile Thr Cys Ser Val Ser
        35                  40                  45

Ser Ser Ile Ser Ser Ser Asn Leu His Trp Tyr Gln Gln Lys Ser Gly
    50                  55                  60

Thr Ser Pro Lys Pro Trp Ile Tyr Gly Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Thr Met Glu Ala Glu Asp Ala Ala Thr Tyr Tyr Cys Gln
            100                 105                 110

Gln Trp Ser Ser Tyr Pro Leu Thr Phe Gly Ala Gly Thr Lys Leu Glu
        115                 120                 125

Leu Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 72
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 72

Gly Gly Gly Ser
1

<210> SEQ ID NO 73
<211> LENGTH: 4
<212> TYPE: PRT
<213> ORGANISM: Artificial Sequence
<220> FEATURE:

```
<223> OTHER INFORMATION: Synthetic peptide sequence

<400> SEQUENCE: 73

Ser Gly Gly Gly
1

<210> SEQ ID NO 74
<211> LENGTH: 5
<212> TYPE: PRT
<213> ORGANISM: Artificial Sequence
<220> FEATURE:
<223> OTHER INFORMATION: An artificially synthesized peptide sequence

<400> SEQUENCE: 74

Gly Gly Gly Gly Ser
1               5

<210> SEQ ID NO 75
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 75

Ser Gly Gly Gly Gly
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 76

Gly Gly Gly Gly Gly Ser
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 77

Ser Gly Gly Gly Gly Gly
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 78

Gly Gly Gly Gly Gly Gly Ser
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic peptide sequence
```

<400> SEQUENCE: 79

Ser Gly Gly Gly Gly Gly
1               5

<210> SEQ ID NO 80
<211> LENGTH: 15
<212> TYPE: DNA
<213> ORGANISM: Mus musculus

<400> SEQUENCE: 80
gactacaaca tggac                                                       15

<210> SEQ ID NO 81
<211> LENGTH: 5
<212> TYPE: PRT
<213> ORGANISM: Mus musculus

<400> SEQUENCE: 81

Asp Tyr Asn Met Asp
1               5

<210> SEQ ID NO 82
<211> LENGTH: 51
<212> TYPE: DNA
<213> ORGANISM: Mus musculus

<400> SEQUENCE: 82
tatatttatc ctaacaatgg tggttctggc tacaaccaga agttcaagag c                51

<210> SEQ ID NO 83
<211> LENGTH: 17
<212> TYPE: PRT
<213> ORGANISM: Mus musculus

<400> SEQUENCE: 83

Tyr Ile Tyr Pro Asn Asn Gly Gly Ser Gly Tyr Asn Gln Lys Phe Lys
1               5                   10                  15

Ser

<210> SEQ ID NO 84
<211> LENGTH: 42
<212> TYPE: DNA
<213> ORGANISM: Mus musculus

<400> SEQUENCE: 84
cgggatagtt actatggttt cgacatggcc tggtttgctt ac                         42

<210> SEQ ID NO 85
<211> LENGTH: 14
<212> TYPE: PRT
<213> ORGANISM: Mus musculus

<400> SEQUENCE: 85

Arg Asp Ser Tyr Tyr Gly Phe Asp Met Ala Trp Phe Ala Tyr
1               5                   10

<210> SEQ ID NO 86
<211> LENGTH: 33
<212> TYPE: DNA
<213> ORGANISM: Mus musculus

<400> SEQUENCE: 86
cgaccaagtg agaatattta caataattta gca        33

<210> SEQ ID NO 87
<211> LENGTH: 11
<212> TYPE: PRT
<213> ORGANISM: Mus musculus

<400> SEQUENCE: 87

Arg Pro Ser Glu Asn Ile Tyr Asn Asn Leu Ala
1               5                   10

<210> SEQ ID NO 88
<211> LENGTH: 21
<212> TYPE: DNA
<213> ORGANISM: Mus musculus

<400> SEQUENCE: 88
gttgcaacaa atttagcaga a        21

<210> SEQ ID NO 89
<211> LENGTH: 7
<212> TYPE: PRT
<213> ORGANISM: Mus musculus

<400> SEQUENCE: 89

Val Ala Thr Asn Leu Ala Glu
1               5

<210> SEQ ID NO 90
<211> LENGTH: 27
<212> TYPE: DNA
<213> ORGANISM: Mus musculus

<400> SEQUENCE: 90
caacattctt atggtactcc gtggacg        27

<210> SEQ ID NO 91
<211> LENGTH: 9
<212> TYPE: PRT
<213> ORGANISM: Mus musculus

<400> SEQUENCE: 91

Gln His Ser Tyr Gly Thr Pro Trp Thr
1               5

<210> SEQ ID NO 92
<211> LENGTH: 426
<212> TYPE: DNA
<213> ORGANISM: Mus musculus

<400> SEQUENCE: 92
atgggatgga actggatctt tctcttcctc ctgtcaggaa ctgcaggtgt cctctctgag        60
gtccagctgc agcagtctgg acctgaactg gtgaagcctg gggcttcagt gaagatatcc       120
tgcaaggctt ctggatacac attcactgac tacaacatgg actgggtgaa gcagagccat       180
ggagagagcc ttagtggat tggatatatt tatcctaaca atggtggttc tggctacaac       240
cagaagttca gagcaaggc cacattgact gtagacaagt cctccagcac agcctacatg       300
gagctccaca gcctgacatc tgaagactct gcagtctatt actgtgcaag acgggatagt       360
tactatggtt tcgacatggc ctggtttgct tactggggcc aagggactct ggtcactgtc       420
tctgca       426

<210> SEQ ID NO 93
<211> LENGTH: 142
<212> TYPE: PRT
<213> ORGANISM: Mus musculus

<400> SEQUENCE: 93

Met Gly Trp Asn Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Glu Ser Leu
    50                  55                  60

Glu Trp Ile Gly Tyr Ile Tyr Pro Asn Asn Gly Gly Ser Gly Tyr Asn
65                  70                  75                  80

Gln Lys Phe Lys Ser Lys Ala Thr Leu Thr Val Asp Lys Ser Ser Ser
                85                  90                  95

Thr Ala Tyr Met Glu Leu His Ser Leu Thr Ser Glu Asp Ser Ala Val
            100                 105                 110

Tyr Tyr Cys Ala Arg Arg Asp Ser Tyr Tyr Gly Phe Asp Met Ala Trp
        115                 120                 125

Phe Ala Tyr Trp Gly Gln Gly Thr Leu Val Thr Val Ser Ala
    130                 135                 140

<210> SEQ ID NO 94
<211> LENGTH: 381
<212> TYPE: DNA
<213> ORGANISM: Mus musculus

<400> SEQUENCE: 94
atgagtgtgc ccactcaggt cctggggttg ctgctgctgt ggcttacagg tgccagatgt      60
gacatccaga tgactcagtc tccagcctcc ctatctgcat ctgtgggaga aactgtcacc     120
atcacatgtc gaccaagtga gaatatttac aataatttag catggtatca acagaaacag     180
ggaaaatctc ctcagctcct ggtctatgtt gcaacaaatt tagcagaagg tgtgccatca     240
aggttcagtg gcagtggatc aggcacacgg ttttctctga agatcaacag cctgcagcct     300
gaagattttg ggagttatta ctgtcaacat tcttatggta ctccgtggac gttcggtgga     360
ggcaccaagc tggagatcaa a                                               381

<210> SEQ ID NO 95
<211> LENGTH: 127
<212> TYPE: PRT
<213> ORGANISM: Mus musculus

<400> SEQUENCE: 95

Met Ser Val Pro Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Pro Ser Glu Asn
        35                  40                  45

Ile Tyr Asn Asn Leu Ala Trp Tyr Gln Gln Lys Gln Gly Lys Ser Pro
    50                  55                  60

Gln Leu Leu Val Tyr Val Ala Thr Asn Leu Ala Glu Gly Val Pro Ser
65                  70                  75                  80

Arg Phe Ser Gly Ser Gly Ser Gly Thr Arg Phe Ser Leu Lys Ile Asn
                85                  90                  95

Ser Leu Gln Pro Glu Asp Phe Gly Lys Tyr Tyr Cys Gln His Ser Tyr
            100                 105                 110

Gly Thr Pro Trp Thr Phe Gly Gly Gly Thr Lys Leu Glu Ile Lys
        115                 120                 125

<210> SEQ ID NO 96
<211> LENGTH: 1416
<212> TYPE: DNA
<213> ORGANISM: Artificial Sequence
<220> FEATURE:
<223> OTHER INFORMATION: Synthetic nucleotide sequence

<400> SEQUENCE: 96

```
atgggatgga actggatctt tctcttcctc ctgtcaggaa ctgcaggtgt cctctctgag      60
gtccagctgc agcagtctgg acctgaactg gtgaagcctg ggcttcagt gaagatatcc      120
tgcaaggctt ctggatacac attcactgac tacaacatgg actgggtgaa gcagagccat     180
ggagagagcc ttagtggat tggatatatt tatcctaaca atggtggttc tggctacaac      240
cagaagttca agagcaaggc cacattgact gtagacaagt cctccagcac agcctacatg     300
gagctccaca gcctgacatc tgaagactct gcagtctatt actgtgcaag acgggatagt     360
tactatggtt tcgacatggc ctggtttgct tactggggcc aagggactct ggtcactgtc     420
tctgcagcta gcaccaaggg cccatcggtc ttccccctgg caccctcctc caagagcacc     480
tctgggggca gcggccct gggctgcctg gtcaaggact acttccccga accggtgacg       540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacc    660
cagacctaca tctgcaacgt gaatcacaag cccagcaaca ccaaggtgga caagaaagtt   720
gagcccaaat cttgtgacaa aactcacaca tgcccaccgt gcccagcacc tgaactcctg   780
gggggaccgt cagtcttcct cttccccca aaacccaagg acaccctcat gatctcccgg    840
accctgagg tcacatgcgt ggtggtggac gtgagccacg aagaccctga ggtcaagttc    900
aactggtacg tggacggcgt ggaggtgcat aatgccaaga caaagccgcg ggaggagcag   960
tacaacagca cgtaccgtgt ggtcagcgtc ctcaccgtcc tgcaccagga ctggctgaat  1020
ggcaaggagt acaagtgcaa ggtctccaac aaagccctcc cagcccccat cgagaaaacc   1080
atctccaaag ccaaagggca gccccgagaa ccacaggtgt acaccctgcc cccatcccgg   1140
gatgagctga ccaagaacca ggtcagcctg acctgcctgg tcaaaggctt ctatcccagc   1200
gacatcgccg tggagtggga gagcaatggg cagccggaga acaactacaa gaccacgcct   1260
cccgtgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaa                              1416
```

<210> SEQ ID NO 97
<211> LENGTH: 472
<212> TYPE: PRT
<213> ORGANISM: Artificial Sequence
<220> FEATURE:
<223> OTHER INFORMATION: Synthetic peptide sequence

<400> SEQUENCE: 97

Met Gly Trp Asn Trp Ile Phe Leu Phe Leu Leu Ser Gly Thr Ala Gly

-continued

```
1               5                   10                  15
Val Leu Ser Glu Val Gln Leu Gln Gln Ser Gly Pro Glu Leu Val Lys
            20                  25                  30
Pro Gly Ala Ser Val Lys Ile Ser Cys Lys Ala Ser Gly Tyr Thr Phe
            35                  40                  45
Thr Asp Tyr Asn Met Asp Trp Val Lys Gln Ser His Gly Glu Ser Leu
        50                  55                  60
Glu Trp Ile Gly Ile Tyr Pro Asn Gly Gly Ser Gly Tyr Asn
65                  70                  75                  80
Gln Lys Phe Lys Ser Lys Ala Thr Leu Thr Val Asp Lys Ser Ser Ser
                85                  90                  95
Thr Ala Tyr Met Glu Leu His Ser Leu Thr Ser Glu Asp Ser Ala Val
                100                 105                 110
Tyr Tyr Cys Ala Arg Arg Asp Ser Tyr Tyr Gly Phe Asp Met Ala Trp
                115                 120                 125
Phe Ala Tyr Trp Gly Gln Gly Thr Leu Val Thr Val Ser Ala Ala Ser
            130                 135                 140
Thr Lys Gly Pro Ser Val Phe Pro Leu Ala Pro Ser Ser Lys Ser Thr
145                 150                 155                 160
Ser Gly Gly Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
                180                 185                 190
His Thr Phe Pro Ala Val Leu Gln Ser Ser Gly Leu Tyr Ser Leu Ser
                195                 200                 205
Ser Val Val Thr Val Pro Ser Ser Ser Leu Gly Thr Gln Thr Tyr Ile
    210                 215                 220
Cys Asn Val Asn His Lys Pro Ser Asn Thr Lys Val Asp Lys Lys Val
225                 230                 235                 240
Glu Pro Lys Ser Cys Asp Lys Thr His Thr Cys Pro Pro Cys Pro Ala
                245                 250                 255
Pro Glu Leu Leu Gly Gly Pro Ser Val Phe Leu Phe Pro Pro Lys Pro
                260                 265                 270
Lys Asp Thr Leu Met Ile Ser Arg Thr Pro Glu Val Thr Cys Val Val
                275                 280                 285
Val Asp Val Ser His Glu Asp Pro Glu Val Lys Phe Asn Trp Tyr Val
                290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
                340                 345                 350
Leu Pro Ala Pro Ile Glu Lys Thr Ile Ser Lys Ala Lys Gly Gln Pro
                355                 360                 365
Arg Glu Pro Gln Val Tyr Thr Leu Pro Pro Ser Arg Asp Glu Leu Thr
                370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
                420                 425                 430
```

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 98
<211> LENGTH: 702
<212> TYPE: DNA
<213> ORGANISM: Artificial Sequence
<220> FEATURE:
<223> OTHER INFORMATION: Synthetic nucleotide sequence

<400> SEQUENCE: 98
atgagtgtgc ccactcaggt cctggggttg ctgctgctgt ggcttacagg tgccagatgt      60
gacatccaga tgactcagtc tccagcctcc ctatctgcat ctgtgggaga aactgtcacc     120
atcacatgtc gaccaagtga gaatatttac aataatttag catggtatca acagaaacag     180
ggaaaatctc ctcagctcct ggtctatgtt gcaacaaatt tagcagaagg tgtgccatca     240
aggttcagtg gcagtggatc aggcacacgg ttttctctga gatcaacagc ctgcagcct     300 gaagattttg ggagtatta ctgtcaacat tcttatggta ctccgtggac gttcggtgga     360
ggcaccaagc tggagatcaa acgtacggtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac aggggagagt gt                        702

<210> SEQ ID NO 99
<211> LENGTH: 234
<212> TYPE: PRT
<213> ORGANISM: Artificial Sequence
<220> FEATURE:
<223> OTHER INFORMATION: Synthetic peptide sequence

<400> SEQUENCE: 99

Met Ser Val Pro Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Pro Ser Glu Asn
        35                  40                  45

Ile Tyr Asn Asn Leu Ala Trp Tyr Gln Gln Lys Gln Gly Lys Ser Pro
    50                  55                  60

Gln Leu Leu Val Tyr Val Ala Thr Asn Leu Ala Glu Gly Val Pro Ser
65                  70                  75                  80

Arg Phe Ser Gly Ser Gly Ser Gly Thr Arg Phe Ser Leu Lys Ile Asn
                85                  90                  95

Ser Leu Gln Pro Glu Asp Phe Gly Lys Tyr Tyr Cys Gln His Ser Tyr
                100                 105                 110

Gly Thr Pro Trp Thr Phe Gly Gly Gly Thr Lys Leu Glu Ile Lys Arg
            115                 120                 125

Thr Val Ala Ala Pro Ser Val Phe Ile Phe Pro Pro Ser Asp Glu Gln

```
              130                 135                 140
Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 100
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 100
gggccagtgg atagacagat g                                           21

<210> SEQ ID NO 101
<211> LENGTH: 1401
<212> TYPE: DNA
<213> ORGANISM: Mus musculus

<400> SEQUENCE: 101
atgggatgga actggatctt tctcttcctc ctgtcaggaa ctgcaggtgt cctctctgag    60
gtccagctgc agcagtctgg acctgaactg gtgaagcctg ggcttcagt gaagatatcc    120 tgcaaggctt ctggatacac attcactgac tacaacatgg actgggtgaa gcagagccat   180
ggagagagcc ttgagtggat tggatatatt tatcctaaca atggtggttc tggctacaac   240
cagaagttca agagcaaggc cacattgact gtagacaagt cctccagcac agcctacatg   300
gagctccaca gcctgacatc tgaagactct gcagtctatt actgtgcaag acgggatagt   360
tactatggtt tcgacatggc ctggtttgct tactggggcc aagggactct ggtcactgtc   420
tctgcagcca aaacgacacc cccatctgtc tatccactgg cccctggatc tgctgcccaa   480
actaactcca tggtgaccct gggatgcctg gtcaagggct atttccctga gccagtgaca   540
gtgacctgga actctggatc cctgtccagc ggtgtgcaca ccttcccagc tgtcctgcag   600
tctgacctct acactctgag cagctcagtg actgtcccct ccagcacctg gccagccag   660 accgtcacct gcaacgttgc ccacccggcc agcagcacca aggtggacaa gaaaattgtg   720
cccagggatt gtggttgtaa gccttgcata tgtacagtcc agaagtatc atctgtcttc   780 atcttccccc caaagcccaa ggatgtgctc accattactc tgactcctaa ggtcacgtgt   840
gttgtggtag acatcagcaa ggatgatccc gaggtccagt tcagctggtt tgtagatgat   900
gtggaggtgc acacagctca gacaaaaccc cggaggagc agttcaacag cactttccgt   960
tcagtcagtg aacttcccat catgcaccag gactggctca atggcaagga gttcaaatgc  1020
agggtcaaca gtgcagcttt ccctgccccc atcgagaaaa ccatctccaa aaccaaggc   1080 agaccgaagg ctccacaggt gtacaccatt ccacctccca ggagcagat ggccaaggat   1140 aaagtcagtc tgacctgcat gataacagac ttcttccctg aagacattac tgtggagtgg  1200
```

```
cagtggaatg ggcagccagc ggagaactac aagaacactc agcccatcat ggacacagat   1260
ggctcttact tcgtctacag caagctcaat gtgcagaaga gcaactggga ggcaggaaat   1320
actttcacct gctctgtgtt acatgagggc ctgcacaacc accatactga agagcctc     1380 tcccactctc ctggtaaatg a                                              1401
```

<210> SEQ ID NO 102
<211> LENGTH: 466
<212> TYPE: PRT
<213> ORGANISM: Mus musculus

<400> SEQUENCE: 102

```
Met Gly Trp Asn Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Glu Ser Leu
    50                  55                  60

Glu Trp Ile Gly Tyr Ile Tyr Pro Asn Asn Gly Ser Gly Tyr Asn
65                  70                  75                  80

Gln Lys Phe Lys Ser Lys Ala Thr Leu Thr Val Asp Lys Ser Ser Ser
                85                  90                  95

Thr Ala Tyr Met Glu Leu His Ser Leu Thr Ser Glu Asp Ser Ala Val
            100                 105                 110

Tyr Tyr Cys Ala Arg Arg Asp Ser Tyr Tyr Gly Phe Asp Met Ala Trp
        115                 120                 125

Phe Ala Tyr Trp Gly Gln Gly Thr Leu Val Thr Val Ser Ala Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Gln Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Val Glu Val His
    290                 295                 300

Thr Ala Gln Thr Lys Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335
```

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
            355                 360                 365

Thr Ile Pro Pro Pro Lys Glu Gln Met Ala Lys Asp Lys Val Ser Leu
370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Val Tyr Ser Lys Leu Asn Val Gln
            420                 425                 430

Lys Ser Asn Trp Glu Ala Gly Asn Thr Phe Thr Cys Ser Val Leu His
            435                 440                 445

Glu Gly Leu His Asn His His Thr Glu Lys Ser Leu Ser His Ser Pro
            450                 455                 460

Gly Lys
465

<210> SEQ ID NO 103
<211> LENGTH: 705
<212> TYPE: DNA
<213> ORGANISM: Mus musculus

<400> SEQUENCE: 103
atgagtgtgc ccactcaggt cctggggttg ctgctgctgt ggcttacagg tgccagatgt      60
gacatccaga tgactcagtc tccagcctcc ctatctgcat ctgtgggaga aactgtcacc     120
atcacatgtc gaccaagtga gaatatttac aataatttag catggtatca acagaaacag     180
ggaaaatctc ctcagctcct ggtctatgtt gcaacaaatt tagcagaagg tgtgccatca     240
aggttcagtg gcagtggatc aggcacacgg ttttctctga agatcaacag cctgcagcct     300
gaagattttg ggagtattac tgtcaacatt cttatggtac tccgtggac gttcggtgga     360 ggcaccaagc tggagatcaa acgggctgat gctgcaccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag cacactcacg     600
ttgaccaagg acgagtatga acgacataac agctatacct gtgaggccac tcacaagaca     660
tcaacttcac ccattgtcaa gagcttcaac aggaatgagt gttag                     705

<210> SEQ ID NO 104
<211> LENGTH: 234
<212> TYPE: PRT
<213> ORGANISM: Mus musculus

<400> SEQUENCE: 104

Met Ser Val Pro Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Pro Ser Glu Asn
        35                  40                  45

Ile Tyr Asn Asn Leu Ala Trp Tyr Gln Gln Lys Gln Gly Lys Ser Pro
    50                  55                  60

Gln Leu Leu Val Tyr Val Ala Thr Asn Leu Ala Glu Gly Val Pro Ser
 65                  70                  75                  80

Arg Phe Ser Gly Ser Gly Ser Gly Thr Arg Phe Ser Leu Lys Ile Asn
                 85                  90                  95

Ser Leu Gln Pro Glu Asp Phe Gly Lys Tyr Tyr Cys Gln His Ser Tyr
            100                 105                 110

Gly Thr Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 105
<211> LENGTH: 31
<212> TYPE: DNA
<213> ORGANISM: Artificial Sequence
<220> FEATURE:
<223> OTHER INFORMATION: Synthetic primer sequence

<400> SEQUENCE: 105
taagaattcc accatgggat ggaactggat c                              31

<210> SEQ ID NO 106
<211> LENGTH: 21
<212> TYPE: DNA
<213> ORGANISM: Artificial Sequence
<220> FEATURE:
<223> OTHER INFORMATION: Synthetic primer sequence

<400> SEQUENCE: 106
cagagacagt gaccagagtc c                                         21

<210> SEQ ID NO 107
<211> LENGTH: 1006
<212> TYPE: DNA
<213> ORGANISM: Mus musculus

<400> SEQUENCE: 107
tcgcgaaaac aacagcccca tcggtctatc cactggcccc tgtgtgtgga gatacaactg      60
gctcctcggt gactctagga tgcctggtca agggttattt ccctgagcca gtgaccttga     120
cctggaactc tggatccctg tccagtggtg tgcacacctt cccagctgtc ctgcagtctg     180
acctctacac cctcagcagc tcagtgactg taacctcgag cacctggccc agccagtcca     240
tcacctgcaa tgtggcccac ccggcaagca gcaccaaggt ggacaagaaa attgagccca     300
gagggcccac aatcaagccc tgtcctccat gcaaatgccc agcacctaac ctcttgggtg     360
gaccatccgt cttcatcttc cctccaaaga tcaaggatgt actcatgatc tccctgagcc     420

```
ccatagtcac atgtgtggtg gtggatgtga gcgaggatga cccagatgtc cagatcagct    480
ggtttgtgaa caacgtggaa gtacacacag ctcagacaca aacccataga gaggattaca    540
acagtactct ccgggtggtc agtgccctcc ccatccagca ccaggactgg atgagtggca    600
aggagttcaa atgcaaggtc aacaacaaag acctcccagc gcccatcgag agaaccatct    660
caaaacccaa agggtcagta agagcaccac aggtatatgt cttgcctcca ccagaagaag    720
agatgactaa gaaacaggtc actctgacct gcatggtcac agacttcatg cctgaagaca    780
tttacgtgga gtggaccaac aacgggaaaa cagagctaaa ctacaagaac actgaaccag    840
tcctggactc tgatggttct tacttcatgt acagcaagct gagagtggaa aagaagaact    900
gggtggaaag aaatagctac tcctgttcag tggtccacga gggtctgcac aatcaccaca    960
cgactaagag cttctcccgg actccgggta aatgataagc ggccgc                    1006
```

<210> SEQ ID NO 108
<211> LENGTH: 330
<212> TYPE: PRT
<213> ORGANISM: Mus musculus

<400> SEQUENCE: 108

```
Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270
```

```
Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 109
<211> LENGTH: 32
<212> TYPE: DNA
<213> ORGANISM: Artificial Sequence
<220> FEATURE:
<223> OTHER INFORMATION: Synthetic primer sequence

<400> SEQUENCE: 109
taagaattcc accatgagtg tgcccactca gg                                 32

<210> SEQ ID NO 110
<211> LENGTH: 21
<212> TYPE: DNA
<213> ORGANISM: Artificial Sequence
<220> FEATURE:
<223> OTHER INFORMATION: Synthetic primer sequence

<400> SEQUENCE: 110
gcccgtttga tctccagctt g                                             21

<210> SEQ ID NO 111
<211> LENGTH: 333
<212> TYPE: DNA
<213> ORGANISM: Mus musculus

<400> SEQUENCE: 111
tcgcgatgcg gccccaactg tatccatctt cccaccatcc agtgagcagt taacatctgg   60
aggtgcctca gtcgtgtgct tcttgaacaa cttctacccc aaagacatca atgtcaagtg  120
gaagattgat ggcagtgaac gacaaaatgg cgtcctgaac agttggactg atcaggacag  180
caaagacagc acctacagca tgagcagcac cctcacgttg accaaggacg agtatgaacg  240
acataacagc tatacctgtg aggccactca caagacatca acttcaccca ttgtcaagag  300
cttcaacagg aatgagtgtt gataagcggc cgc                                333

<210> SEQ ID NO 112
<211> LENGTH: 107
<212> TYPE: PRT
<213> ORGANISM: Mus musculus

<400> SEQUENCE: 112

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80
```

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 113
<211> LENGTH: 1430
<212> TYPE: DNA
<213> ORGANISM: Artificial Sequence
<220> FEATURE:
<223> OTHER INFORMATION: Synthetic nucleotide sequence

<400> SEQUENCE: 113

```
atgggatgga actggatctt tctcttcctc ctgtcaggaa ctgcaggtgt cctctctgag      60
gtccagctgc agcagtctgg acctgaactg gtgaagcctg gggcttcagt gaagatatcc     120
tgcaaggctt ctggatacac attcactgac tacaacatgg actgggtgaa gcagagccat     180
ggagagagcc ttagtggat tggatatatt tatcctaaca atggtggttc tggctacaac     240
cagaagttca gagcaaggc cacattgact gtagacaagt cctccagcac agcctacatg     300
gagctccaca gcctgacatc tgaagactct gcagtctatt actgtgcaag acgggatagt     360
tactatggtt tcgacatggc ctggtttgct tactggggcc aagggactct ggtcactgtc     420
tctgcagcga aaacaacagc cccatcggtc tatccactgg ccctgtgtgt ggagataca     480
actggctcct cggtgactct aggatgcctg gtcaagggt atttccctga ccagtgacc     540
ttgacctgga actctggatc cctgtccagt ggtgtgcaca ccttcccagc tgtcctgcag     600
tctgacctct acaccctcag cagctcagtg actgtaacct cgagcacctg gcccagccag     660
tccatcacct gcaatgtggc ccacccggca agcagcacca aggtggacaa gaaaattgag     720
cccagagggc ccacaatcaa gccctgtcct ccatgcaaat gcccagcacc taacctcttg     780
ggtggaccat ccgtcttcat cttccctcca aagatcaagg atgtactcat gatctccctg     840
agccccatag tcacatgtgt ggtggtggat gtgagcgagg atgacccaga tgtccagatc     900
agctggtttg tgaacaacgt ggaagtacac acagctcaga cacaaaccca tagagaggat     960
tacaacagta ctctccgggt ggtcagtgcc ctccccatcc agcaccagga ctggatgagt    1020
ggcaaggagt tcaaatgcaa ggtcaacaac aaagacctcc cagcgcccat cgagagaacc    1080
atctcaaaac ccaaagggtc agtaagagca ccacaggtat atgtcttgcc tccaccagaa    1140
gaagagatga ctaagaaaca ggtcactctg acctgcatgg tcacagactt catgcctgaa    1200
gacatttacg tggagtggac caacaacggg aaaacagagc taaactacaa gaacactgaa    1260
ccagtcctgg actctgatgg ttcttacttc atgtacagca agctgagagt ggaaaagaag    1320
aactgggtgg aaagaaatag ctactcctgt tcagtggtcc acgagggtct gcacaatcac    1380
cacacgacta agagcttctc ccggactccg ggtaaatgat aagcggccgc              1430
```

<210> SEQ ID NO 114
<211> LENGTH: 472
<212> TYPE: PRT
<213> ORGANISM: Artificial Sequence
<220> FEATURE:
<223> OTHER INFORMATION: Synthetic peptide sequence

<400> SEQUENCE: 114

Met Gly Trp Asn Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys

```
                20                  25                  30
Pro Gly Ala Ser Val Lys Ile Ser Cys Lys Ala Ser Gly Tyr Thr Phe
            35                  40                  45
Thr Asp Tyr Asn Met Asp Trp Val Lys Gln Ser His Gly Glu Ser Leu
        50                  55                  60
Glu Trp Ile Gly Tyr Ile Tyr Pro Asn Asn Gly Ser Gly Tyr Asn
65                  70                  75                  80
Gln Lys Phe Lys Ser Lys Ala Thr Leu Thr Val Asp Lys Ser Ser Ser
                85                  90                  95
Thr Ala Tyr Met Glu Leu His Ser Leu Thr Ser Glu Asp Ser Ala Val
            100                 105                 110
Tyr Tyr Cys Ala Arg Arg Asp Ser Tyr Tyr Gly Phe Asp Met Ala Trp
        115                 120                 125
Phe Ala Tyr Trp Gly Gln Gly Thr Leu Val Thr Val Ser Ala Ala Lys
        130                 135                 140
Thr Thr Ala Pro Ser Val Tyr Pro Leu Ala Pro Val Cys Gly Asp Thr
145                 150                 155                 160
Thr Gly Ser Ser Val Thr Leu Gly Cys Leu Val Lys Gly Tyr Phe Pro
                165                 170                 175
Glu Pro Val Thr Leu Thr Trp Asn Ser Gly Ser Leu Ser Ser Gly Val
            180                 185                 190
His Thr Phe Pro Ala Val Leu Gln Ser Asp Leu Tyr Thr Leu Ser Ser
        195                 200                 205
Ser Val Thr Val Thr Ser Ser Thr Trp Pro Ser Gln Ser Ile Thr Cys
    210                 215                 220
Asn Val Ala His Pro Ala Ser Ser Thr Lys Val Asp Lys Lys Ile Glu
225                 230                 235                 240
Pro Arg Gly Pro Thr Ile Lys Pro Cys Pro Pro Cys Lys Cys Pro Ala
                245                 250                 255
Pro Asn Leu Leu Gly Gly Pro Ser Val Phe Ile Phe Pro Pro Lys Ile
            260                 265                 270
Lys Asp Val Leu Met Ile Ser Leu Ser Pro Ile Val Thr Cys Val Val
        275                 280                 285
Val Asp Val Ser Glu Asp Asp Pro Asp Val Gln Ile Ser Trp Phe Val
    290                 295                 300
Asn Asn Val Glu Val His Thr Ala Gln Thr Gln Thr His Arg Glu Asp
305                 310                 315                 320
Tyr Asn Ser Thr Leu Arg Val Val Ser Ala Leu Pro Ile Gln His Gln
                325                 330                 335
Asp Trp Met Ser Gly Lys Glu Phe Lys Cys Lys Val Asn Asn Lys Asp
            340                 345                 350
Leu Pro Ala Pro Ile Glu Arg Thr Ile Ser Lys Pro Lys Gly Ser Val
        355                 360                 365
Arg Ala Pro Gln Val Tyr Val Leu Pro Pro Glu Glu Glu Met Thr
    370                 375                 380
Lys Lys Gln Val Thr Leu Thr Cys Met Val Thr Asp Phe Met Pro Glu
385                 390                 395                 400
Asp Ile Tyr Val Glu Trp Thr Asn Asn Gly Lys Thr Glu Leu Asn Tyr
                405                 410                 415
Lys Asn Thr Glu Pro Val Leu Asp Ser Asp Gly Ser Tyr Phe Met Tyr
            420                 425                 430
Ser Lys Leu Arg Val Glu Lys Lys Asn Trp Val Glu Arg Asn Ser Tyr
        435                 440                 445
```

Ser Cys Ser Val Val His Glu Gly Leu His Asn His His Thr Thr Lys
    450                 455                 460

Ser Phe Ser Arg Thr Pro Gly Lys
465                 470

<210> SEQ ID NO 115
<211> LENGTH: 716
<212> TYPE: DNA
<213> ORGANISM: Artificial Sequence
<220> FEATURE:
<223> OTHER INFORMATION: Synthetic nucleotide sequence

<400> SEQUENCE: 115

```
atgagtgtgc ccactcaggt cctggggttg ctgctgctgt ggcttacagg tgccagatgt      60
gacatccaga tgactcagtc tccagcctcc ctatctgcat ctgtgggaga aactgtcacc     120
atcacatgtc gaccaagtga gaatatttac aataatttag catggtatca acagaaacag     180
ggaaaatctc ctcagctcct ggtctatgtt gcaacaaatt tagcagaagg tgtgccatca     240
aggttcagtg gcagtggatc aggcacacgg ttttctctga gatcaacag cctgcagcct     300 gaagattttg ggagtatta ctgtcaacat tcttatggta ctccgtggac gttcggtgga     360
ggcaccaagc tggagatcaa cgggccgat gcggccccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag caccctcacg     600
ttgaccaagg acgagtatga acgacataac agctatacct gtgaggccac tcacaagaca     660
tcaacttcac ccattgtcaa gagcttcaac aggaatgagt gttgataagc ggccgc         716
```

<210> SEQ ID NO 116
<211> LENGTH: 234
<212> TYPE: PRT
<213> ORGANISM: Artificial Sequence
<220> FEATURE:
<223> OTHER INFORMATION: Synthetic peptide sequence

<400> SEQUENCE: 116

Met Ser Val Pro Thr Gln Val Leu Gly Leu Leu Leu Trp Leu Thr
1               5                   10                  15

Gly Ala Arg Cys Asp Ile Gln Met Thr Gln Ser Pro Ala Ser Leu Ser
                20                  25                  30

Ala Ser Val Gly Glu Thr Val Thr Ile Thr Cys Arg Pro Ser Glu Asn
        35                  40                  45

Ile Tyr Asn Asn Leu Ala Trp Tyr Gln Gln Lys Gln Gly Lys Ser Pro
    50                  55                  60

Gln Leu Leu Val Tyr Val Ala Thr Asn Leu Ala Glu Gly Val Pro Ser
65                  70                  75                  80

Arg Phe Ser Gly Ser Gly Ser Gly Thr Arg Phe Ser Leu Lys Ile Asn
                85                  90                  95

Ser Leu Gln Pro Glu Asp Phe Gly Lys Tyr Tyr Cys Gln His Ser Tyr
                100                 105                 110

Gly Thr Pro Trp Thr Phe Gly Gly Gly Thr Lys Leu Glu Ile Lys Arg
            115                 120                 125

Ala Asp Ala Ala Pro Thr Val Ser Ile Phe Pro Pro Ser Ser Glu Gln
        130                 135                 140

Leu Thr Ser Gly Gly Ala Ser Val Val Cys Phe Leu Asn Asn Phe Tyr

-continued

```
            145                 150                 155                 160
        Pro Lys Asp Ile Asn Val Lys Trp Lys Ile Asp Gly Ser Glu Arg Gln
                        165                 170                 175

Asn Gly Val Leu Asn Ser Trp Thr Asp Gln Asp Ser Lys Asp Ser Thr
                        180                 185                 190

Tyr Ser Met Ser Ser Thr Leu Thr Leu Thr Lys Asp Glu Tyr Glu Arg
                    195                 200                 205

His Asn Ser Tyr Thr Cys Glu Ala Thr His Lys Thr Ser Thr Ser Pro
                210                 215                 220

Ile Val Lys Ser Phe Asn Arg Asn Glu Cys
        225                 230
```